United States Patent
Yamatani

(10) Patent No.: US 12,404,271 B2
(45) Date of Patent: Sep. 2, 2025

(54) ORGANIC ELECTROLUMINESCENCE DEVICE AND POLYCYCLIC COMPOUND FOR ORGANIC ELECTROLUMINESCENCE DEVICE

(71) Applicant: SAMSUNG DISPLAY CO., LTD., Yongin-si (KR)

(72) Inventor: Akinori Yamatani, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 230 days.

(21) Appl. No.: 16/523,168

(22) Filed: Jul. 26, 2019

(65) Prior Publication Data
US 2020/0044159 A1    Feb. 6, 2020

(30) Foreign Application Priority Data

Jul. 31, 2018  (KR) .................. 10-2018-0088926

(51) Int. Cl.
*H01L 51/50* (2006.01)
*C07D 471/04* (2006.01)
(Continued)

(52) U.S. Cl.
CPC ......... *H10K 85/631* (2023.02); *C07D 471/04* (2013.01); *C07D 497/14* (2013.01);
(Continued)

(58) Field of Classification Search
CPC .... C07F 5/027; H01L 51/008; H01L 51/0059; H01L 51/5012; H01L 51/5016; C09K 2211/1018; C09K 11/06
See application file for complete search history.

(56) References Cited

U.S. PATENT DOCUMENTS

| | | |
|---|---|---|
| 6,602,618 B2 | 8/2003 | Watanabe et al. |
| 10,374,166 B2 | 8/2019 | Hatakeyama et al. |

(Continued)

FOREIGN PATENT DOCUMENTS

| | | | | |
|---|---|---|---|---|
| CA | 3017002 A1 | * | 3/2019 | ............. C09K 11/06 |
| CH | 422200 A | * | 10/1966 | ............. C09B 57/00 |

(Continued)

OTHER PUBLICATIONS

Chibani et al. "Excited States of Ladder-Type π-Conjugated Dyes with a Joint SOS-CIS(D) and PCM-TD-DFT Approach" J. Phys. Chem. A. 119—pp. 5417-5425. 2015 (Year: 2015).*

(Continued)

*Primary Examiner* — Gregory D Clark
(74) *Attorney, Agent, or Firm* — Womble Bond Dickinson (US) LLP

(57) ABSTRACT

An organic electroluminescence device includes a first electrode, a hole transport region on the first electrode, an emission layer on the hole transport region, the emission layer including a condensed polycyclic compound of three or more six-membered rings, at least two six-membered rings among the six-membered rings including an electron donor moiety and an electron acceptor moiety at facing positions, respectively, the at least two six-membered rings not being immediately adjacent to each other, an electron transport region on the emission layer, and a second electrode on the electron transport region.

21 Claims, 2 Drawing Sheets

(51) Int. Cl.

| | | |
|---|---|---|
| C07D 497/14 | (2006.01) | |
| C07F 5/02 | (2006.01) | |
| C07F 7/10 | (2006.01) | |
| C07F 9/6571 | (2006.01) | |
| C09K 11/02 | (2006.01) | |
| C09K 11/06 | (2006.01) | |
| H10K 85/40 | (2023.01) | |
| H10K 85/60 | (2023.01) | |
| H10K 50/11 | (2023.01) | |
| H10K 50/15 | (2023.01) | |
| H10K 50/16 | (2023.01) | |
| H10K 50/17 | (2023.01) | |
| H10K 50/18 | (2023.01) | |
| H10K 101/10 | (2023.01) | |
| H10K 101/20 | (2023.01) | |

(52) U.S. Cl.
CPC ............... *C07F 5/027* (2013.01); *C07F 7/10* (2013.01); *C07F 9/657163* (2013.01); *C09K 11/025* (2013.01); *C09K 11/06* (2013.01); *H10K 85/40* (2023.02); *H10K 85/60* (2023.02); *H10K 85/657* (2023.02); *H10K 85/6572* (2023.02); *H10K 85/658* (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02); *H10K 2101/10* (2023.02); *H10K 2101/20* (2023.02)

(56) References Cited

U.S. PATENT DOCUMENTS

| | | | |
|---|---|---|---|
| 10,483,471 B2 | 11/2019 | Ishidai et al. | |
| 10,804,482 B2 | 10/2020 | Sakamoto | |
| 2004/0170863 A1* | 9/2004 | Kim ..................... | C07D 235/18 313/506 |
| 2007/0059552 A1 | 3/2007 | Takeda et al. | |
| 2012/0319091 A1 | 12/2012 | Kato | |
| 2014/0034926 A1 | 2/2014 | Matsubara et al. | |
| 2015/0236274 A1 | 8/2015 | Hatakeyama et al. | |
| 2016/0351811 A1 | 12/2016 | Lam et al. | |
| 2018/0069182 A1 | 3/2018 | Hatakeyama et al. | |
| 2018/0094000 A1 | 4/2018 | Hatakeyama et al. | |
| 2018/0108857 A1 | 4/2018 | Adachi et al. | |
| 2018/0301629 A1 | 10/2018 | Hatakeyama et al. | |
| 2019/0058124 A1 | 2/2019 | Hatakeyama et al. | |
| 2019/0115538 A1 | 4/2019 | Lim et al. | |
| 2019/0207112 A1 | 7/2019 | Hatakeyama et al. | |
| 2019/0348617 A1* | 11/2019 | Mamada ............ | H10K 85/6572 |
| 2021/0159411 A1 | 5/2021 | Sim et al. | |
| 2021/0273174 A1 | 9/2021 | Kuwabara et al. | |
| 2021/0305512 A1 | 9/2021 | Suzaki | |
| 2021/0376250 A1 | 12/2021 | Suzaki | |

FOREIGN PATENT DOCUMENTS

| | | | | |
|---|---|---|---|---|
| CN | 107417715 A | | 12/2017 | |
| JP | 2007-73891 A | | 3/2007 | |
| JP | 2012116784 | * | 6/2012 | ............ C07D 471/04 |
| JP | 5935199 B2 | | 6/2016 | |
| JP | WO2017/138526 A1 | | 8/2017 | |
| JP | 2018043984 A2 | | 3/2018 | |
| KR | 10-1516062 B1 | | 4/2015 | |
| KR | 10-1523124 B1 | | 5/2015 | |
| KR | 10-2016-0119683 A | | 10/2016 | |
| KR | 10-2017-0082447 A | | 7/2017 | |
| KR | 10-2017-0130434 A | | 11/2017 | |
| KR | 10-2017-0130435 A | | 11/2017 | |
| KR | 10-1876763 B1 | | 7/2018 | |
| KR | 10-1886773 B1 | | 8/2018 | |
| KR | 10-2018-0108604 A | | 10/2018 | |
| KR | 10-2018-0122298 A | | 11/2018 | |
| KR | 10-2018-0134850 A | | 12/2018 | |
| KR | 10-2019-0025065 | | 3/2019 | |
| KR | 10-1955647 B1 | | 3/2019 | |
| KR | 10-1955648 B1 | | 3/2019 | |
| KR | 10-2019-0035990 A | | 4/2019 | |
| KR | 10-2019-0042791 A | | 4/2019 | |
| WO | WO 2015/102118 A1 | | 7/2015 | |
| WO | WO 2016/152418 A1 | | 9/2016 | |
| WO | WO 2016/152544 A1 | | 9/2016 | |
| WO | WO 2016/152605 A1 | | 9/2016 | |
| WO | WO 2017/188111 A1 | | 11/2017 | |
| WO | WO 2018/212169 A1 | | 11/2018 | |
| WO | WO 2019/052940 | * | 3/2019 | ............. H01L 51/50 |
| WO | WO-2019052940 A1 | * | 3/2019 | ......... H01L 51/5016 |
| WO | 2021230133 A1 | | 11/2021 | |
| WO | 2022096495 A1 | | 5/2022 | |

OTHER PUBLICATIONS

Wang et al. "Synthesis of Di- and Trixanthones that Display High Stability and a Visual Fluorescence Response to Strong Acid" Chem. Asian J. 9—pp. 3307-3312. 2014 (Year: 2014).*
Coloquhour et al., Synthesis of Dixanthones and Poly(dixanthone)s by Cyclization of 2-Aryloxybenzonitriles in rifluoromethanesulfonic Acid; 2001; Org. Lett., vol. 3, No. 15, p. 2337-2340 (Year: 2001).*
Anton Pershin, et al., "Highly emissive excitons with reduced exchange energy in thermally activated delayed fluorescent molecules," Nature Communications, vol. 10, No. 597, (2019), pp. 1-5.
Agou, T., et al. "Syntheses, Structure, and Optical Properties of Ladder-Type Fused Azaborines," Organic Letters 8(11), 2006, pp. 2241-2244.
Chinese Office Action dated Mar. 17, 2023 for corresponding CN Appl. No. 201910694080.8, citing JP 2012-116784 A (previously cited), 11 pages.
English abstract for JP 2012-116784 A (previously cited), 1 page.
Office Action for U.S. Appl. No. 17/002,617 dated Mar. 17, 2023, 6 pages.
Zhang, J., et al. "The Ground State Spin Multiplicity of Schlenk-type Biradicals and the Influence of Additional Linkage to Ladder Type Structures" Chemical Physics 206, 1996, pp. 339-351.
WO-2021230133-A1 machine translation (Year: 2021).
U.S. Office Action dated May 17, 2023, issued in U.S. Appl. No. 17/110,108 (35 pages).
U.S. Notice of Allowance dated Jul. 19, 2023, issued in U.S. Appl. No. 17/002,617 (8 pages).
Notice of Allowance for U.S. Appl. No. 17/110,108 dated Dec. 22, 2023, 10 pages.
Agou, et. al., "Electronic and Optical Properties of Ladder-type Heteraborins," Chem. Eur. J. (2007), pp. 8051-8060.
Office Action for U.S. Appl. No. 16/780,744 dated Feb. 1, 2024, 8 pages.
U.S. Final Office Action dated Jun. 18, 2024, issued in U.S. Appl. No. 16/780,744 (9 pages).
U.S. Office Action dated Sep. 17, 2024, issued in U.S. Appl. No. 16/780,744 (9 pages).
Korean Notice of Allowance dated Nov. 27, 2024, issued in corresponding Korean Patent Application No. 10-2019-0042995 (7 pages).
US Final Office Action dated Feb. 24, 2025, issued in U.S. Appl. No. 16/780,744 (9 pages).
US Notice of Allowance dated Jun. 13, 2025, issued in U.S. Appl. No. 16/780,744, 8 pages.

\* cited by examiner

ORGANIC ELECTROLUMINESCENCE DEVICE AND POLYCYCLIC COMPOUND FOR ORGANIC ELECTROLUMINESCENCE DEVICE

CROSS-REFERENCE TO RELATED APPLICATION

Korean Patent Application No. 10-2018-0088926, filed on Jul. 31, 2018, in the Korean Intellectual Property Office, and entitled: "Organic Electroluminescence Device and Polycyclic Compound for Organic Electroluminescence Device," is incorporated by reference herein in its entirety.

BACKGROUND

1 Field

Embodiments relate to an organic electroluminescence device and a polycyclic compound for an organic electroluminescence device.

2. Description of the Related Art

Recently, the development of an organic electroluminescence display device as an image display device is being actively conducted. Different from a liquid crystal display device, the organic electroluminescence display device is so-called a self-luminescent display device in which holes and electrons injected from a first electrode and a second electrode recombine in an emission layer, and a light emission material including an organic compound in the emission layer emits light to attain display.

In the application of an organic electroluminescence device to a display device, the decrease of the driving voltage, and the increase of the emission efficiency and the life of the organic electroluminescence device are desired, and developments on materials for an organic electroluminescence device are being continuously pursued.

SUMMARY

Embodiments are directed to an organic electroluminescence device, including a first electrode, a hole transport region on the first electrode, an emission layer on the hole transport region, the emission layer including a condensed polycyclic compound of three or more six-membered rings, at least two six-membered rings among the six-membered rings including an electron donor moiety and an electron acceptor moiety at facing positions, respectively, the at least two six-membered rings not being immediately adjacent to each other, an electron transport region on the emission layer, and a second electrode on the electron transport region. And the first electrode and the second electrode are each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, or a compound of two or more selected from them, a mixture of two or more selected from them, or oxides thereof.

In an embodiment, the emission layer may be a delayed fluorescence emission layer including a host and a dopant, and the host or the dopant may include the polycyclic compound. In an embodiment, the emission layer may be a phosphorescence emission layer including a host and a dopant, and the host may include the polycyclic compound.

In an embodiment, the electron donor moiety may include an amine group, an oxygen atom, a sulfur atom, or a selenium atom.

In an embodiment, the electron acceptor moiety may include a carbonyl group, a boron group, a silyl group, a germyl group, a phosphine oxide group, a phosphine sulfide group, a sulfoxide group, or a sulfur dioxide group.

In an embodiment, the emission layer may emit blue light.

In an embodiment, the polycyclic compound may be represented by any one among Formula 1 to Formula 3:

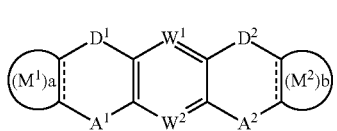

[Formula 1]

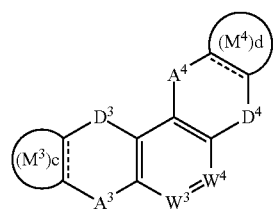

[Formula 2]

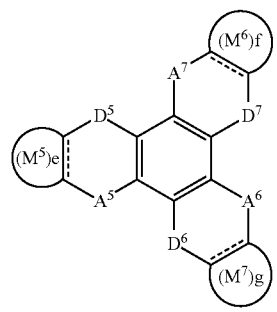

[Formula 3]

In Formula 1 to Formula 3, $A^1$ to $A^7$ are each independently CO, $BR_1$, $SiR_2R_3$, $GeR_4R_5$, $POR_6$, $PSR_7$, SO, or $SO_2$, $D^1$ to $D^7$ are each independently $NR_8$, O, S, or Se, $W^1$ to $W^4$ are each independently N or $CR_9$, a to g are each independently 0 or 1. In Formula 1 to Formula 3, $M^1$ to $M^7$ are each independently a substituted or unsubstituted aryl group having 6 to 30 ring carbon atoms, or a substituted or unsubstituted heteroaryl group having 2 to 30 ring carbon atoms. In Formula 1 to Formula 3, $R^1$ to $R^8$ are each independently a hydrogen atom, a deuterium atom, a halogen atom, a cyano group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and $R_9$ is a hydrogen atom, a deuterium atom, a halogen atom, a cyano group, a phosphine oxide group, a phosphine sulfide group, a carbonyl group, a boron group, a substituted or unsubstituted oxy group, a substituted or unsubstituted thiol group, a substituted or unsubstituted amino group, a substituted or unsubstituted silyl group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In an embodiment, $A^1$ to $A^7$ may be represented by the following Formula 4:

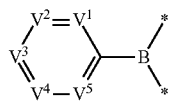

[Formula 4]

In Formula 4, $V^1$ to $V^5$ are each independently N or $CR_{10}$, provided that at least one among $V^1$ to $V^5$ is $CR_{11}$. In Formula 4, $R_{10}$ is a hydrogen atom, a deuterium atom, a halogen atom, a cyano group, a phosphine oxide group, a phosphine sulfide group, a carbonyl group, a boron group, a substituted or unsubstituted oxy group, a substituted or unsubstituted thiol group, a substituted or unsubstituted amino group, a substituted or unsubstituted silyl group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In Formula 4, $R_{11}$ is a cyano group, a substituted or unsubstituted oxy group, a substituted or unsubstituted thiol group, a substituted or unsubstituted amino group, a substituted or unsubstituted silyl group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In an embodiment, Formula 1 to Formula 3 may be represented by the following Formula 1-1 to Formula 1-3, respectively:

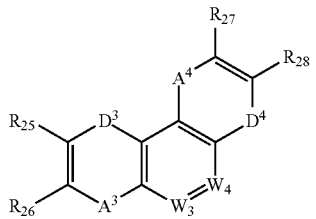

[Formula 1-1]

[Formula 1-2]

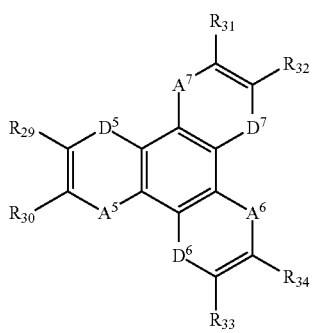

[Formula 1-3]

In Formula 1-1 to Formula 1-3, $R_{21}$ to $R_{34}$ are each independently a hydrogen atom, a deuterium atom, a halogen atom, a cyano group, a phosphine oxide group, a phosphine sulfide group, a silyl group, a carbonyl group, a boron group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and $A^1$ to $A^7$, $D^1$ to $D^7$, and $W^1$ to $W^4$ are the same as defined in Formula 1 to Formula 3.

In an embodiment, Formula 1 to Formula 3 may be represented by the following Formula 2-1 to Formula 2-3, respectively:

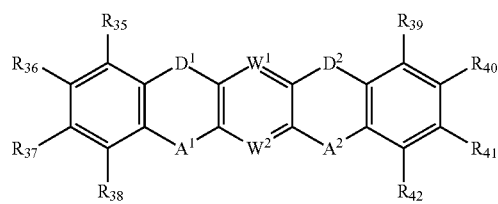

[Formula 2-1]

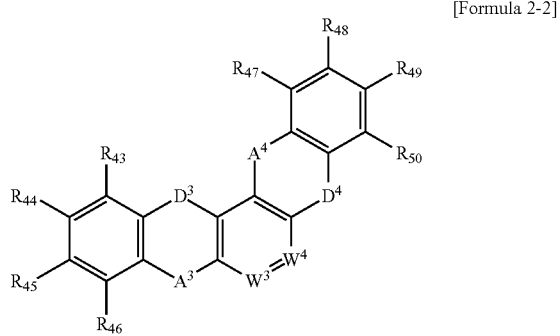

[Formula 2-2]

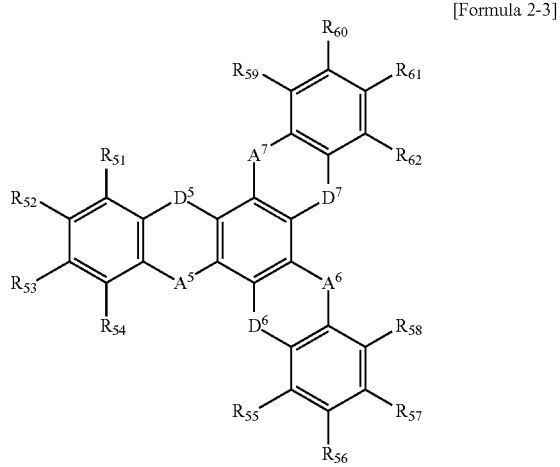

[Formula 2-3]

In Formula 2-1 to Formula 2-3, $R_{35}$ to $R_{62}$ are each independently a hydrogen atom, a deuterium atom, a halogen atom, a cyano group, a phosphine oxide group, a phosphine sulfide group, a silyl group, a carbonyl group, a boron group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and $A^1$ to $A^7$, $D^1$ to $D^7$, and $W^1$ to $W^4$ are the same as defined in Formula 1 to Formula 3.

In an embodiment, the emission layer may include at least one compound among the compounds represented in the following Compound Group 1:
[Compound Group 1]
1
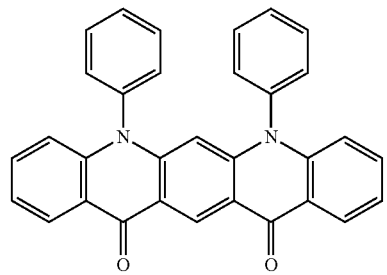
2
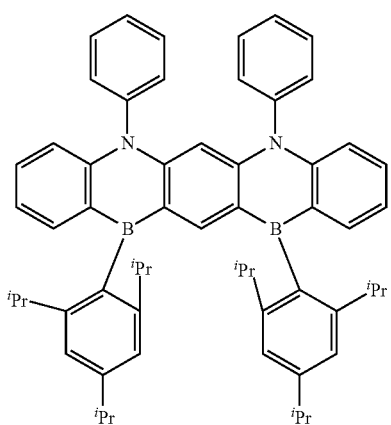
3
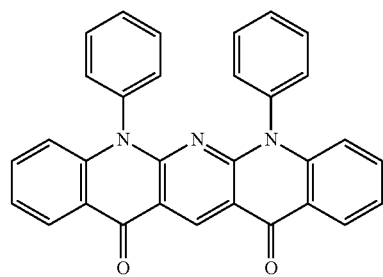
4
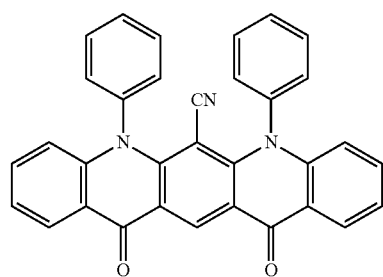
5
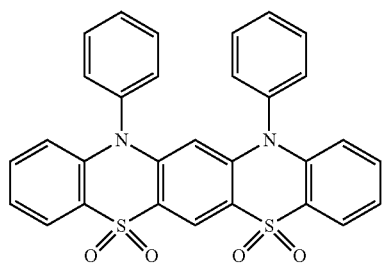
6
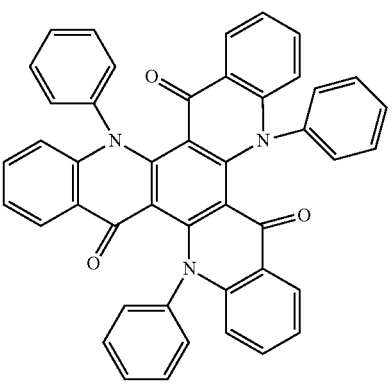
7
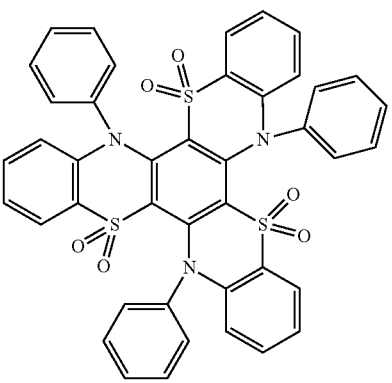
8
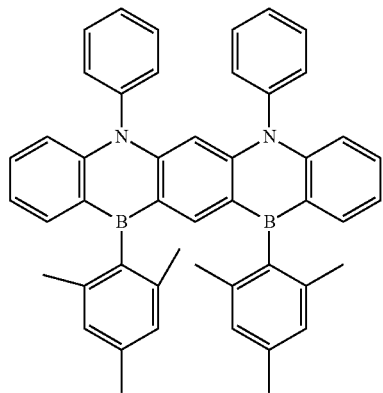

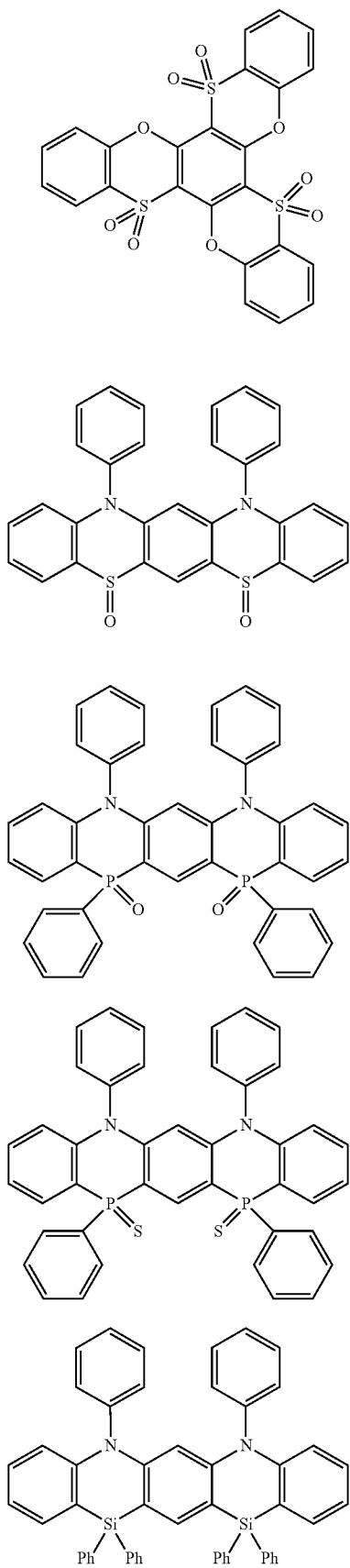

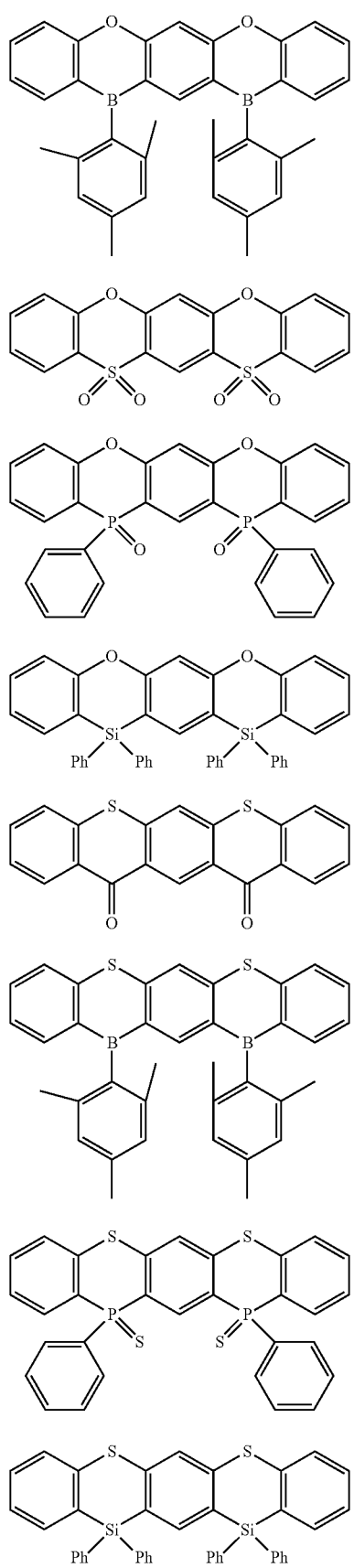
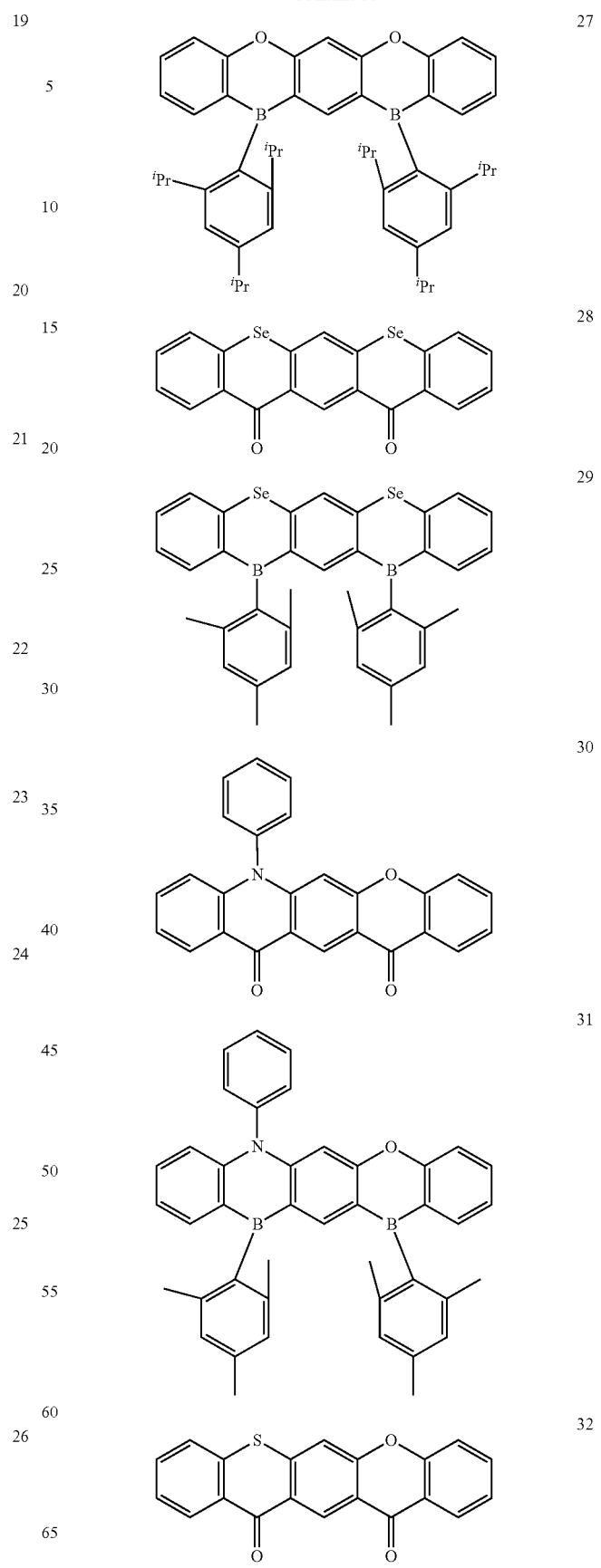

33
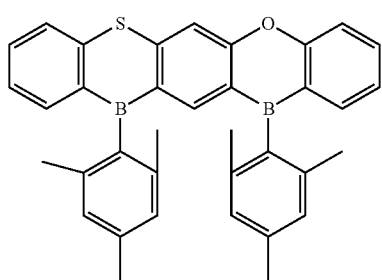
34
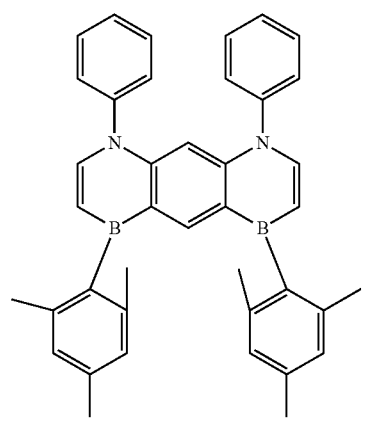
35
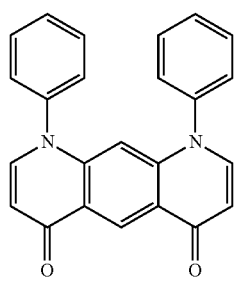
36
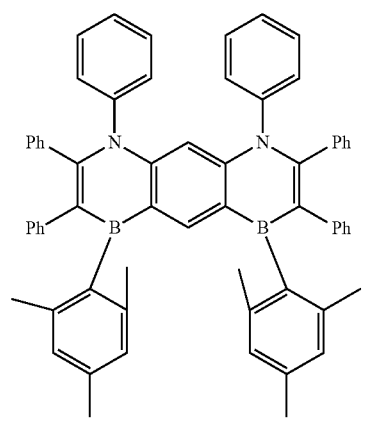
37
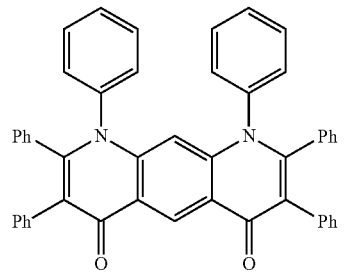
38
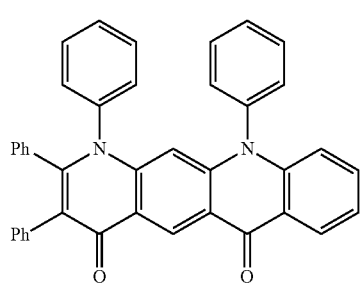
39
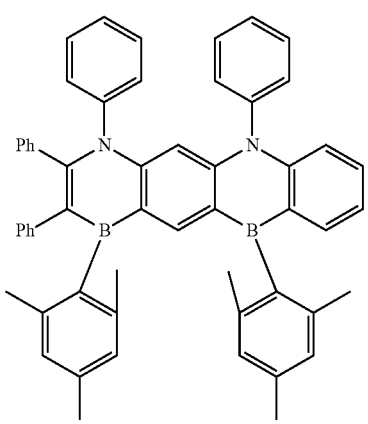
40
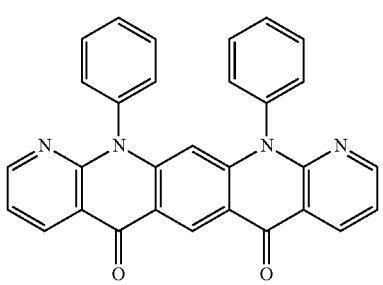

41
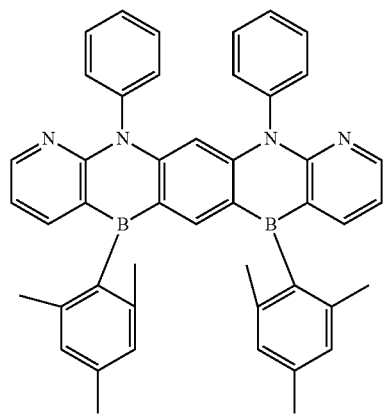
42
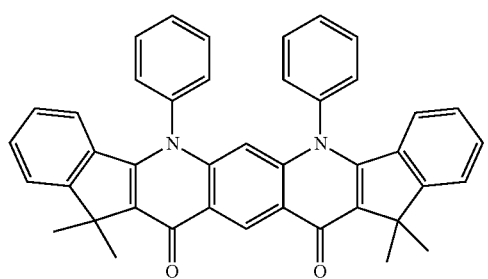
43
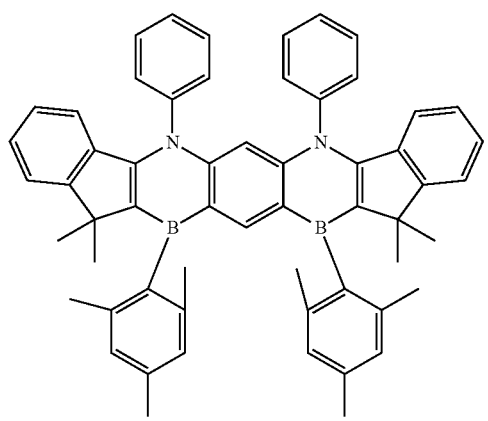
44
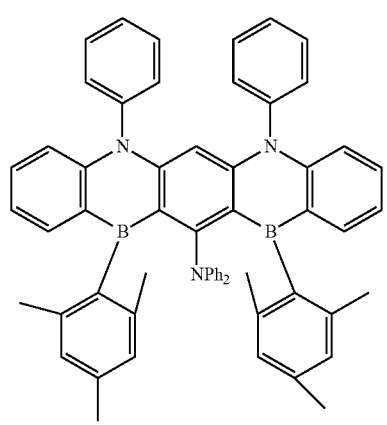
45
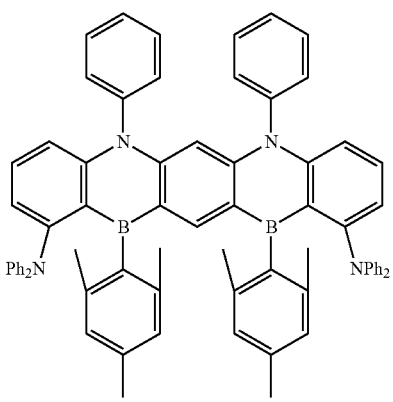
46
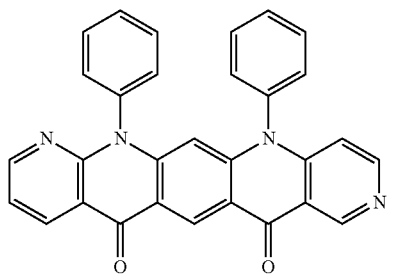
47
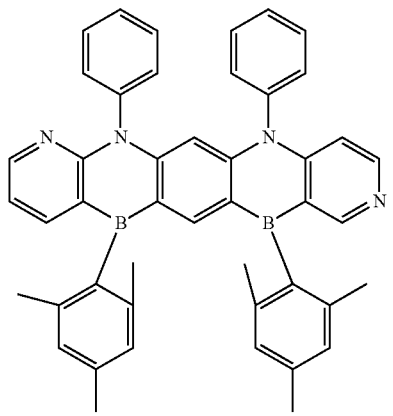
48
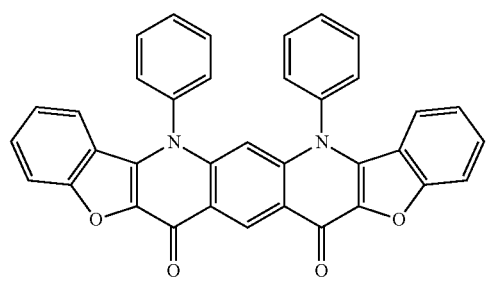

49
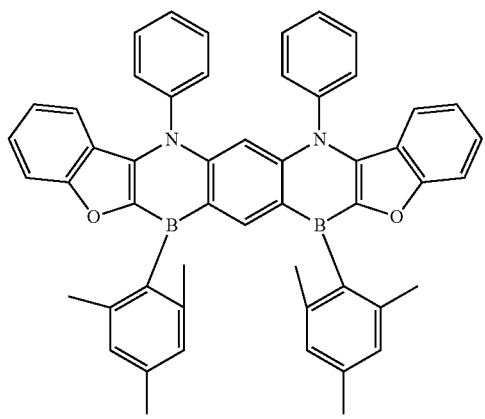
50
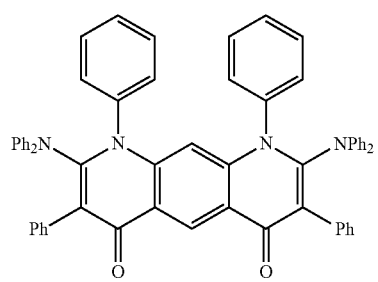
51
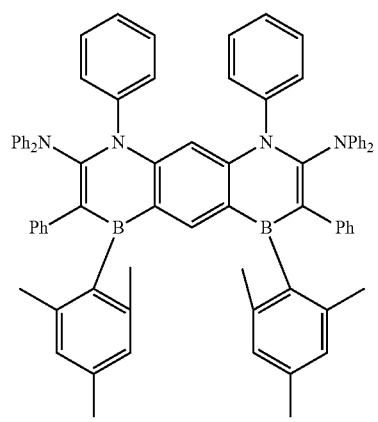
52
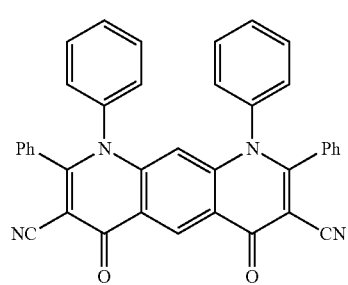
53
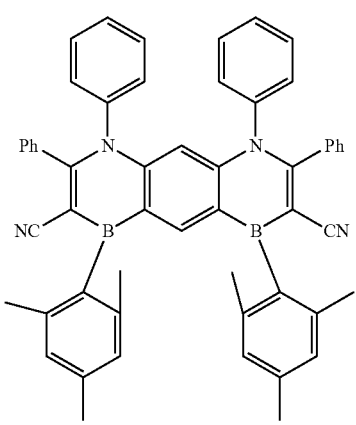
54
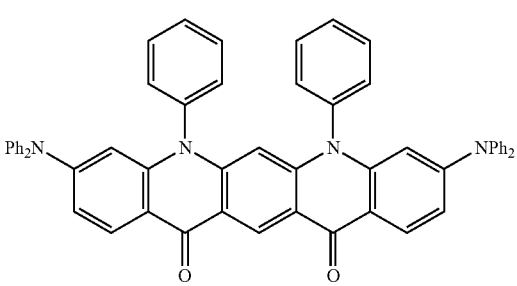
55
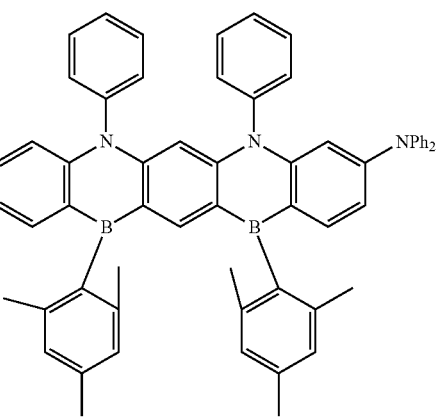
56
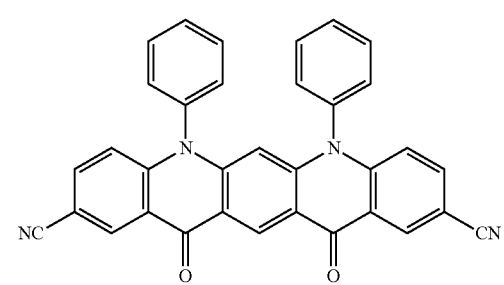

57
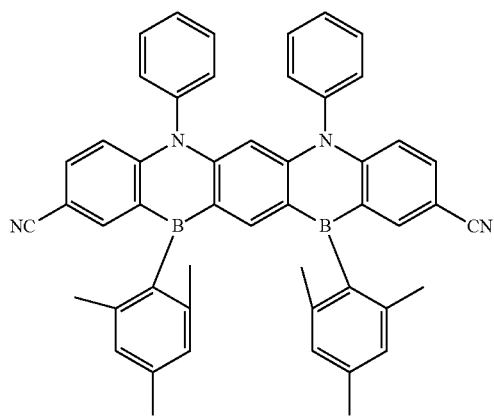
58
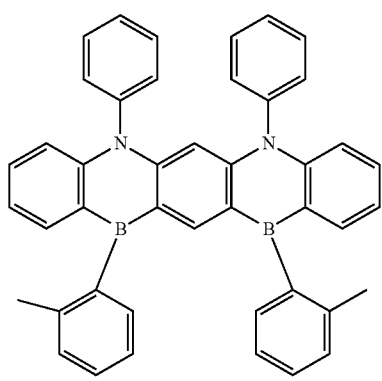
59
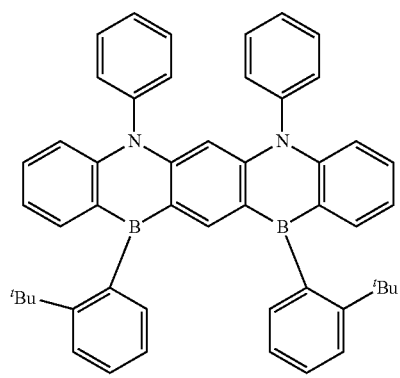
60
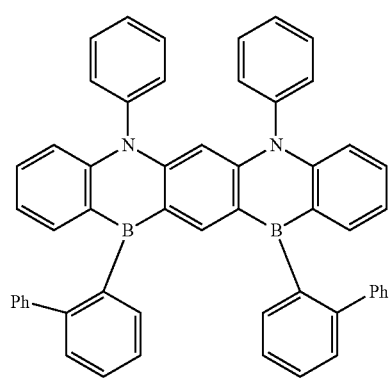
61
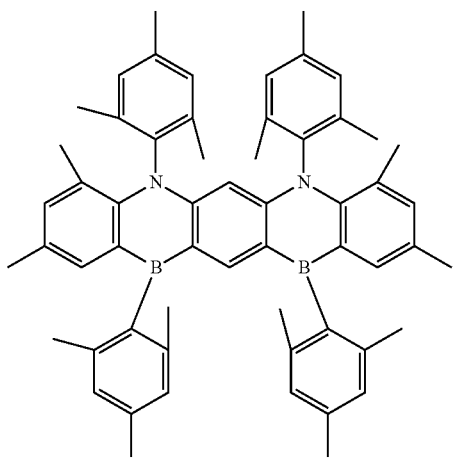
62
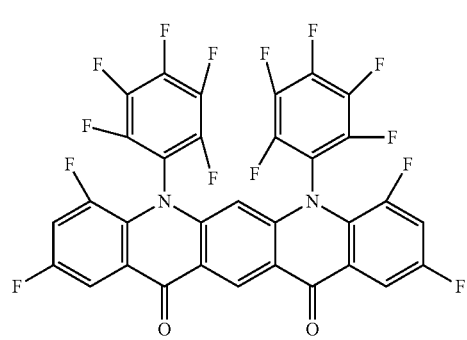
63
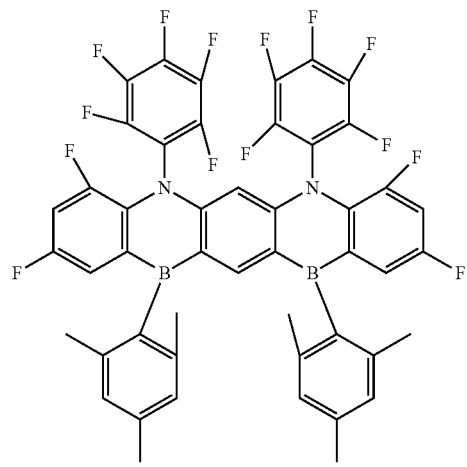
64
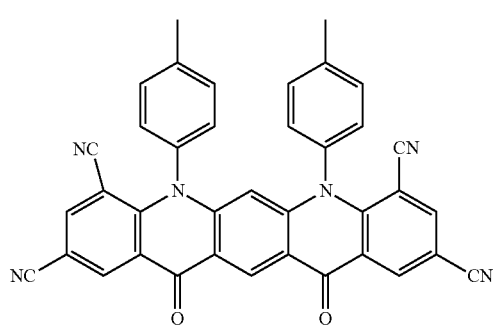

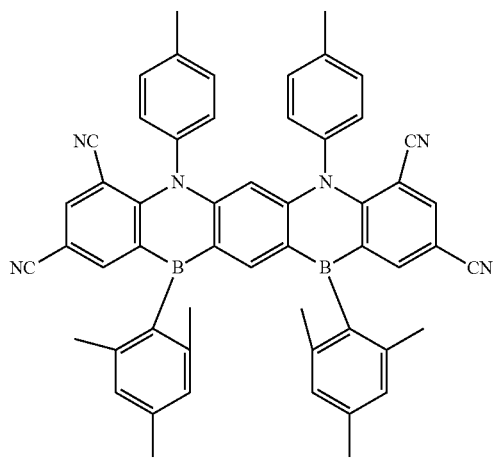
65
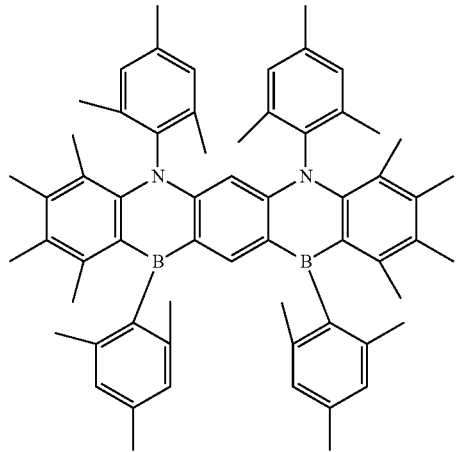
69
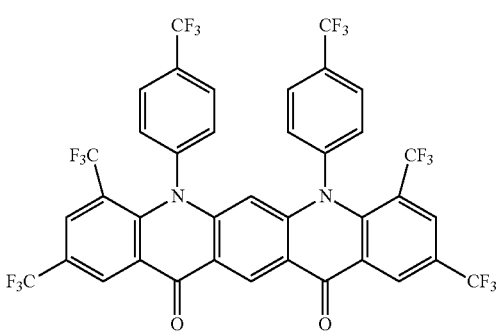
66
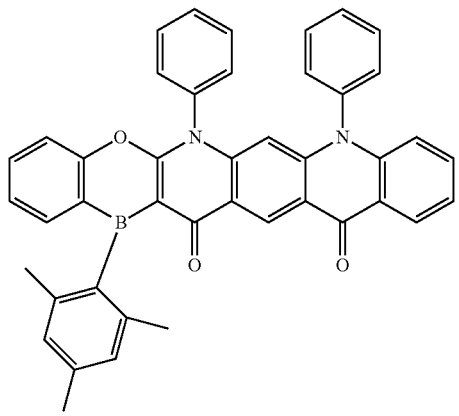
70
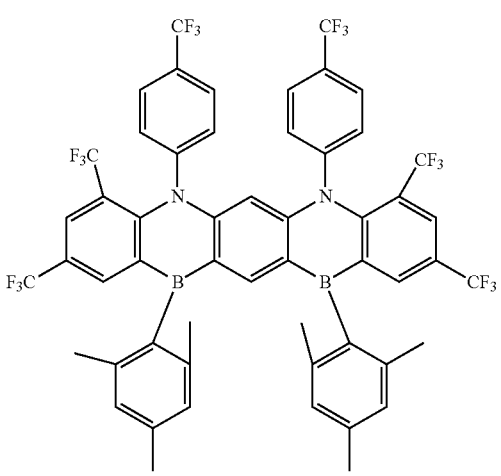
67
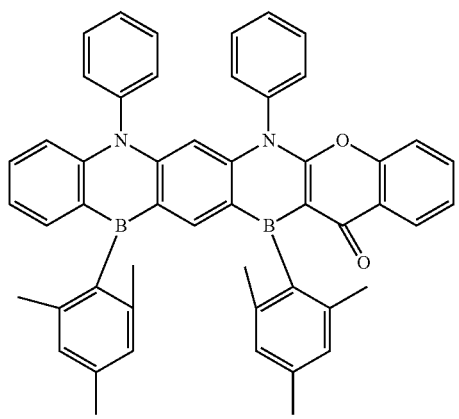
71
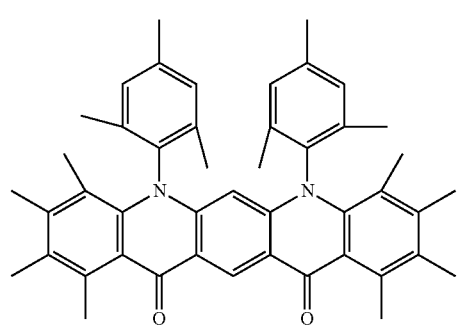
68
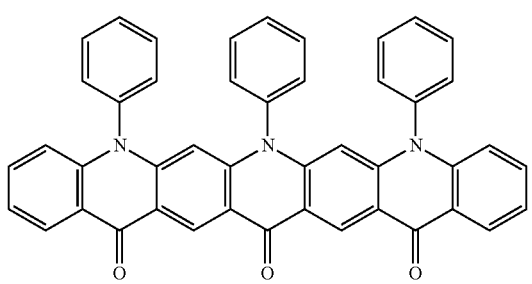
72

73
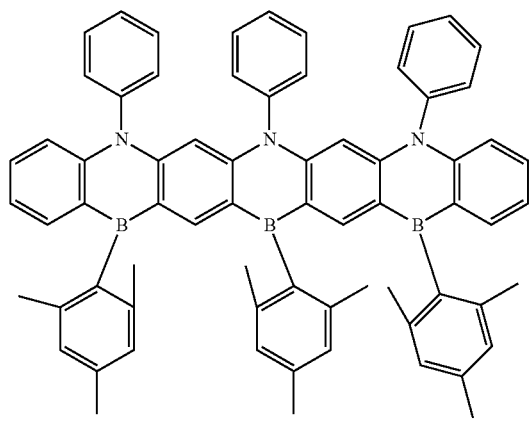
74
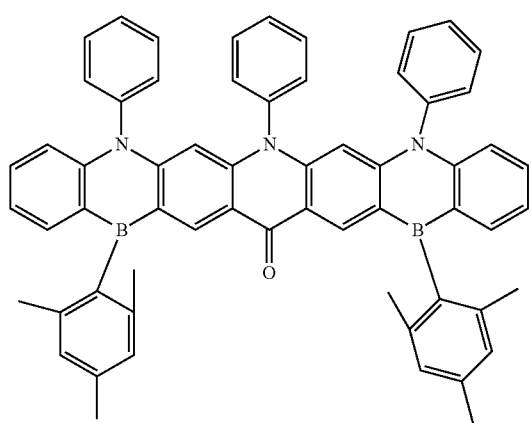
75
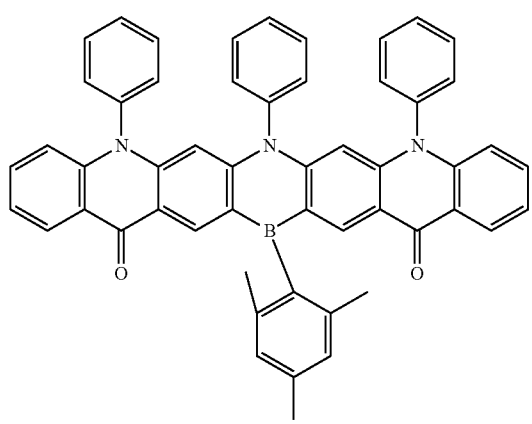
76
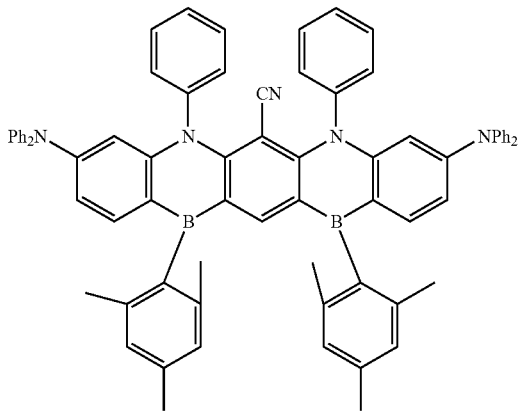
77
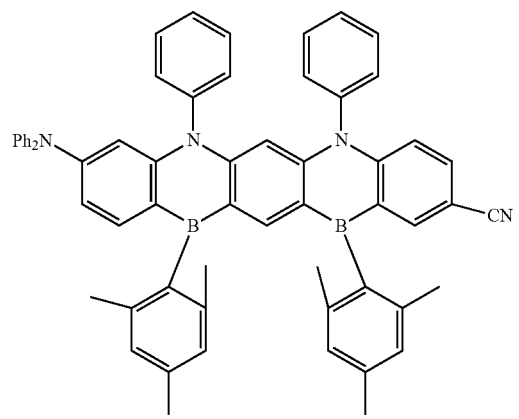
78
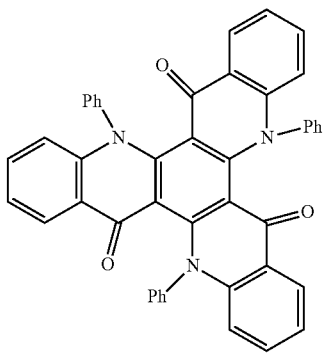
79
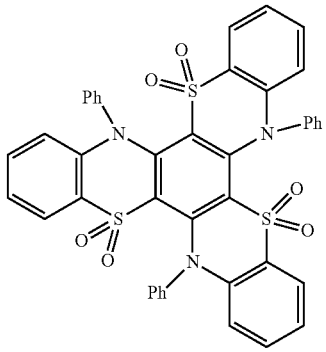

80
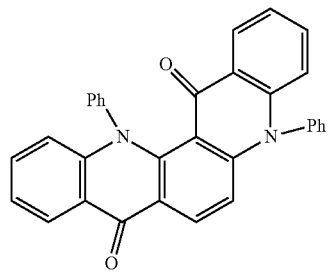
81
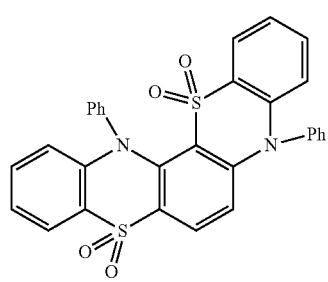
82
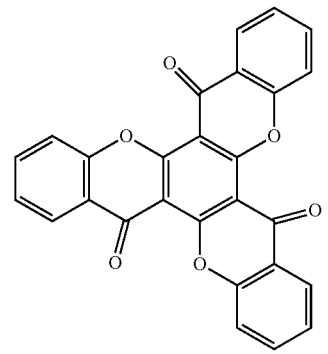
83
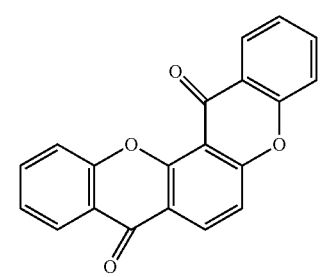
84
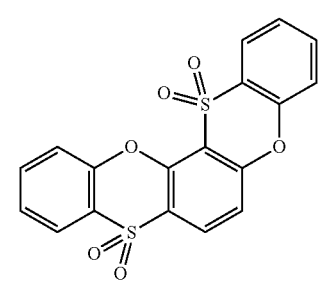
85
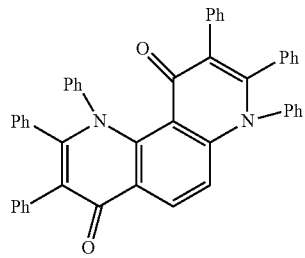
86
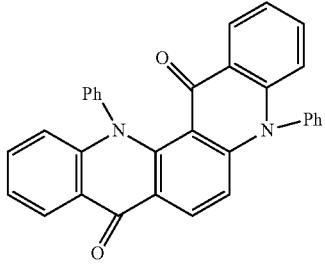
87
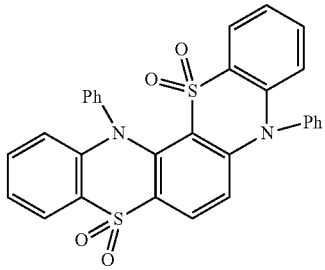
88
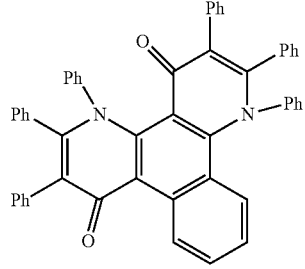
89
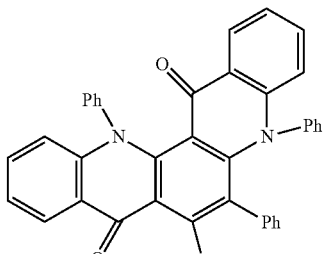
90
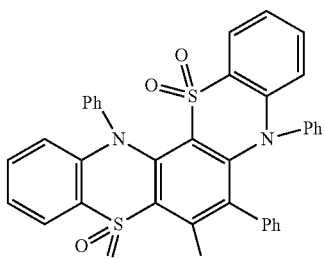

91
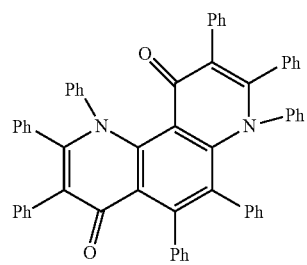
92
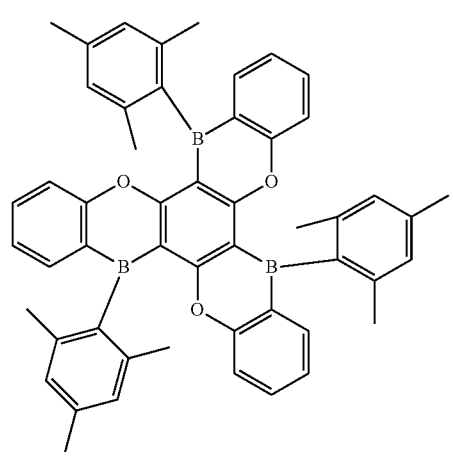
93
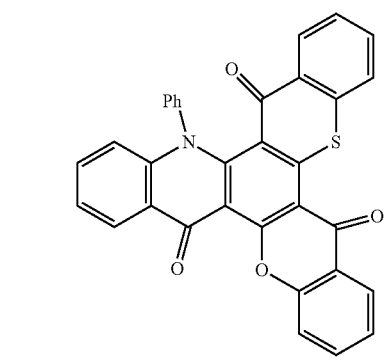
94
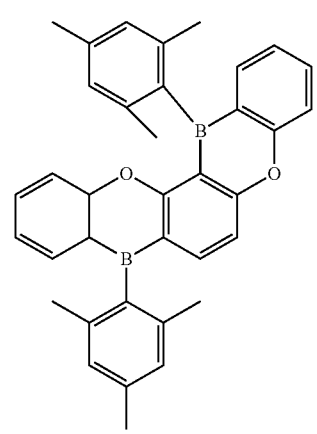
95
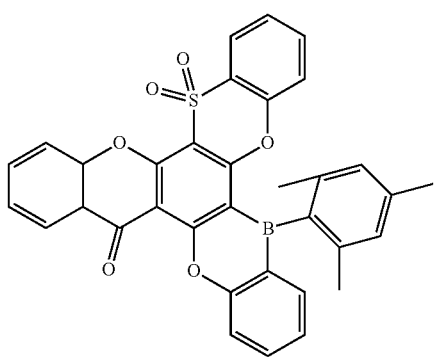
96
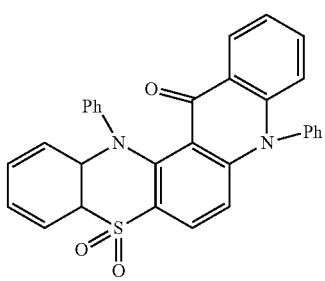
97
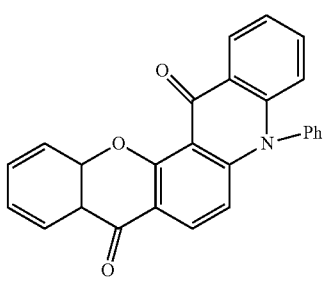
98
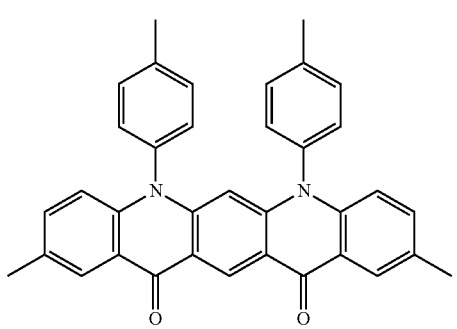

99

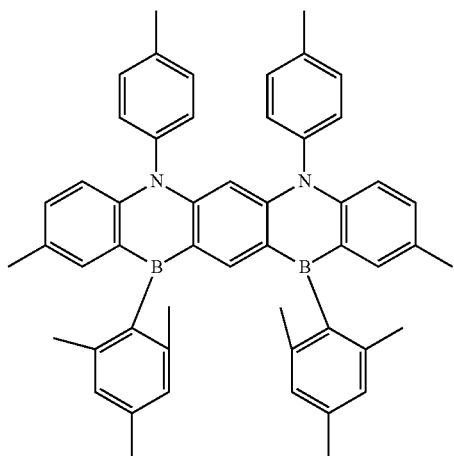

100

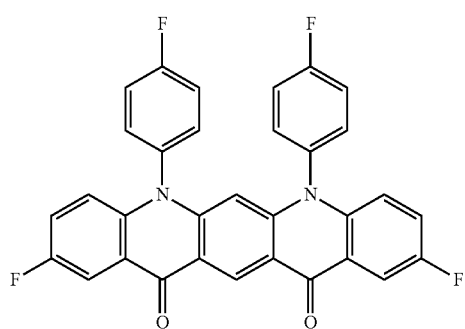

101

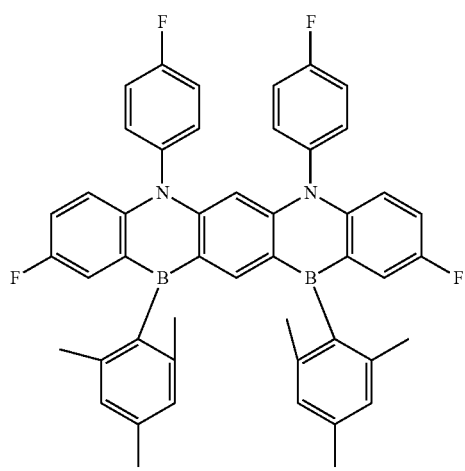

102

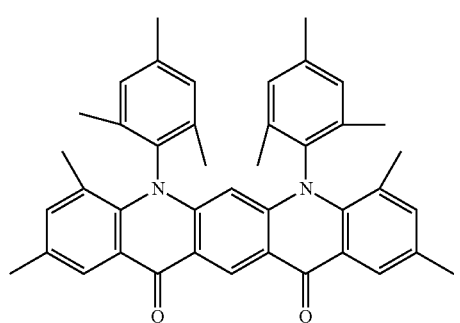

103

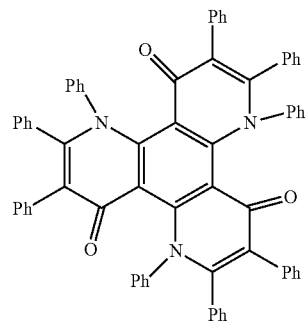

In an embodiment, there is provided an organic electroluminescence device including a first electrode, a hole transport region on the first electrode, an emission layer on the hole transport region, an electron transport region on the emission layer, and a second electrode on the electron transport region, wherein the emission layer includes a polycyclic compound represented by any one among the following Formula 1 to Formula 3, and the first electrode and the second electrode are each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, or a compound of two or more selected from them, a mixture of two or more selected from them, or oxides thereof:

[Formula 1]

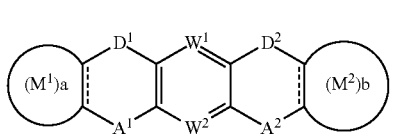

[Formula 2]

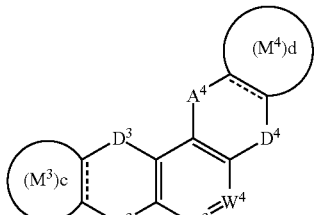

[Formula 3]

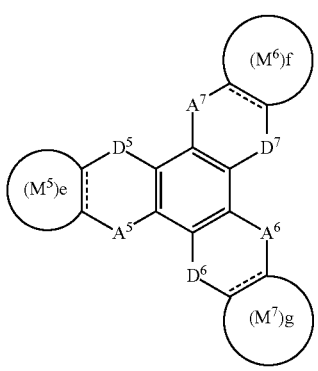

In Formula 1 to Formula 3, $A^1$ to $A^7$ are each independently CO, $BR_1$, $SiR_2R_3$, $GeR_4R_5$, $POR_6$, $PSR_7$, SO, or $SO_2$, $D^1$ to $D^7$ are each independently $NR_8$, O, S, or Se, $W^1$ to $W^4$ are each independently N or $CR_9$, a to g are each independently 0 or 1. In Formula 1 to Formula 3, $M^1$ to $M^7$ are each independently a substituted or unsubstituted aryl group having 6 to 30 ring carbon atoms, or a substituted or unsubstituted heteroaryl group having 2 to 30 ring carbon atoms.

In Formula 1 to Formula 3, $R_1$ to $R_8$ are each independently a hydrogen atom, a deuterium atom, a halogen atom, a cyano group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In Formula 1 to Formula 3, $R_9$ is a hydrogen atom, a deuterium atom, a halogen atom, a cyano group, a phosphine oxide group, a phosphine sulfide group, a carbonyl group, a boron group, a substituted or unsubstituted oxy group, a substituted or unsubstituted thiol group, a substituted or unsubstituted amino group, a substituted or unsubstituted silyl group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In an embodiment, the emission layer may be a delayed fluorescence emission layer including a host and a dopant, and the host may include the polycyclic compound represented by any one among Formula 1 to Formula 3.

In an embodiment, the emission layer may be a phosphorescence emission layer including a host and a dopant, and the host may include the polycyclic compound represented by any one among Formula 1 to Formula 3.

In an embodiment, the polycyclic compound may be at least one among the compounds represented in Compound Group 1.

In an embodiment, there is provided a polycyclic compound represented by any one among Formula 1 to Formula 3:

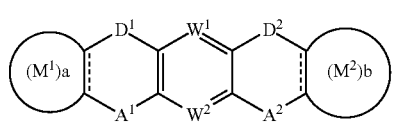
[Formula 1]

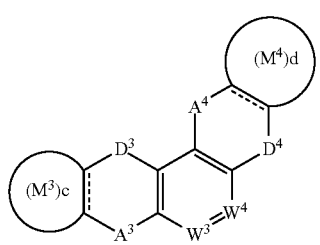
[Formula 2]

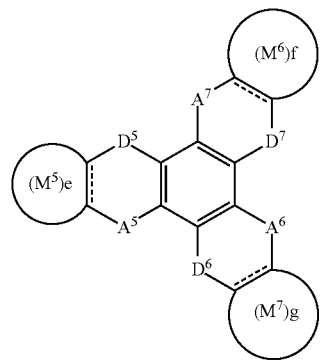
[Formula 3]

In Formula 1 to Formula 3, $A^1$ to $A^7$ are each independently CO, $BR_1$, $SiR_2R_3$, $GeR_4R_5$, $POR_6$, $PSR_7$, SO, or $SO_2$, $D^1$ to $D^7$ are each independently $NR_8$, O, S, or Se, $W^1$ to $W^4$ are each independently N or $CR_9$, and a to g are each independently 0 or 1. In Formula 1 to Formula 3, $M^1$ to $M^7$ are each independently a substituted or unsubstituted aryl group having 6 to 30 ring carbon atoms, or a substituted or unsubstituted heteroaryl group having 2 to 30 ring carbon atoms.

In Formula 1 to Formula 3, $R_1$ to $R_8$ are each independently a hydrogen atom, a deuterium atom, a halogen atom, a cyano group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In Formula 1 to Formula 3, $R_9$ is a hydrogen atom, a deuterium atom, a halogen atom, a cyano group, a phosphine oxide group, a phosphine sulfide group, a carbonyl group, a boron group, a substituted or unsubstituted oxy group, a substituted or unsubstituted thiol group, a substituted or unsubstituted amino group, a substituted or unsubstituted silyl group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In an embodiment, Formula 1 to Formula 3 may be represented by the following Formula 1-1 to Formula 1-3, respectively:

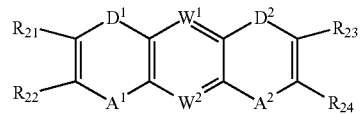
[Formula 1-1]

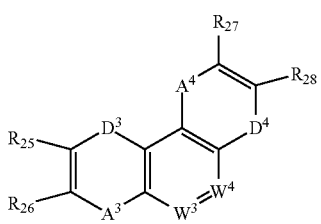
[Formula 1-2]

[Formula 1-3]

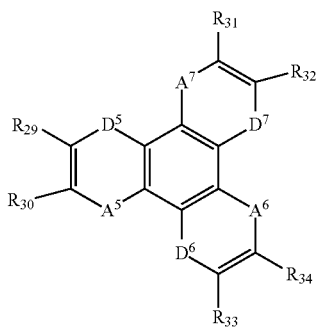

In Formulae 1-1 to 1-3, $R_{21}$ to $R_{34}$ are each independently a hydrogen atom, a deuterium atom, a halogen atom, a cyano group, a phosphine oxide group, a phosphine sulfide group, a silyl group, a carbonyl group, a boron group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and $A^1$ to $A^7$, $D^1$ to $D^7$, and $W^1$ to $W^4$ are the same as defined in Formula 1 to Formula 3.

In an embodiment, Formula 1 to Formula 3 may be represented by the following Formula 2-1 to Formula 2-3, respectively:

[Formula 2-1]

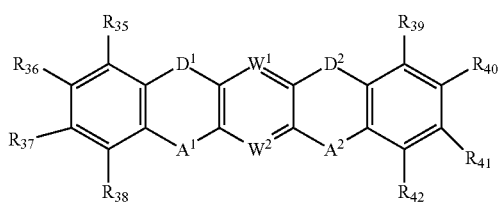

[Formula 2-2]

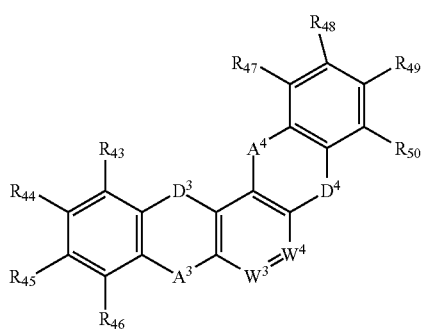

[Formula 2-3]

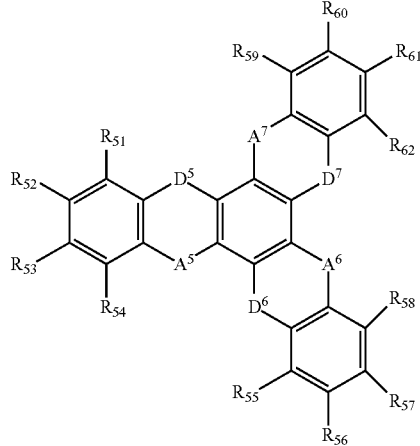

In Formula 2-1 to Formula 2-3, $R_{35}$ to $R_{62}$ are each independently a hydrogen atom, a deuterium atom, a halogen atom, a cyano group, a phosphine oxide group, a phosphine sulfide group, a silyl group, a carbonyl group, a boron group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and $A^1$ to $A^7$, $D^1$ to $D^7$, and $W^1$ to $W^4$ are the same as defined in Formula 1 to Formula 3.

In an embodiment, in Formula 1, $D^1$ and $D^2$ may be the same and $A^1$ and $A^2$ may be the same, and in Formula 3, $D^5$ to $D^7$ may be the same and $A^5$ to $A^7$ may be the same.

In an embodiment, the polycyclic compound represented by any one among Formula 1 to Formula 3 may be a material for emitting thermally activated delayed fluorescence.

In an embodiment, the lowest triplet excitation energy of the polycyclic compound represented by any one among Formula 1 to Formula 3 may be about 3.0 eV or less.

In an embodiment, the polycyclic compound represented by any one among Formula 1 to Formula 3 may be a phosphorescence host material.

In an embodiment, the polycyclic compound represented by any one among Formula 1 to Formula 3 may be at least one among the compounds represented in Compound Group 1

BRIEF DESCRIPTION OF THE DRAWINGS

Features will become apparent to those of skill in the art by describing in detail example embodiments with reference to the attached drawings in which.

DETAILED DESCRIPTION

Figure 1:
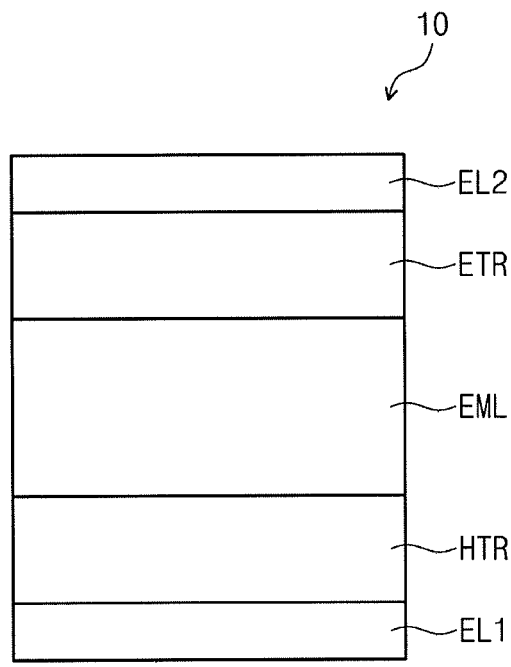
FIG. 1 is a cross-sectional view schematically illustrating an organic electroluminescence device according to an example embodiment.

Example embodiments will now be described more fully hereinafter with reference to the accompanying drawings;

however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

It will be understood that, although the terms first, second, etc. may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof.

It will also be understood that when a layer, a film, a region, a plate, etc. is referred to as being "on" or "above" another part, it can be "directly on" the other part, or intervening layers may also be present. On the contrary, it will also be understood that when a layer, a film, a region, a plate, etc. is referred to as being "under" or "below" another part, it can be "directly under" the other part, or intervening layers may also be present. In addition, it will also be understood that when an element is referred to as being "on" another part, it can be on or under the other part.

Hereinafter, an organic electroluminescence device according to an example embodiment will be explained referring to drawings.

Figure 2:
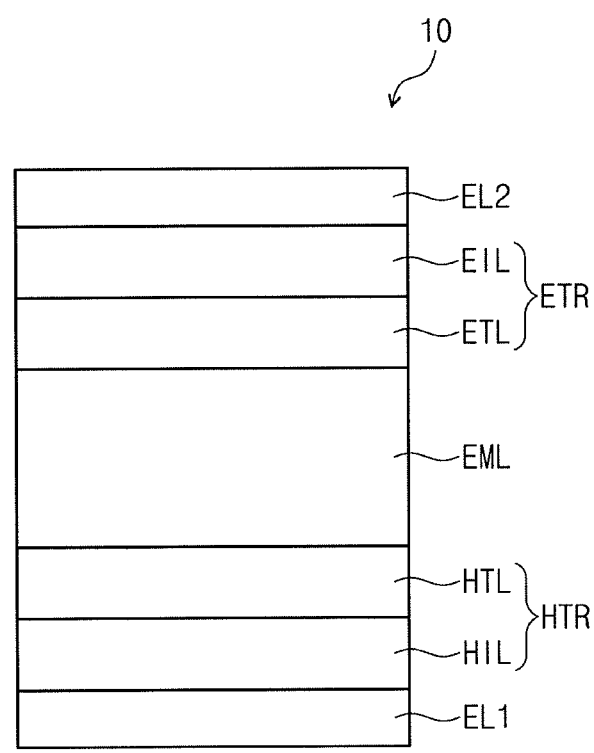
FIG. 2 is a cross-sectional view schematically illustrating an organic electroluminescence device according to an example embodiment.
Figure 3:
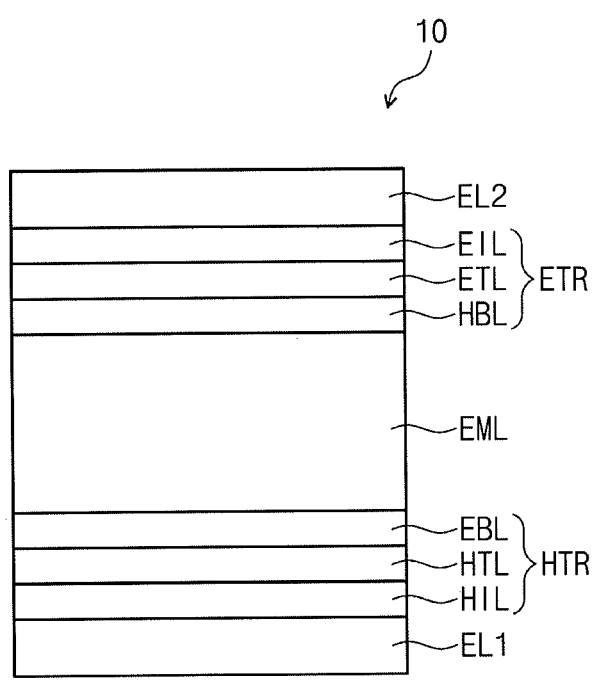
FIG. 3 is a cross-sectional view schematically illustrating an organic electroluminescence device according to an example embodiment.

FIGS. 1 to 3 are cross-sectional views schematically illustrating organic electroluminescence devices according to embodiments. Referring to FIGS. 1 to 3, an organic electroluminescence device 10 according to an example embodiment may include a first electrode EL1, a hole transport region HTR, an emission layer EML, an electron transport region ETR and a second electrode EL2, laminated one by one.

The first electrode EL1 and the second electrode EL2 may be disposed opposite from each other, and a plurality of organic layers may be disposed between the first electrode EL1 and the second electrode EL2. The plurality of the organic layers may include a hole transport region HTR, an emission layer EML, and an electron transport region ETR. The organic electroluminescence device 10 according to an example embodiment may include the polycyclic compound according to an example embodiment in the emission layer EML.

Compared to FIG. 1, FIG. 2 shows the cross-sectional view of an organic electroluminescence device 10 according to an example embodiment, wherein a hole transport region HTR includes a hole injection layer HIL and a hole transport layer HTL, and an electron transport region ETR includes an electron injection layer EIL and an electron transport layer ETL. In addition, FIG. 3 shows a hole transport region HTR that includes a hole injection layer HIL, a hole transport layer HTL, and an electron blocking layer EBL, and an electron transport region ETR that includes an electron injection layer EIL, an electron transport layer ETL, and a hole blocking layer HBL.

The first electrode EL1 may have conductivity and may be formed using a metal alloy or a conductive compound. The first electrode EL1 may be an anode. The first electrode EL1 may be a pixel electrode. The first electrode EL1 may be a transmissive electrode, a transflective electrode, or a reflective electrode. When the first electrode EL1 is the transmissive electrode, the first electrode EL1 may be formed using a transparent metal oxide such as indium tin oxide (ITO), indium zinc oxide (IZO), zinc oxide (ZnO), and indium tin zinc oxide (ITZO). When the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The first electrode EL1 may have a structure including a plurality of layers including a reflective layer or a transflective layer formed using the above materials, and a transmissive conductive layer formed using ITO, IZO, ZnO, or ITZO. For example, the first electrode EL1 may include a plurality of layers of ITO/Ag/ITO.

The thickness of the first electrode EL1 may be from about 1,000 to about 10,000 Å, for example, from about 1,000 to about 3,000 Å.

The hole transport region HTR may be provided on the first electrode EL1. The hole transport region HTR may include at least one of a hole injection layer HIL, a hole transport layer HTL, a hole buffer layer, or an electron blocking layer EBL.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer such as a hole injection layer HIL, or a hole transport layer HTL, and may have a structure of a single layer formed using a hole injection material and a hole transport material. In another implementation, the hole transport region HTR may have a structure of a single layer formed using a plurality of different materials, or a structure laminated from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris (3-methylphenylphenylamino) triphenylamine (m-MTDATA), 4,4', 4"-tris (N,N-diphenylamino) triphenylamine (TDATA), 4,4', 4"-tris (N,-(2-naphthyl)-N-phenylamino)-triphenylamine (2-TNATA), poly (3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di (1-naphthalene-1-yl)-N,N'-diphenyl-benzidine (NPB), triphenylamine-containing polyether ketone (TPAPEK), 4-isopropyl-4'-methyldiphenyliodonium tetrakis (pentafluorophenyl) borate, dipyrazino [2,3-f: 2',3'-h] quinoxaline-2,3,6,7,10,11-hexacarbonitrile (HAT-CN), etc.

The hole transport layer HTL may include, for example, carbazole derivatives such as N-phenyl carbazole and polyvinyl carbazole, fluorene-based derivatives, N,N'-bis(3-methylphenyl)-N,N'-diphenyl-[1,1-biphenyl]-4,4'-diamine (TPD), triphenylamine-based derivatives such as 4,4',4"-tris (N-carbazolyl) triphenylamine (TCTA), N,N'-di (1-naphthalene-1-yl)-N,N'-diphenyl-benzidine (NPB), 4,4'-cyclohexylidene bis [N,N-bis(4-methylphenyl) benzenamine] (TAPC), 4,4'-bis [N,N'-(3-tolyl) amino]-3,3'-dimethylbiphenyl (HMTPD), 1,3-bis(N-carbazolyl) benzene (mCP), etc.

The thickness of the hole transport region HTR may be from about 100 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. When the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may include a charge generating material, in addition to the above-described materials, to improve conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds. Examples of the p-dopant may include quinone derivatives such as tetracyanoquinodimethane (TCNQ) and 2,3,5,6-tetrafluoro-7,7,8,8-tetracyanoquinodi-methane (F4-TCNQ), and metal oxides such as tungsten oxide and molybdenum oxide.

As described above, the hole transport region HTR may include at least one of a hole buffer layer or an electron blocking layer EBL in addition to the hole injection layer HIL and the hole transport layer HTL. The hole buffer layer may compensate a resonance distance according to the wavelength of light emitted from the emission layer EML and increase light emission efficiency. Materials included in the hole transport region HTR may be used as materials included in the hole buffer layer. The electron blocking layer EBL may prevent electron injection from an electron transport region ETR to a hole transport region HTR.

The emission layer EML may be provided on the hole transport region HTR. The emission layer EML may have a thickness of, for example, about 100 Å to about 1,000 Å or about 100 Å to about 300 Å. The emission layer EML may have a single layer formed using a single material, a single layer formed using a plurality of different materials, or a multilayer structure having a plurality of layers formed using a plurality of different materials.

In the organic electroluminescence device 10 according to an example embodiment, the emission layer EML may include a condensed polycyclic compound of three or more six-membered (e.g., hexagonal) rings. At least two six-membered rings among the three or more six-membered rings of the polycyclic compound may include an electron donor moiety and an electron acceptor moiety that face each other. The electron donor moiety and the electron acceptor moiety may be ring forming parts forming a six-membered ring. Two or more six-membered rings including the electron donor moiety and the electron acceptor moiety may not be adjacent to each other. That is, the six-membered rings including an electron donor moiety and an electron acceptor moiety in a polycyclic compound may not be bonded in neighbored positions. For example, in the condensed polycyclic compound, a ring may be formed by including a third six-membered ring between six-membered rings including the separately provided electron donor moiety and electron acceptor moiety in the condensed polycyclic compound. Each of three or more six-membered rings may be an aliphatic hydrocarbon ring, an aromatic hydrocarbon ring, an aliphatic heterocycle, or an aromatic heterocycle.

The polycyclic compound may include three or more six-membered rings, and two or more six-membered rings among the six-membered rings may be a heterocycle including at least one heteroatom. For example, the polycyclic compound may include in a core part, a tricyclic heterocycle compound obtained by condensing three six-membered rings, a tetracyclic heterocycle compound obtained by condensing four rings, a pentacyclic heterocycle compound obtained by condensing five rings, a hexacyclic heterocycle compound obtained by condensing six rings, or a heptacyclic heterocycle compound obtained by condensing seven rings.

In the polycyclic compound, the electron donor moiety may include an amine group, an oxygen atom (O), a sulfur atom(S), or a selenium atom (Se, and the electron acceptor moiety may include a carbonyl group, a boron group, a silyl group, a phosphine oxide group, a phosphine sulfide group, a sulfoxide group, or a sulfur dioxide group.

The heterocycle includes an aliphatic heterocycle including at least one heteroatom, and an aromatic heterocycle including at least one heteroatom.

The term "substituted or unsubstituted" may corresponds to substituted or unsubstituted with at least one substituent selected from the group consisting of a deuterium atom, a halogen atom, a cyano group, a nitro group, an amino group, a silyl group, a boron group, an alkyl group, an alkenyl group, an alkoxy group, an aryl group, and a heterocyclic group. In addition, each of the illustrated substituents may be substituted or unsubstituted. For example, a biphenyl group may be interpreted as an aryl group or a phenyl group substituted with a phenyl group.

The halogen atom may be a fluorine atom, a chlorine atom, a bromine atom or an iodine atom.

The alkyl may be a linear, branched or cyclic type. The carbon number of the alkyl may be 1 to 30, 1 to 20, 1 to 10, or 1 to 5. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

The alkenyl may be a linear or branched chain. The number of carbon is not specifically limited, but may be 2 to 30, 2 to 20, or 2 to 10. Examples of the alkenyl group may include a vinyl group, a 1-butenyl group, a 1-pentenyl group, a 1,3-butadienyl group, a styrenyl group, a styrylvinyl group, etc.

The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be a monocycle or a polycycle. The aryl group means an optional functional group or substituent derived from an aromatic hydrocarbon ring. The aryl group may be a monocyclic aryl group or a polycyclic aryl group. The carbon number for forming a ring in the aryl group may be, 6 to 60, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc.

The fluorenyl group may be substituted, and two substituents may be combined with each other to form a spiro structure. Examples of the case where the fluorenyl group is substituted are as follows.

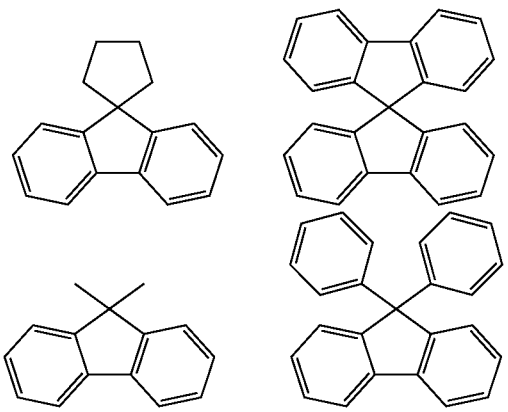

The heteroaryl may be a heteroaryl group including at least one of B, O, N, P, Si or S as a heteroatom. When the heteroaryl group includes two or more heteroatoms, the two or more heteroatoms may be the same or different. The heteroaryl may be monocyclic heteroaryl or polycyclic heteroaryl. The carbon number for forming a ring of the heteroaryl may be 2 to 30, 2 to 20, or 2 to 10. Examples of the heteroaryl may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, isooxazole, thiadiazole, phenothiazine, dibenzosilole, dibenzofuran, etc.

The silyl group includes an alkyl silyl group and an aryl silyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc.

The carbon number of the amino group is not specifically limited, but may be 1 to 30. The amino group may include an alkyl amino group and an aryl amino group. Examples of the amino group include a methylamino group, a dimethylamino group, a phenylamino group, a diphenylamino group, a naphthylamino group, a 9-methyl-anthracenylamino group, a triphenylamino group, etc.

The boron group includes an alkyl boron group and an aryl boron group. Examples of the boron group includes a trimethylboron group, a triethylboron group, a t-butyldimethylboron group, a triphenylboron group, a diphenylboron group, a phenylboron group, etc.

A dotted line (---) represents a part where a double bond is optionally applied. That is, a part represented by the dotted line (---) may be a double bond or a single bond part. Also, "---" means a connecting part.

The polycyclic compound included in the emission layer EML of an organic electroluminescence device 10 according to an example embodiment may be represented by any one among the following Formula 1 to Formula 3:

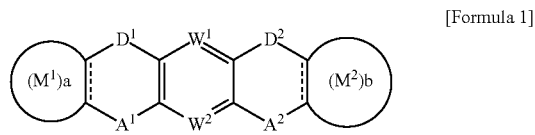

[Formula 1]

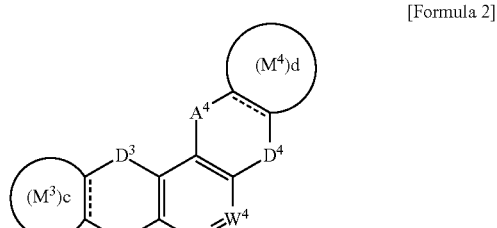

[Formula 2]

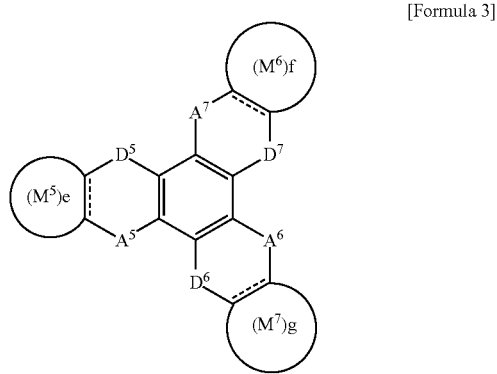

[Formula 3]

In Formula 1 to Formula 3, $A^1$ to $A^7$ may each independently be CO, $BR_1$, $SiR_2R_3$, $GeR_4R_5$, $POR_6$, $PSR_7$, SO, or $SO_2$, and $D^1$ to $D^7$ may each independently be $NR_8$, O, S, or Se. In Formula 1 to Formula 3, $A^1$ to $A^7$ may be electron acceptor moieties, and $D^1$ to $D^7$ may be electron donor moieties. That is, in an embodiment, the polycyclic compound may include at least two six-membered rings that include both an electron donor moiety and an electron acceptor moiety. The six-membered rings including both an electron donor moiety and an electron acceptor moiety may be condensed at not a neighboring position to each other.

In Formula 1, $D^1$ and $D^2$ may be the same, and $A^1$ and $A^2$ may be the same. In Formula 3, all $D^5$ to $D^7$ may be the same, and all $A^5$ to $A^7$ may be the same.

Meanwhile, $A^1$ to $A^7$ in the polycyclic compounds represented by Formula 1 to Formula 3 may be represented by the following Formula 4:

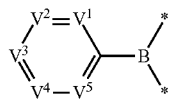

[Formula 4]

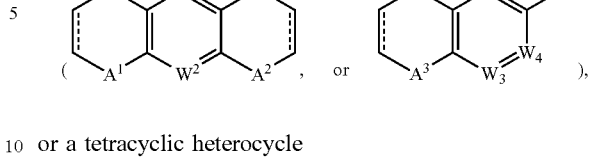

or a tetracyclic heterocycle

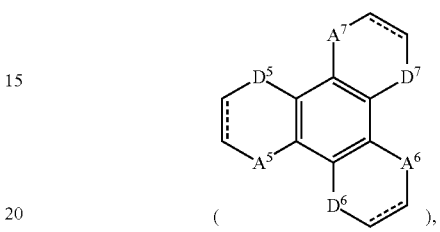

In Formula 4, $V^1$ to $V^5$ may each independently be N or $CR_{10}$, and at least one among $V^1$ to $V^5$ may be $CR_{11}$. $R_{10}$ may be a hydrogen atom, a deuterium atom, a halogen atom, a cyano group, a phosphine oxide group, a phosphine sulfide group, a carbonyl group, a boron group, a substituted or unsubstituted oxy group, a substituted or unsubstituted thiol group, a substituted or unsubstituted amino group, a substituted or unsubstituted silyl group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

$R_{11}$ may be a cyano group, a substituted or unsubstituted oxy group, a substituted or unsubstituted thiol group, a substituted or unsubstituted amino group, a substituted or unsubstituted silyl group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In Formula 1 to Formula 3, $R_1$ to $R_8$ may each independently be a hydrogen atom, a deuterium atom, a halogen atom, a cyano group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

For example, $D^1$ to $D^7$ may be $NR_8$, and in this case, $R_8$ may be a substituted or unsubstituted phenyl group. For example, $R_8$ may be an unsubstituted phenyl group.

In Formula 1 and Formula 2, $W^1$ to $W^4$ may each independently be N or $CR_9$, and $R_9$ may be a hydrogen atom, a deuterium atom, a halogen atom, a cyano group, a phosphine oxide group, a phosphine sulfide group, a carbonyl group, a boron group, a substituted or unsubstituted oxy group, a substituted or unsubstituted thiol group, a substituted or unsubstituted amino group, a substituted or unsubstituted silyl group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In Formula 1 to Formula 3, a to g may each independently be 0 or 1. $M^1$ to $M^7$ may each independently be a substituted or unsubstituted aryl group having 6 to 30 ring carbon atoms, or a substituted or unsubstituted heteroaryl group having 2 to 30 ring carbon atoms. For example, $M^1$ to $M^7$ may each independently be a substituted or unsubstituted phenyl group.

In Formula 1 to Formula 3, when a to g are 0, $M^1$ to $M^7$, which are six-membered rings, may not be condensed to a tricyclic heterocycle which corresponds to a core part. When a to f are 1, $M^1$ to $M^7$, which are six-membered rings, may be condensed with a tricyclic heterocycle or a tetracyclic heterocycle, that corresponds to a core part to form a pentacyclic heterocycle or a heptacyclic heterocycle. Meanwhile, a and b may each independently be 0 or 1, c and d may each independently be 0 or 1, and e, f and g may each independently be 0 or 1. For example, in Formula 1, both a and b may be 0 or 1, in Formula 2, both c and d may be 0 or 1, and in Formula 3, both e,f and g may be 0 or 1.

The polycyclic compound may be represented by any one among Formula 1-1 to Formula 1-3, respectively. Formula 1-1 to Formula 1-3 represent Formula 1 to Formula 3 where a to g are 0, respectively.

[Formula 1-1]

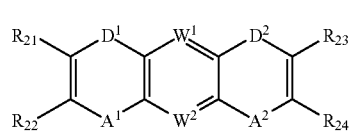

[Formula 1-2]

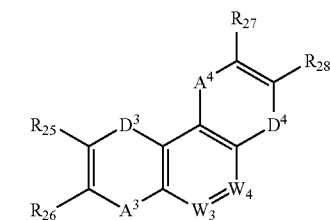

[Formula 1-3]

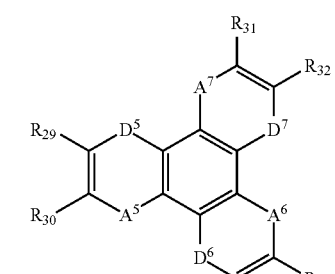

In Formulae 1-1 to 1-3, $R_{21}$ to $R_{34}$ may each independently be a hydrogen atom, a deuterium atom, a halogen atom, a cyano group, a phosphine oxide group, a phosphine sulfide group, a silyl group, a carbonyl group, a boron group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In Formula 1-1 to Formula 1-3, with respect to $A^1$ to $A^7$, $D^1$ to $D^7$, and $W^1$ to $W^4$, the same explanation referring to Formula 1 to Formula 3 may be applied.

In Formula 1-1, $D^1$ and $D^2$ may be the same, and $A^1$ and $A^2$ may be the same. In Formula 1-3, $D^5$ to $D^7$ may be the same, and $A^5$ to $A^7$ may be the same.

The polycyclic compound may be represented by any one among Formula 2-1 to Formula 2-3. Formula 2-1 to Formula 2-3 represent Formula 1 to Formula 3 where a to g are 1, respectively.

halogen atom, a cyano group, a phosphine oxide group, a phosphine sulfide group, a silyl group, a carbonyl group, a boron group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

In Formula 2-1 to 2-3, with respect to $A^1$ to $A^7$, $D^1$ to $D^7$, and $W^1$ to $W^4$, the same explanation referring to Formula 1 to Formula 3 may be applied.

In Formula 2-1, $D^1$ and $D^2$ may be the same, and $A^1$ and $A^2$ may be the same. In Formula 2-3, $D^5$ to $D^7$ may be the same and $A^5$ to $A^7$ may be the same.

In the organic electroluminescence device 10 according to an example embodiment, the emission layer EML may include at least one compound among the compounds represented in the following Compound Group 1:

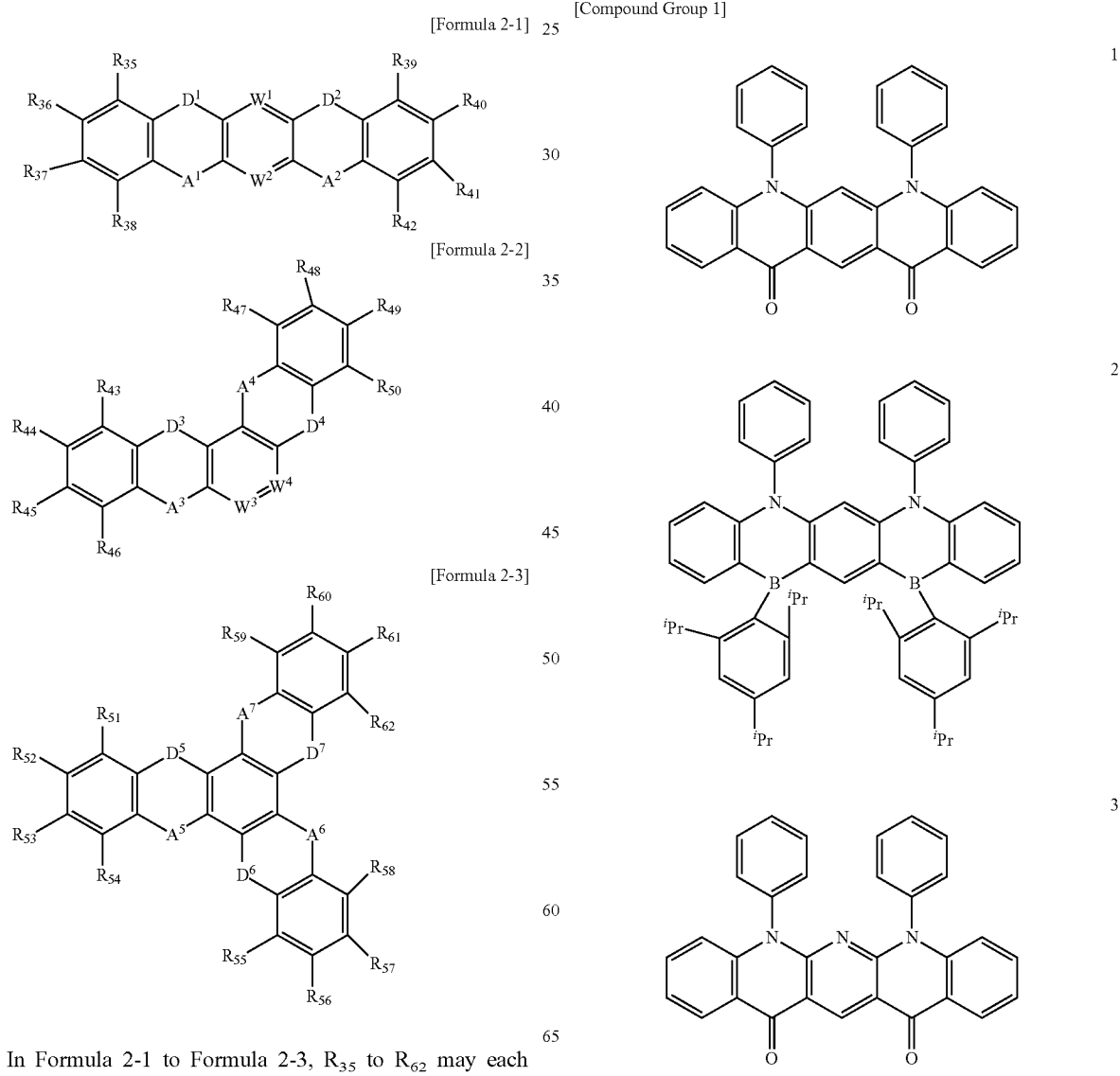

4
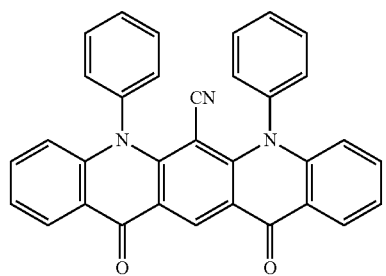
5
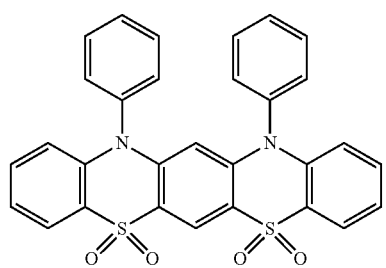
6
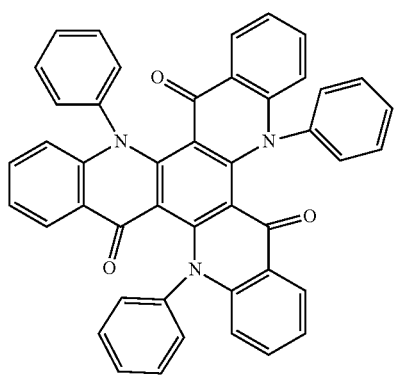
7
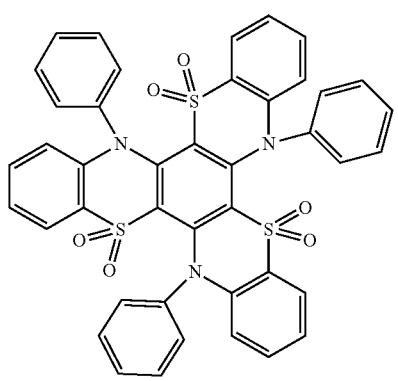
8
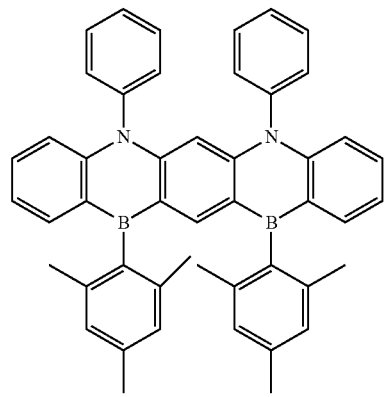
9
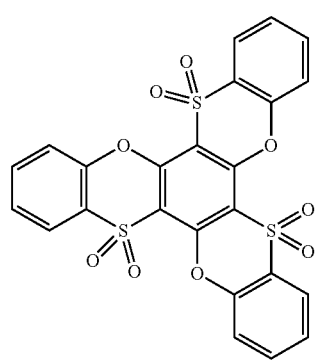
10
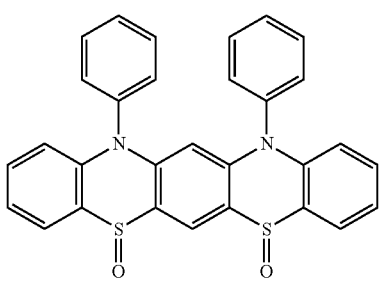
11
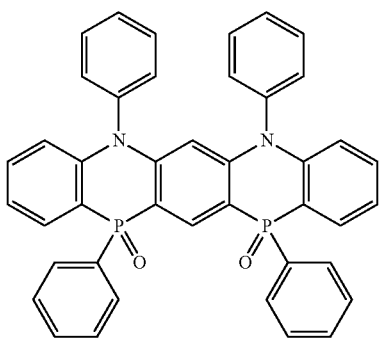

12
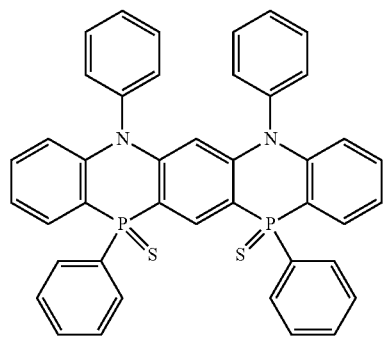
13
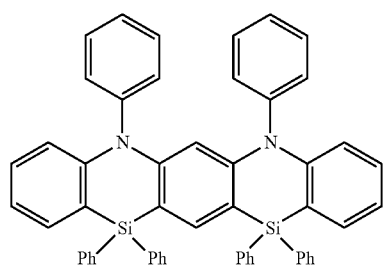
14
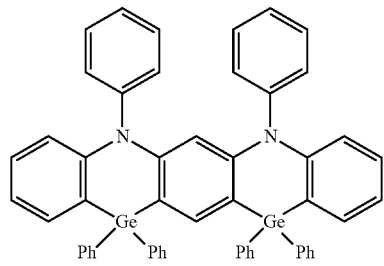
15
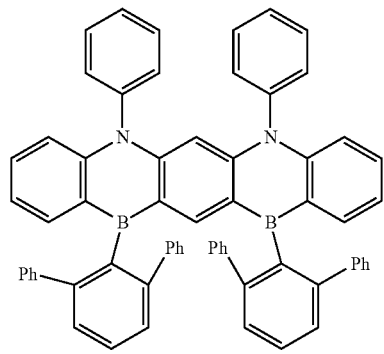
16
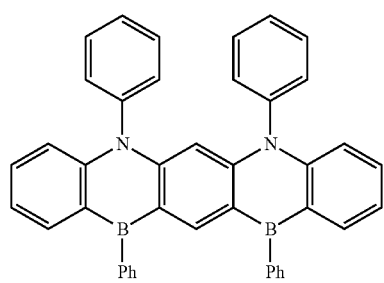
17
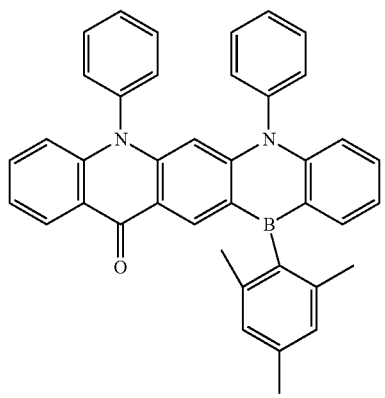
18
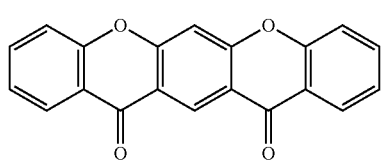
19
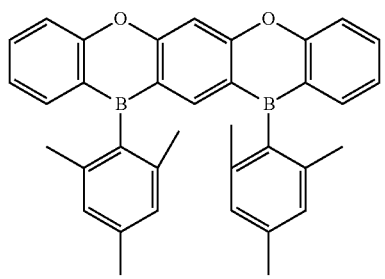
20
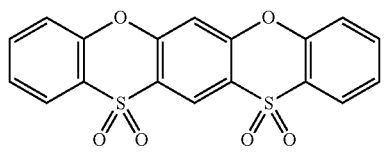
21
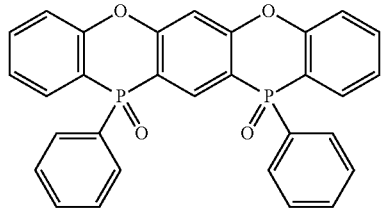
22
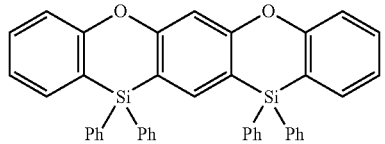
23
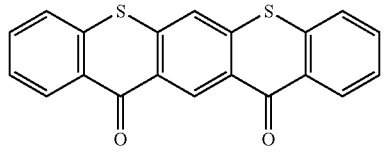

24
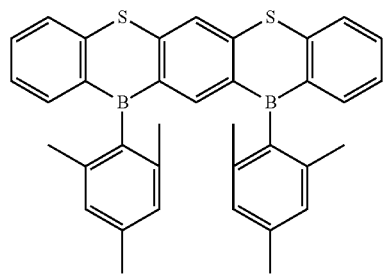
25
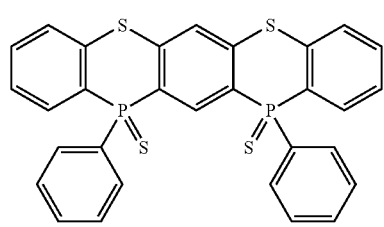
26
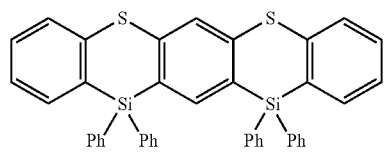
27
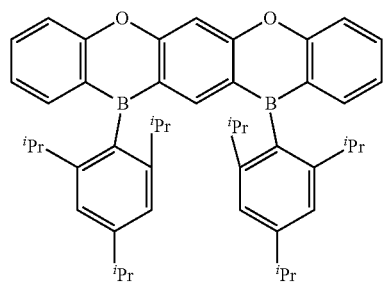
28
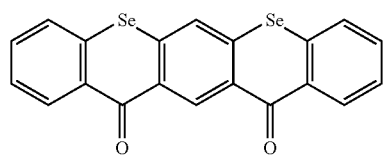
29
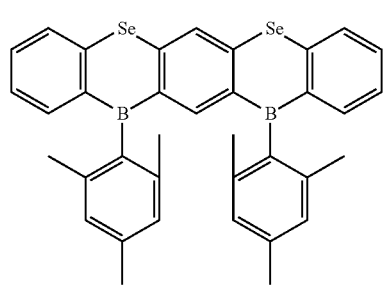
30
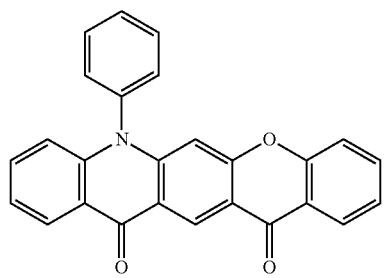
31
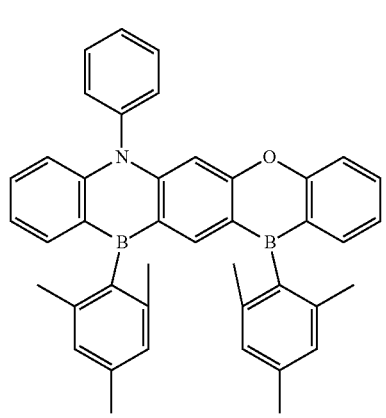
32
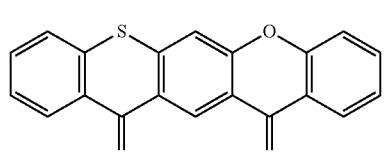
33
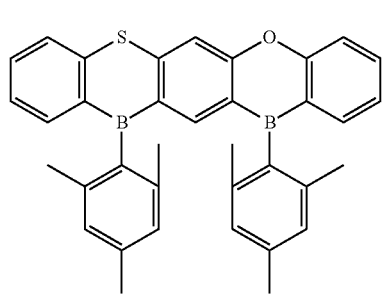
34
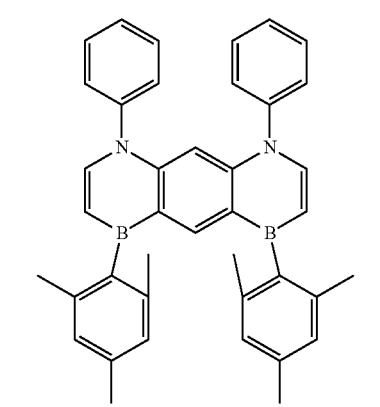

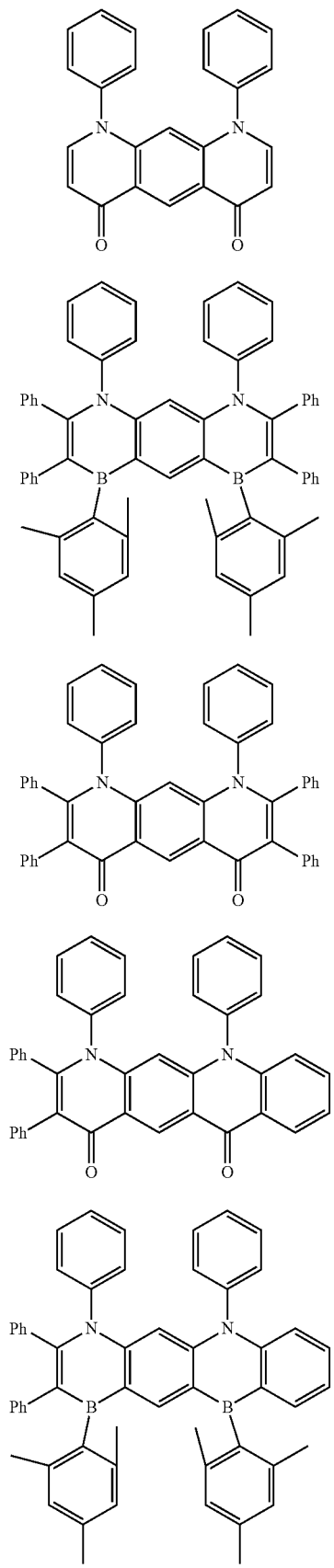
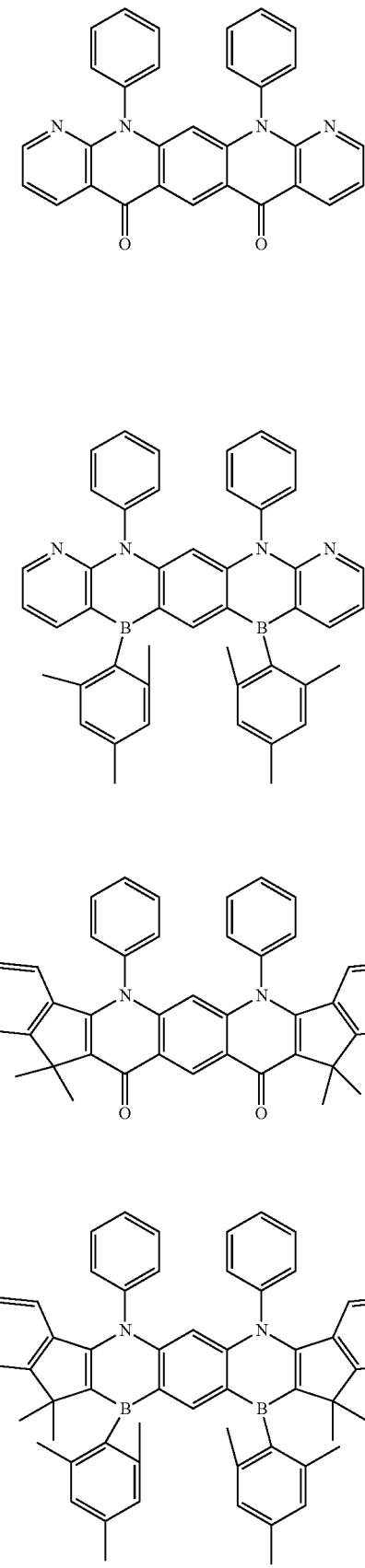

44
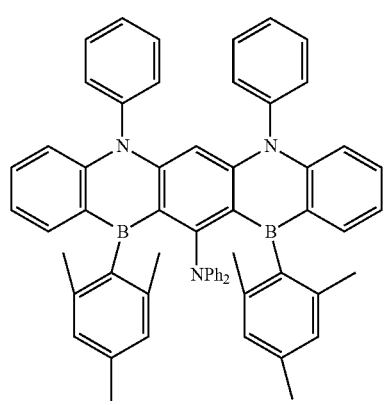
45
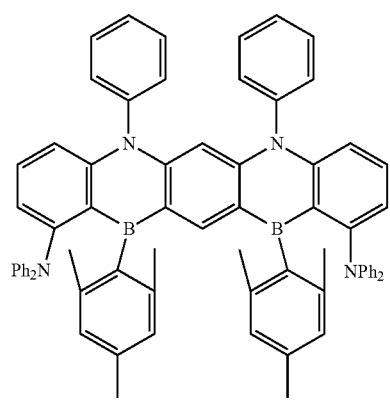
46
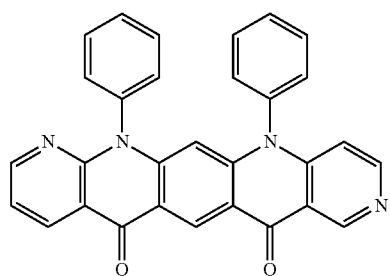
47
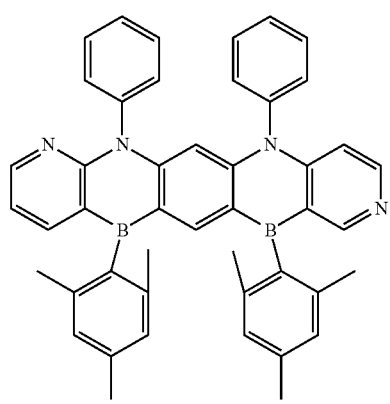
48
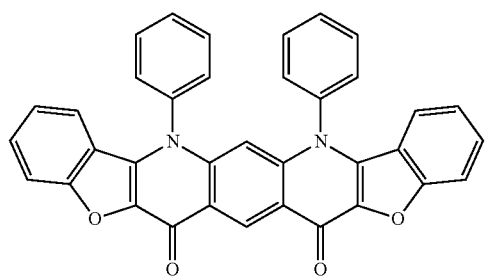
49
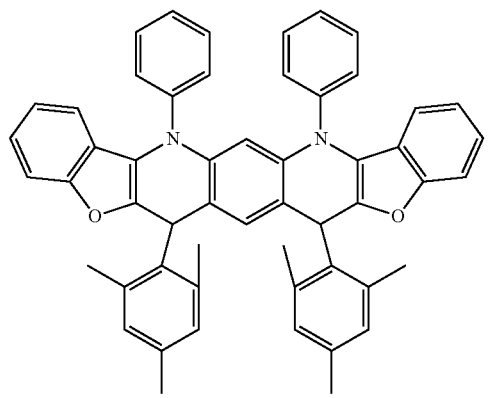
50
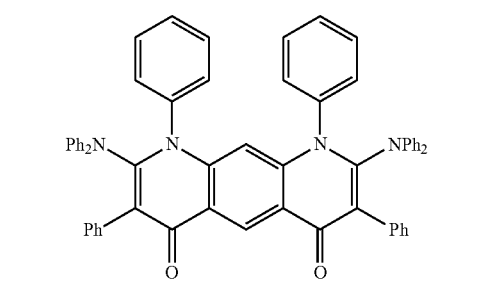
51
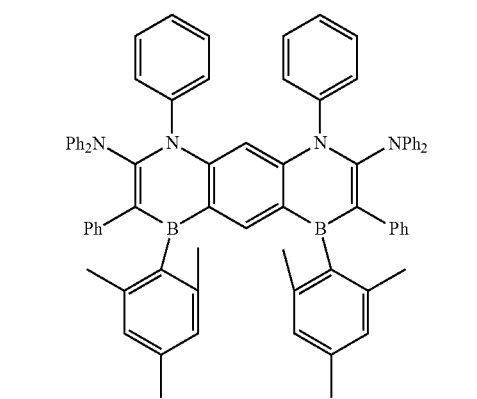
52
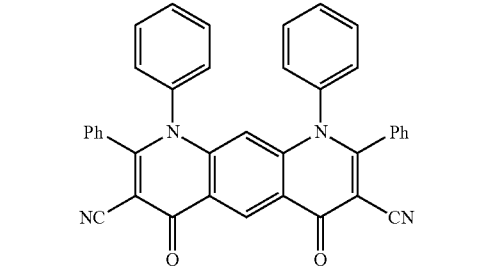

53
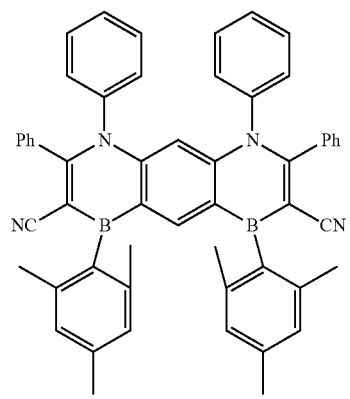
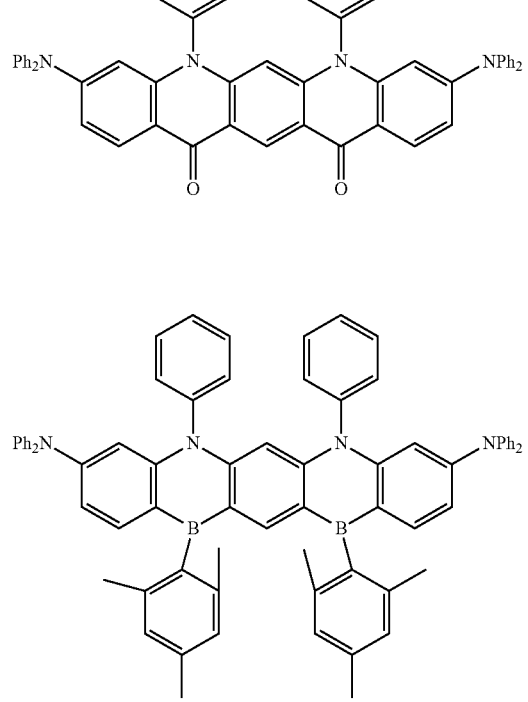
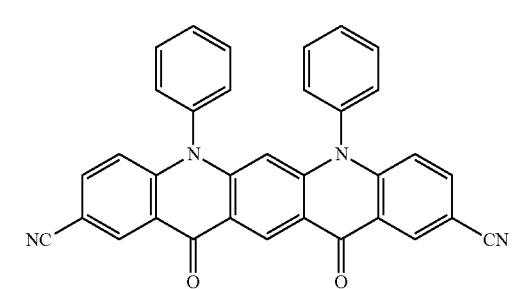
54
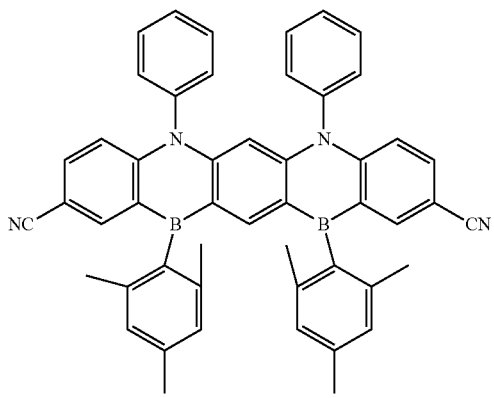
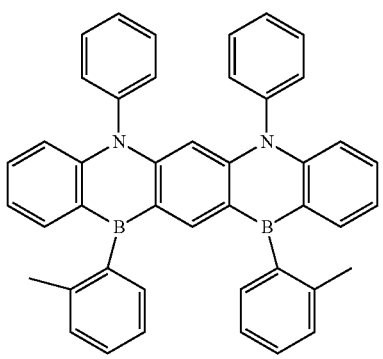
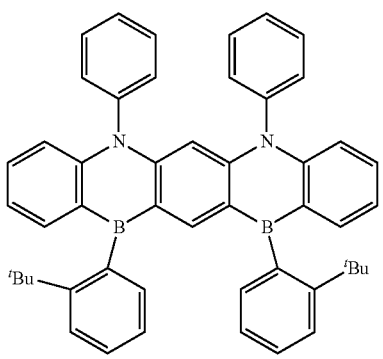
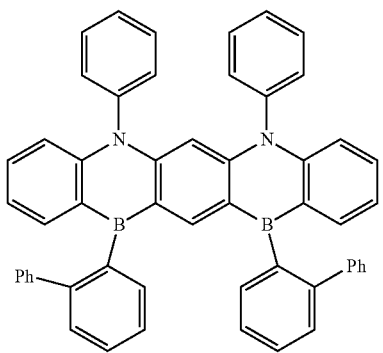

61
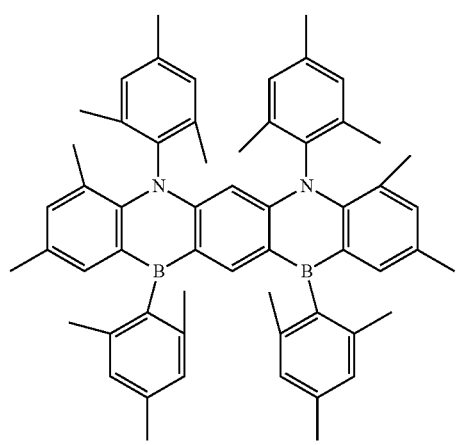
62
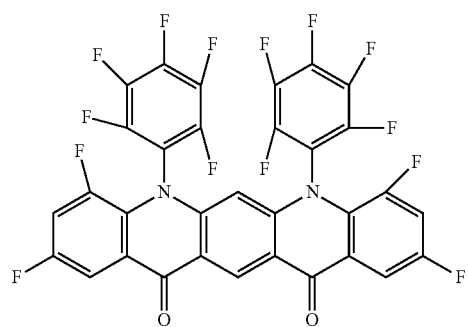
63
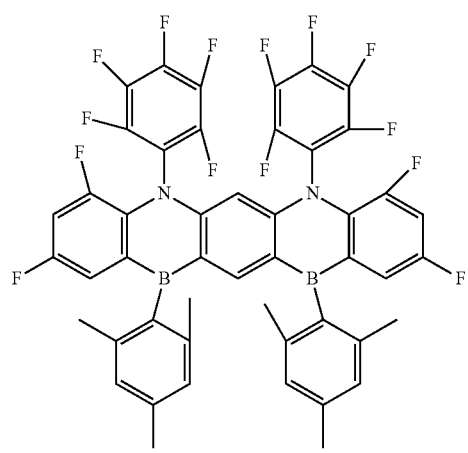
64
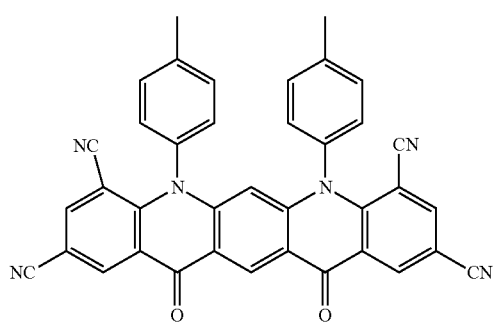
65
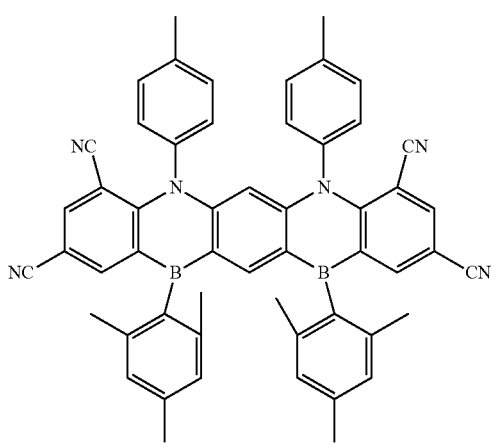
66
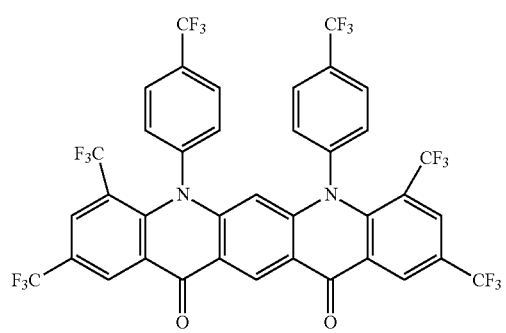
67
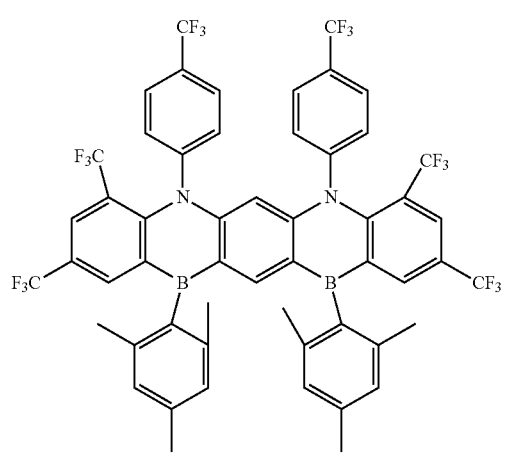
68
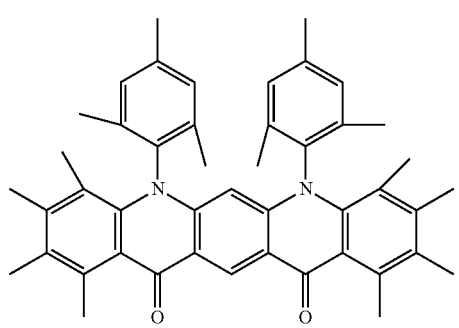

69
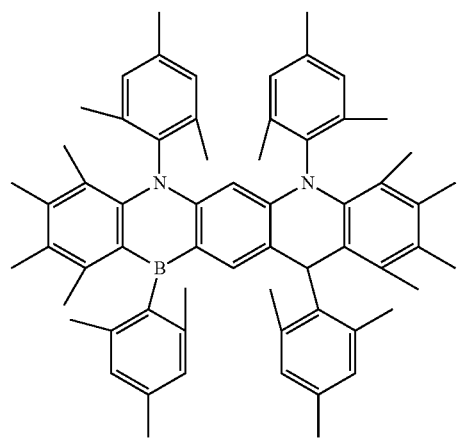
70
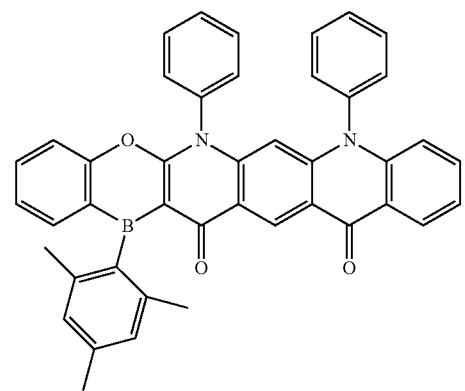
71
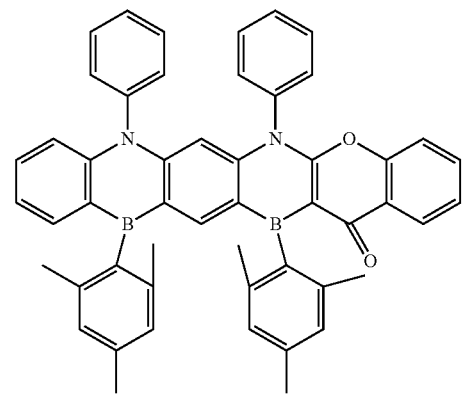
72
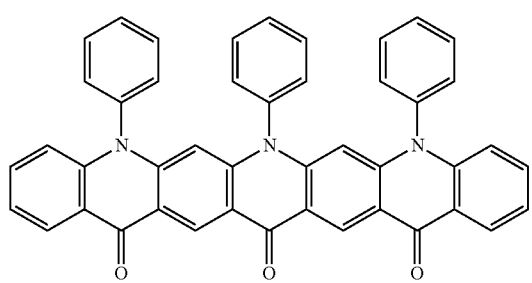
73
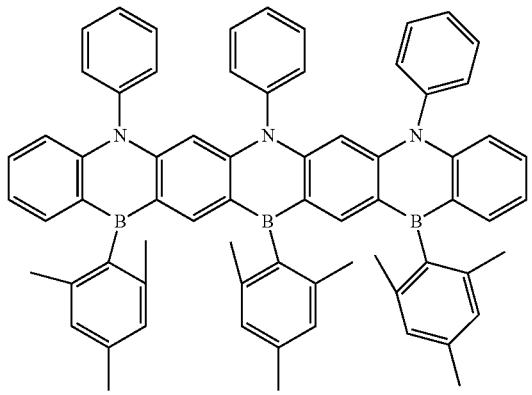
74
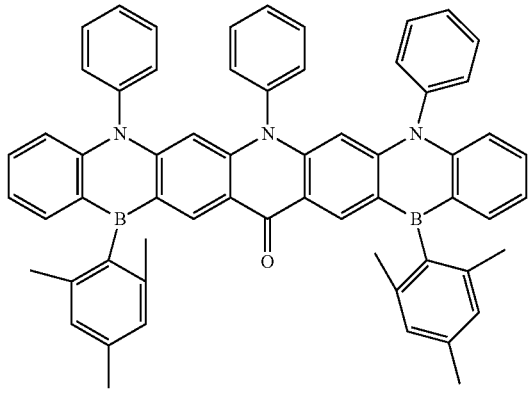
75
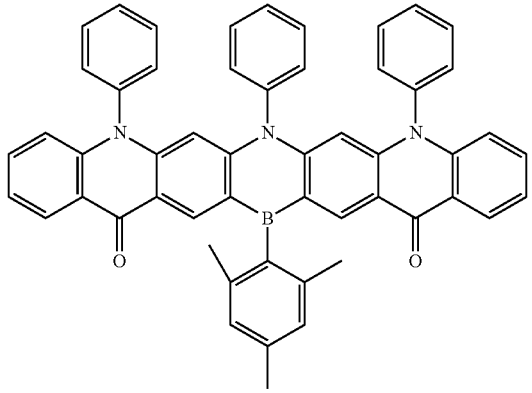
76
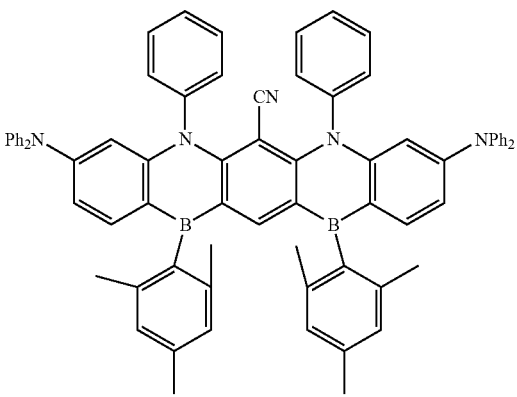

-continued
77
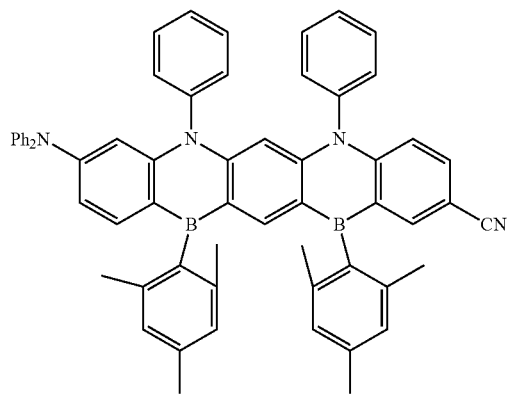
78
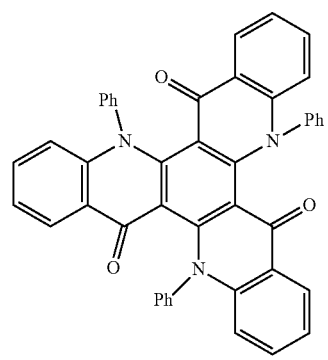
79
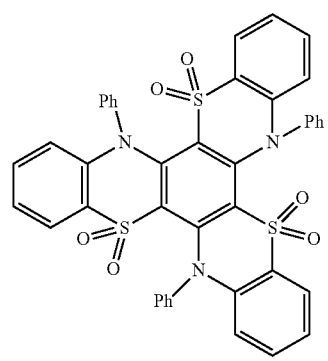
80
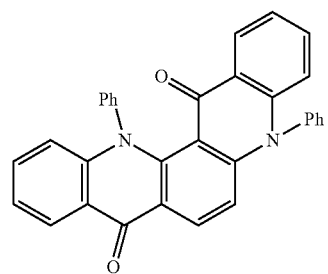
-continued
81
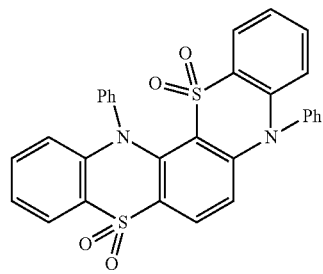
82
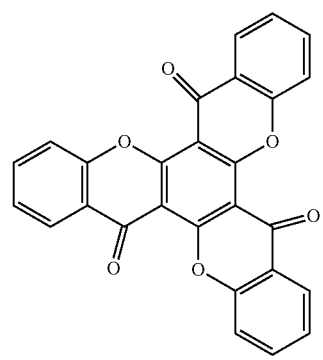
83
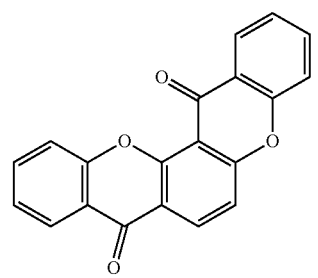
84
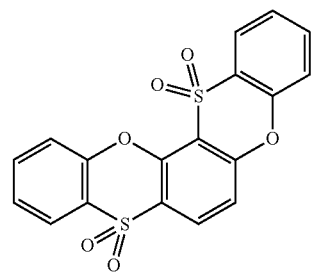
85
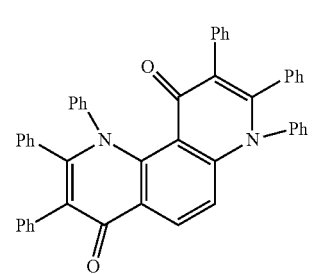

86
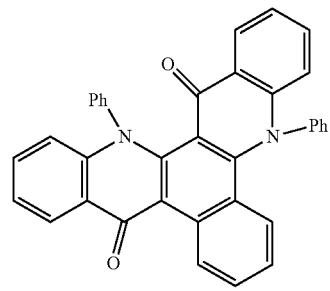
87
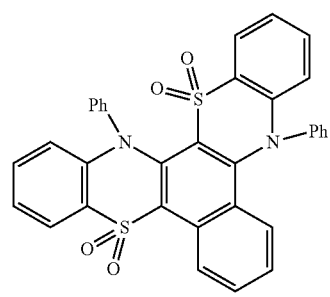
88
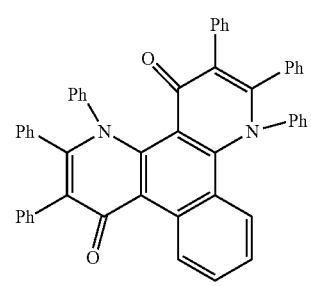
89
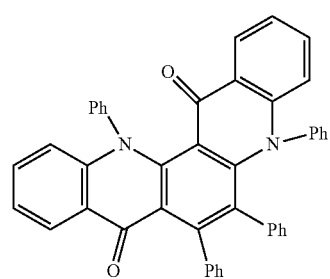
90
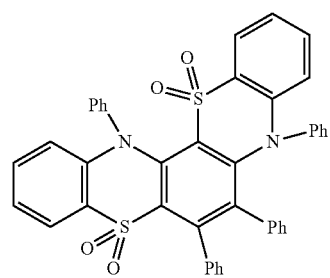
91
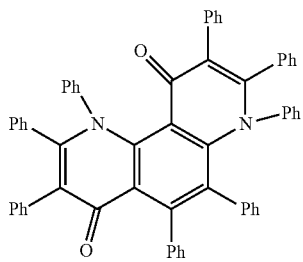
92
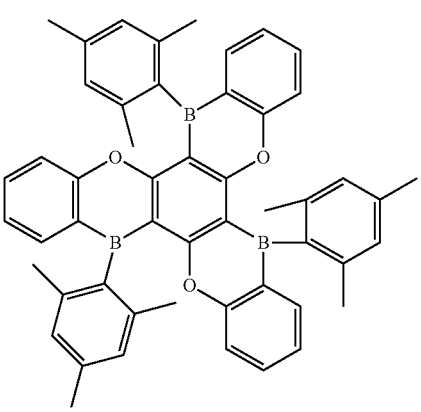
93
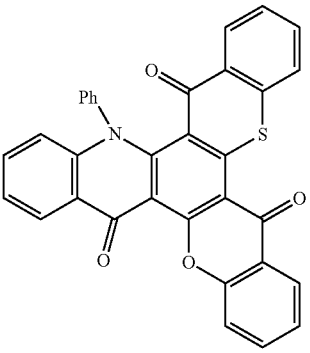
94
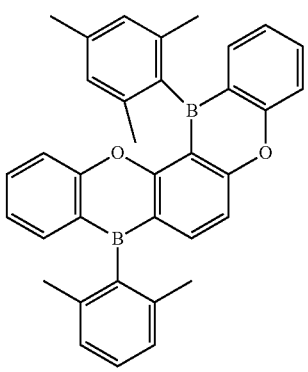

95
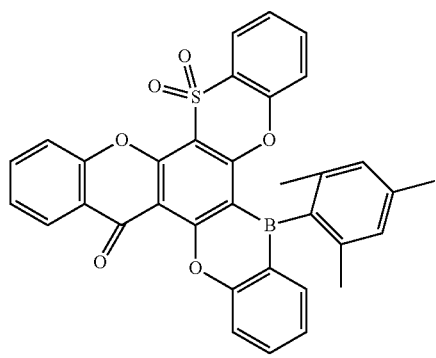
96
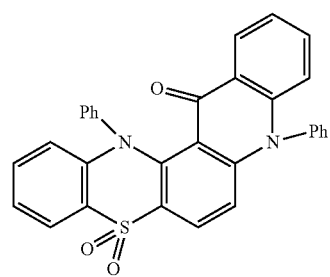
97
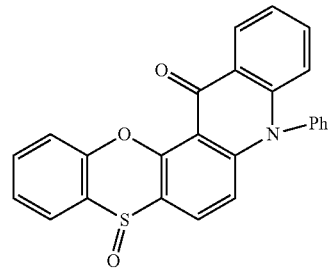
98
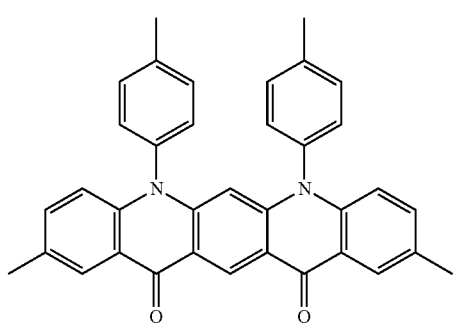
99
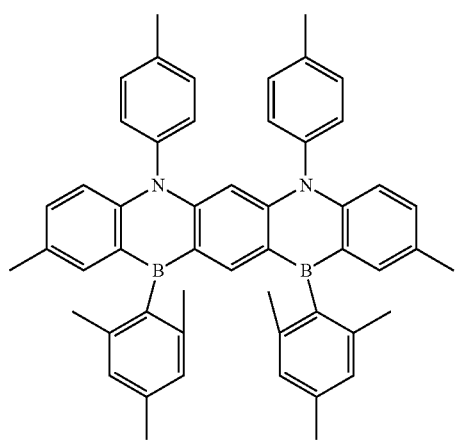
100
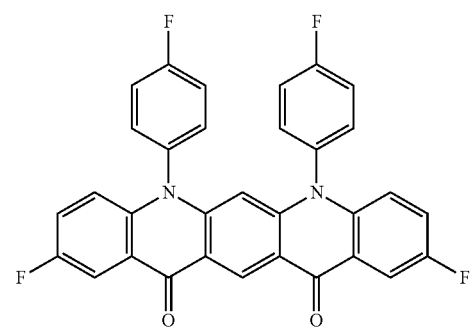
101
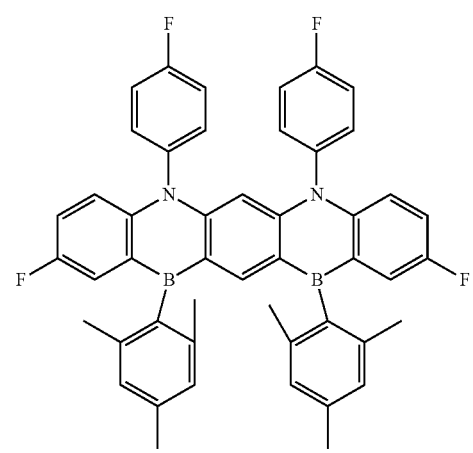
102
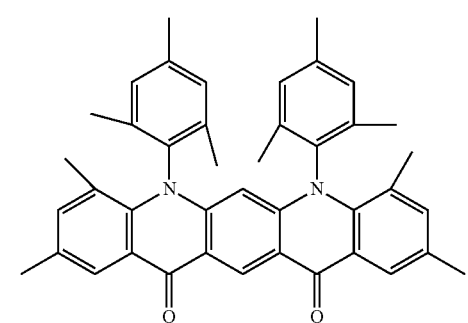

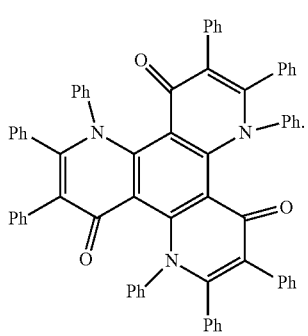

103

In Compound Group 1, iPr represents an isopropyl group, and Ph represents a phenyl group.

The polycyclic compound according to an example embodiment may have the lowest triplet excitation energy (T1) of about 3.0 eV or more.

In the organic electroluminescence device 10 according to an example embodiment, the emission layer EML may emit delayed fluorescence. For example, the emission layer EML may emit thermally activated delayed fluorescence (TADF). In the organic electroluminescence device 10 according to an example embodiment, the emission layer EML may emit phosphorescence.

The emission layer EML of the organic electroluminescence device 10 may emit blue light. For example, the emission layer EML of the organic electroluminescence device 10 according to an example embodiment may emit blue light in a region of about 480 nm or less.

In an embodiment, the emission layer EML may include a host and a dopant, and may include the polycyclic compound as a host or a dopant. For example, in the organic electroluminescence device 10 according to an example embodiment, the emission layer EML may include a host for emitting delayed fluorescence and a dopant for emitting delayed fluorescence, and may include the polycyclic compound as the host for emitting delayed fluorescence and the dopant for emitting delayed fluorescence. The emission layer EML may include at least one of the polycyclic compounds represented in Compound Group 1 as a host for thermally activated delayed fluorescence and a dopant for thermally activated delayed fluorescence.

In an embodiment, the emission layer EML may be a delayed fluorescence emission layer, and the emission layer EML may include a host material and the polycyclic compound. In an embodiment, the emission layer EML may be a delayed fluorescence emission layer, and the emission layer EML may include the polycyclic compound and a known dopant.

In an embodiment, the emission layer EML may further include a host material. For example, in an embodiment, the emission layer EML may include as a host material, tris (8-hydroxyquinolino) aluminum (Alq3), 4,4'-bis(N-carbazolyl)-1,1'-biphenyl (CBP), poly (n-vinylcarbazole) (PVK), 9,10-di (naphthalene-2-yl) anthracene (ADN), 4,4',4"-tris (carbazol-9-yl)-triphenylamine (TCTA), 1,3,5-tris (N-phenylbenzimidazole-2-yl) benzene (TPBi), 3-tert-butyl-9,10-di(naphth-2-yl) anthracene (TBADN), distyrylarylene (DSA), 4,4'-bis(9-carbazolyl)-2,2'-dimethyl-biphenyl (CDBP), 2-methyl-9,10-bis (naphthalen-2-yl) anthracene (MADN), bis [2-(diphenylphosphino) phenyl] ether oxide (DPEPO), hexaphenyl cyclotriphosphazene (CP1), 1,4-bis (triphenylsilyl) benzene (UGH2), hexaphenylcyclotrisiloxane (DPSiO3), octaphenylcyclotetrasiloxane (DPSiO4), 2,8-bis (diphenylphosphoryl) dibenzofuran (PPF), 3,3'-bis (N-carbazolyl)-1,1'-biphenyl (mCBP), 1,3-bis(N-carbazolyl) benzene (mCP), etc. Suitable host materials for emitting delayed fluorescence may be included in addition to the suggested host materials.

In the organic electroluminescence device 10 according to an example embodiment, the emission layer EML may further include a dopant material. In an embodiment, the emission layer EML may include as a dopant, styryl derivatives (for example, 1,4-bis [2-(3-N-ethylcarbazolyl) vinyl] benzene (BCzVB), 4-(di-p-tolylamino)-4'-[(di-p-tolylamino) styryl] stilbene (DPAVB), and N-(4-((E)-2-(6-((E)-4-(diphenylamino) styryl) naphthalen-2-yl) vinyl)phenyl)-N-phenylbenzenamine (N-BDAVBi), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino) pyrene), etc.

In an embodiment, the emission layer EML emits phosphorescence, and the emission layer EML may include the polycyclic compound as a phosphorescence host material.

In an embodiment, the emission layer EML may include the polycyclic compound according to an example embodiment as a phosphorescence host. The polycyclic compound according to an example embodiment may be used as a phosphorescence host of the emission layer EML, and the emission layer EML may further include a phosphorescence dopant material. In an embodiment, the emission layer EML may further include a host material together with the polycyclic compound according to an example embodiment.

The emission layer EML may include the polycyclic compound according to an example embodiment and a phosphorescence dopant material. For example, the phosphorescence dopant may use a metal complex including iridium (Ir), platinum (Pt), osmium (Os), gold (Au), titanium (Ti), zirconium (Zr), hafnium (Hf), europium (Eu), terbium (Tb), or thulium (Tm). For example, iridium (III) bis(4,6-difluorophenylpyridinato-N,C2') picolinate (FIrpic), bis(2,4-difluorophenylpyridinato (Fir6), or platinum octaethyl porphyrin (PtOEP) may be used as the phosphorescence dopant.

The emission layer EML may further include a phosphorescence host material, for example, bis(4-(9H-carbazol-9-yl)phenyl) diphenylsilane (BCPDS).

In the organic electroluminescence devices 10 according to example embodiments, shown in FIGS. 1 to 3, the electron transport region ETR may be provided on the emission layer EML. The electron transport region ETR may include at least one of an hole blocking layer HBL, an electron transport layer ETL, or an electron injection layer EIL.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. Further, the electron transport region ETR may have a single layer structure having a plurality of different materials, or a structure laminated from the emission layer EML of electron transport layer ETL/electron injection layer EIL, or hole blocking layer HBL/electron transport layer ETL/electron injection layer EIL. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

When the electron transport region ETR includes an electron transport layer ETL, the electron transport region ETR may include an anthracene-based compound. In an example embodiment, the electron transport region may include, for example, tris (8-hydroxyquinolinato) aluminum (Alq3), 1,3,5-tri [(3-pyridyl)-phen-3-yl]benzene, 2,4,6-tris (3'-(pyridin-3-yl) biphenyl-3-yl)-1,3,5-triazine, 2-(4-(N-phenylbenzoimidazolyl-1-ylphenyl)-9,10-dinaphthylanthracene, 1,3,5-tri (1-phenyl-1H-benzo[d]imidazol-2-yl) benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis (benzoquinolin-10-olate (Bebq2), 9,10-di (naphthalene-2-yl) anthracene (ADN), or a mixture thereof. The thickness of the electron transport layer ETL may be from about 100 Å to about 1,000 Å and may be, for example, from about 150 Å to about 500 Å. When the thickness of the electron transport layer ETL satisfies the above-described range, satisfactory electron transport properties may be obtained without substantial increase of a driving voltage.

When the electron transport region ETR includes the electron injection layer EIL, the electron transport region ETR may include, for example, LiF, lithium quinolate (Liq), LizO, BaO, NaCl, CsF, a metal in lanthanides such as Yb, or a metal halide such as RbCl and RbI. The electron injection layer EIL may be formed using a mixed material of an electron transport material and an insulating organometal salt. The organometal salt may be a material having an energy band gap of about 4 eV or more. For example, the organometal salt may include metal acetates, metal benzoates, metal acetoacetates, metal acetylacetonates, or metal stearates. The thickness of the electron injection layer EIL may be from about 1 Å to about 100 Å, and from about 3 Å to about 90 Å. When the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP) or 4,7-diphenyl-1,10-phenanthroline (Bphen).

The second electrode EL2 may be provided on the electron transport region ETR. The second electrode EL2 may be a common electrode or a cathode. The second electrode EL2 may be a transmissive electrode, a transflective electrode or a reflective electrode. When the second electrode EL2 is the transmissive electrode, the second electrode EL2 may include a transparent metal oxide, for example, ITO, IZO, ZnO, ITZO, etc.

When the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

The second electrode EL2 may be connected with an auxiliary electrode. When the second electrode EL2 is connected with the auxiliary electrode, the resistance of the second electrode EL2 may be decreased.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes may be recombined in the emission layer EML to produce excitons, and the excitons may emit light via transition from an excited state to a ground state.

The organic electroluminescence device 10 according to an example embodiment may include the polycyclic compound in the emission layer EML disposed between the first electrode EL1 and the second electrode EL2, and may achieve excellent emission efficiency and long life characteristic. For example, the organic electroluminescence device 10 according to an example embodiment may include the polycyclic compound in the emission layer EML so that the emission layer EML emits thermally activated delayed fluorescence, thereby achieving high emission efficiency and improved life characteristic, and showing narrow half-width characteristic in the wavelength region of blue light. The organic electroluminescence device 10 according to an example embodiment may include the polycyclic compound as the host material of the emission layer EML emitting phosphorescence and may show improved emission efficiency. An embodiment provides a polycyclic compound represented by any one among Formula 1 to Formula 3. The polycyclic compound may be used as a material for an organic electroluminescence device. For example, the polycyclic compound may be used as a material of the emission layer of an organic electroluminescence device.

Particular explanation on the polycyclic compound according to an example embodiment is the same as described above, and will be omitted. For example, the polycyclic compound according to an example embodiment may be any one selected from the compounds represented in Compound Group 1.

The polycyclic compound according to an example embodiment is a heterocyclic compound including at least three six-membered rings, and includes both an electron donor moiety and an electron acceptor moiety in at least two six-membered rings, and thus may be used as a material emitting thermally activated delayed fluorescence. A polycyclic compound according to an example embodiment has a structural characteristic in which at least two six-membered rings including an electron donor moiety and an electron acceptor moiety are not neighbored, and includes a carbonyl group, a sulfonyl group, a substituted boron group, or the like, that has high chemical stability as an electron acceptor moiety, thereby improving the life and emission efficiency of an organic electroluminescence device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

1. Synthesis of Polycyclic Compounds

Synthetic methods of the polycyclic compounds according to example embodiments will now be explained for Compounds 2, 8, 9, 13, 19, 21, 31, 50, 76 and 77.

(1) Synthetic of Compound 2

Compound 2 which is a polycyclic compound according to an example embodiment, may be synthesized, for example, by the following Reaction 1-1 to Reaction 1-3:

<Synthesis of Compound A>

[Reaction 1-1]

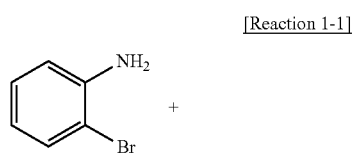

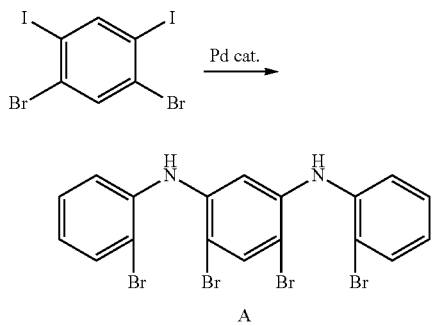

Under an argon (Ar) atmosphere, to a 100 ml, three-neck flask, 34.4 g (200 mmol) of 2-bromoaniline, 48.8 g (100 mmol) of 1,3-diiodo-4,6-dibromobenzene, 4.58 g (5.0 mmol) of $Pd_2(dba)_3$, 5.54 g (10.0 mmol) of dppf and 23.1 g (240 mmol) of NaOtBu were added and stirred in 400 ml of a toluene solvent at about 110° C. for about 16 hours. After cooling in the air, toluene was added and the resultant product was filtered. Solvents were removed by distillation. The crude product thus obtained was separated by silica gel column chromatography to obtain 20.8 g (yield 36%) of white solid Compound A. The molecular weight of Compound A as measured by FAB-MS was 571.

<Synthesis of Compound B>

[Reaction 1-2]

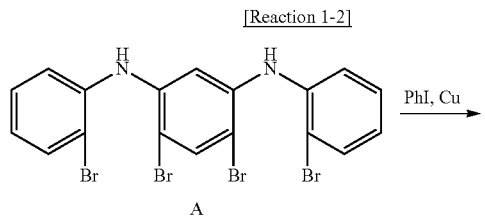

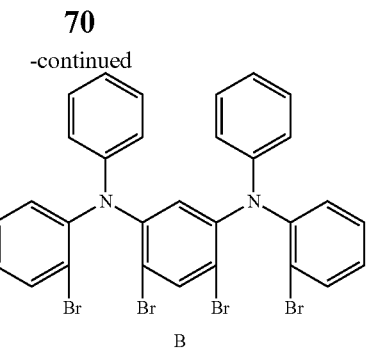

Under an argon atmosphere, to a 200 ml, three-neck flask, 20.8 g (36.0 mmol) of Compound A, 40.0 ml of iodobenzene, 2.31 g (36.0 mmol) of Cu powder and 24.87 g (180 mmol) of $K_2CO_3$ were added and stirred at about 180° C. for about 48 hours. After cooling in the air, toluene was added and the resultant product was filtered. Solvents were removed by distillation. The crude product thus obtained was separated by silica gel column chromatography to obtain 7.08 g (yield 27%) of white solid Compound B. The molecular weight of Compound B as measured by FAB-MS was 723.

<Synthesis of Compound 2>

[Reaction 1-3]

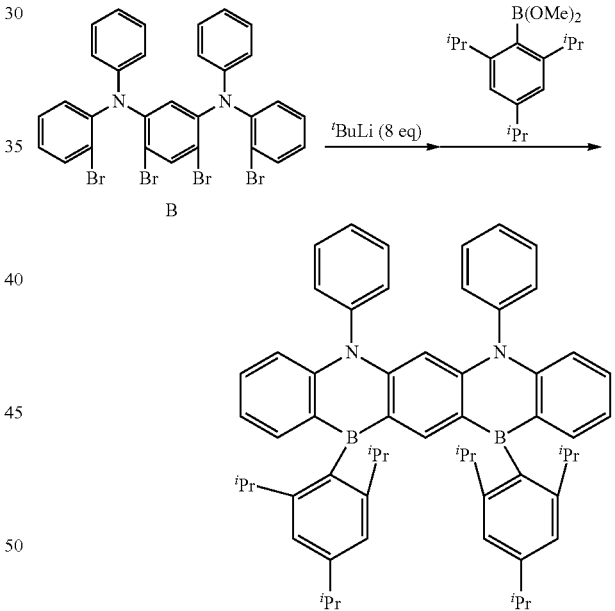

Under an argon atmosphere, to a 300 ml, three-neck flask, 2.35 g (3.2 mmol) of Compound B, and 128 ml of a dehydrated THF solution were added and stirred at about −80° C. 13.5 ml (25.7 mmol) of 1.9 M t-BuLi pentane solution was dropwise added thereto and stirred for about 2 hours. Then, stirring was performed for about 3 hours while elevating the temperature to about −10° C. The temperature was decreased to about −80° C. again and 13 ml of a dehydrated THF solution of 1.80 g (6.5 mmol) of 2,4,6-triisopropylphenylboronic acid methyl ester was added thereto dropwise, followed by stirring for about 2 hours at about −80° C. and then for about 3 hours at room temperature. After finishing the reaction, the reaction mixture was washed with water. The organic phase thus obtained was concentrated to obtain a viscous material. The crude product thus obtained was separated by silica gel column chromatography to obtain 0.83 g (yield 31%) of white solid Compound 2. The molecular weight of Compound 2 as measured by FAB-MS was 836. The chemical shift values δ of Compound 2 measured by 1H-NMR (CDCl₃) were [7.71 (2H), 7.31-7.16 (13H), 7.10-6.98 (8H), 6.83 (1H), 2.90-2.85 (6H), 1.22-1.16 (36H)].

(2) Synthesis of Compound 8

Compound 8 which is a polycyclic compound according to an example embodiment, may be synthesized, for example, by the following Reaction 2:

[Reaction 2]

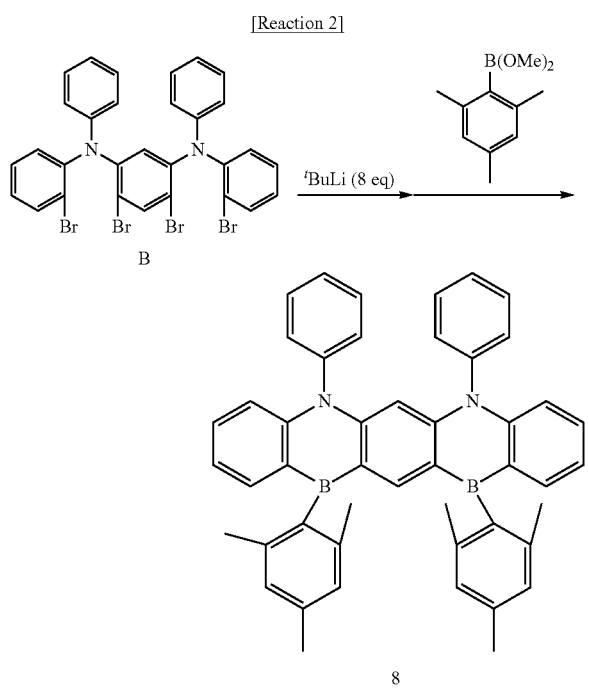

8

Under an argon atmosphere, to a 300 ml, three-neck flask, 2.35 g (3.2 mmol) of Compound B, and 128 ml of a dehydrated THF solution were added and stirred at about −80° C. 13.5 ml (25.7 mmol) of 1.9 M t-BuLi pentane solution was dropwise added thereto and stirred for about 2 hours. Then, stirring was performed for about 3 hours while elevating the temperature to about-10° C. The temperature was decreased to about −80° C. again and 13 ml of a dehydrated THF solution of 1.25 g (6.5 mmol) of trimethylphenylboronic acid methyl ester was added thereto dropwise, followed by stirring for about 2 hours at about −80° C. and then for about 3 hours at room temperature. After finishing the reaction, the reaction mixture was washed with water. The organic phase thus obtained was concentrated to obtain a viscous material. The crude product thus obtained was separated by silica gel column chromatography to obtain 0.92 g (yield 43%) of white solid Compound 8. The molecular weight of Compound 8 as measured by FAB-MS was 668. The chemical shift values δ of Compound 8 measured by 1H-NMR (CDCl₃) were [7.71 (2H), 7.31-7.16 (13H), 7.10-6.95 (8H), 6.83 (1H), 2.33 (12H), 2.18 (6H)].

(3) Synthesis of Compound 50

Compound 50 which is a polycyclic compound according to an example embodiment, may be synthesized, for example, by the following Reaction 3-1 to Reaction 3-5:

<Synthesis of Compound C>

[Reaction 3-1]

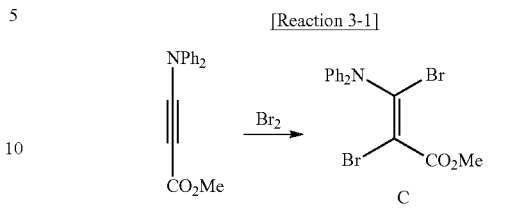

Under an argon atmosphere, to a 500 ml, three-neck flask, 200 ml of a dehydrated acetonitrile solution of 23.5 g (100 mmol) of 4-(diphenylamino)-3-methylpropiolate was added and stirred at about 0° C. 5.2 ml (100 mmol) of bromine was added thereto dropwise, followed by stirring at about 0° C. for about 2 hours and then at room temperature for about 3 hours. After finishing the reaction, chloroform was added, and the resultant mixture was washed with an aqueous sodium thiosulfate solution and water. The organic phase thus obtained was concentrated and the crude product thus obtained was separated by silica gel column chromatography to obtain 10.7 g (yield 26%) of white solid Compound C. The molecular weight of Compound C as measured by FAB-MS was 409.

<Synthesis of Compound D>

[Reaction 3-2]

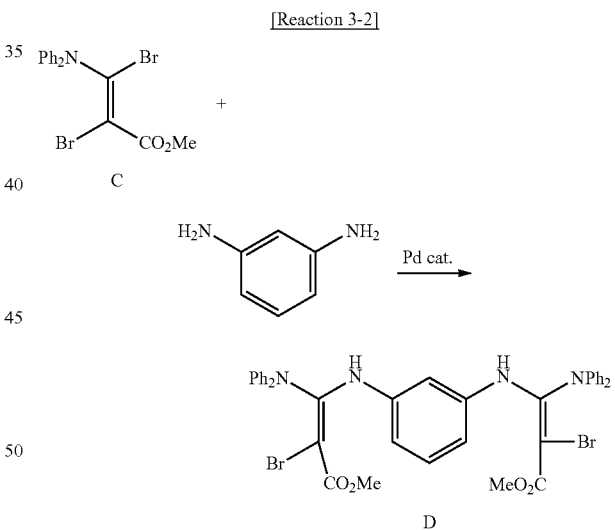

Under an argon atmosphere, to a 300 ml, three-neck flask, 10.7 g (26 mmol) of Compound C, 1.41 g (13 mmol) of 1,3-benzenediamine, 1.19 g (1.3 mmol) of Pd₂ (dba)₃, 2.79 g (5.2 mmol) of Brettphos and 16.6 g (78 mmol) of K₃PO₄ were added and stirred in 130 ml of a dioxane solvent at about 100° C. for about 2 hours. After cooling in the air, toluene was added and the resultant product was filtered. Solvents were removed by distillation. The crude product thus obtained was separated by silica gel column chromatography to obtain 2.80 g (yield 28%) of white solid Compound D. The molecular weight of Compound D as measured by FAB-MS was 766.

<Synthesis of Compound E>

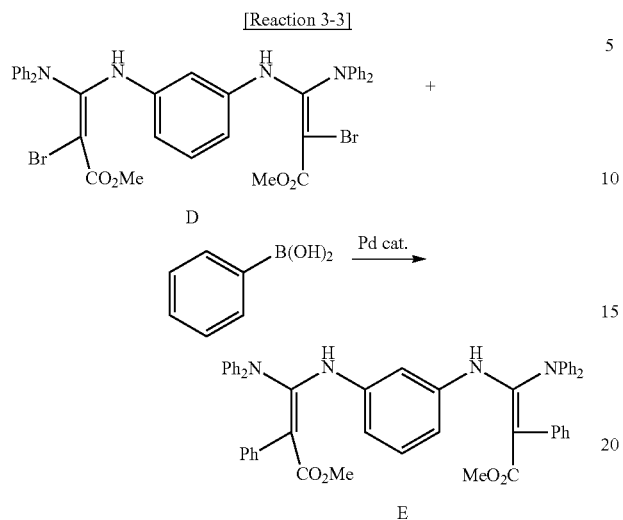

Under an argon atmosphere, to a 200 ml, three-neck flask, 2.77 g (3.6 mmol) of Compound D, 0.88 g (7.2 mmol) of phenylboronic acid, 83 mg (0.072 mmol) of Pd (PPh$_3$)$_4$, 2.49 g (18.0 mmol) of K$_2$CO$_3$, and 36 ml of dioxane were added and stirred at about 100° C. for about 2 hours. After cooling in the air, water was added, an organic layer was separately taken, and solvents were removed by distillation. The crude product thus obtained was separated by silica gel column chromatography to obtain 2.56 g (yield 93%) of white solid Compound E. The molecular weight of Compound E as measured by FAB-MS was 762.

<Synthesis of Compound F>

[Reaction 3-4]

Under an argon atmosphere, to a 200 ml, three-neck flask, 26 g of polyphosphoric acid was added and stirred at about 150° C. 2.55 g (3.3 mmol) of Compound E was added thereto and stirred at about 200° C. for about 2 hours. After cooling in the air, water was added, and white precipitate was obtained by filtering. The crude product thus obtained was separated by silica gel column chromatography to obtain 1.11 g (yield 48%) of white solid Compound F. The molecular weight of Compound F as measured by FAB-MS was 698.

<Synthesis of Compound 50>

[Reaction 3-5]

Under an Ar atmosphere, to a 200 ml, three-neck flask, 1.11 g (1.6 mmol) of Compound F, 1.8 ml of iodobenzene, 0.10 g (1.6 mmol) of Cu powder and 1.11 g (8.0 mmol) of K$_2$CO$_3$ were added and stirred at about 180° C. for about 48 hours. After cooling in the air, toluene was added and the resultant product was filtered. Solvents were removed by distillation. The crude product thus obtained was separated by silica gel column chromatography to obtain 0.76 g (yield 56%) of white solid Compound 50. The molecular weight of Compound 50 as measured by FAB-MS was 850. The chemical shift values δ of Compound 50 measured by 1H-NMR (CDCl$_3$) were [7.61 (1H), 7.43-7.33 (24H), 7.23-7.15 (5H), 7.02-6.98 (12H)].

(4) Synthesis of Compound 76

Compound 76 which is a polycyclic compound according to an example embodiment, may be synthesized, for example, by the following Reaction 4-1 to Reaction 4-4:

<Synthesis of Compound G>

[Reaction 4-1]

Under an argon atmosphere, to a 1,000 ml, three-neck flask, 36.1 g (120 mmol) of 1-bromo-4-fluoro-2-iodobenzene, 17.2 g (50 mmol) of 2,4,6-tribromo-1,3-benzenediamine, 4.58 g (5.0 mmol) of Pd$_2$(dba)$_3$, 5.54 g (10.0 mmol) of dppf, and 23.1 g (240 mmol) of NaOtBu were added and stirred in 200 ml of a toluene solvent at about 110° C. for about 16 hours. After cooling in the air, toluene was added and the resultant product was filtered. Solvents were removed by distillation. The crude product thus obtained was separated by silica gel column chromatography to obtain 10.4 g (yield 30%) of white solid Compound G.

Synthesis of Compound H>

[Reaction 4-2]

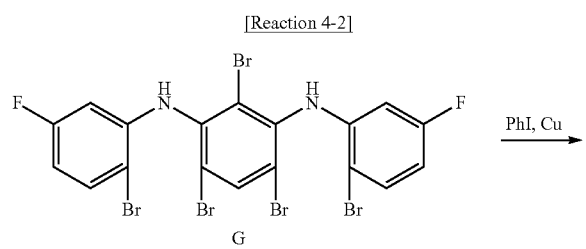

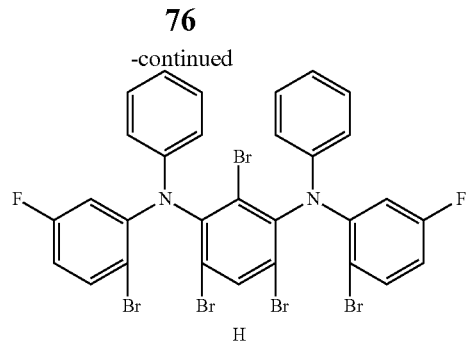

Under an argon atmosphere, to a 200 ml, three-neck flask, 10.4 g (15.0 mmol) of Compound G, 16.7 ml of iodobenzene, 0.96 g (15.0 mmol) of Cu powder and 10.36 g (75 mmol) of K$_2$CO$_3$ were added and stirred at about 180° C. for about 48 hours. After cooling in the air, toluene was added and the resultant product was filtered. Solvents were removed by distillation. The crude product thus obtained was separated by silica gel column chromatography to obtain 1.91 g (yield 15%) of white solid Compound H. The molecular weight of Compound H as measured by FAB-MS was 837.

<Synthesis of Compound I>

[Reaction 4-3]

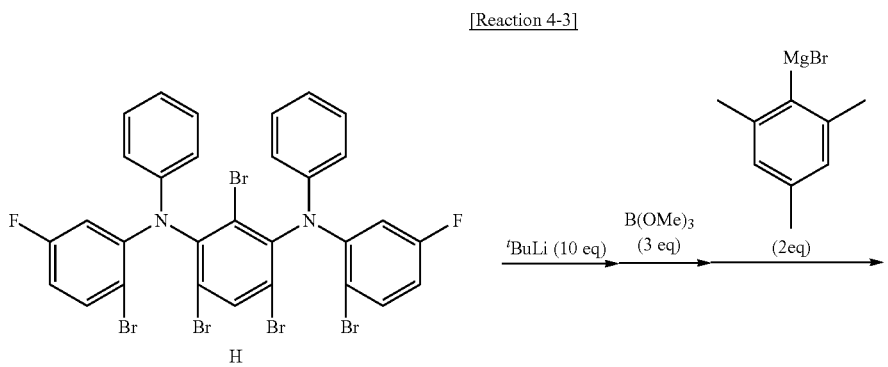

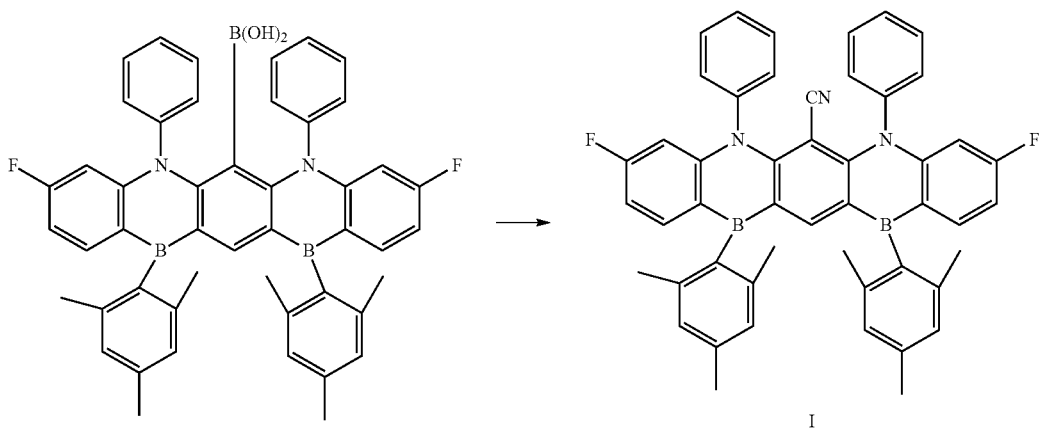

Under an argon atmosphere, to a 300 ml, three-neck flask, 137 ml of a dehydrated THF solution of 1.90 g (2.7 mmol) of Compound H was added and stirred at about −80° C. 14.5 ml (27.5 mmol) of 1.9 M t-BuLi pentane solution was dropwise added thereto and stirred for about 2 hours. Then, stirring was performed for about 3 hours while elevating the temperature to about −10° C. The temperature was decreased to about-80° C. again and 17 ml of a dehydrated THF solution of 0.80 g (8.3 mmol) of trimethoxyborane was added thereto dropwise, followed by stirring for about 2 hours at about −80° C. and then for about 3 hours at room temperature. The temperature was decreased to about-80° C. again and 5.4 ml (5.4 mmol) of a THF solution of 1.0 M mesithylmagnesiumbromide was added thereto dropwise, followed by stirring for about 2 hours at about −80° C. and then for about 3 hours at room temperature. After finishing the reaction, the reaction mixture was washed with water. The organic phase thus obtained was concentrated to obtain a viscous material. The crude product thus obtained was dissolved in THF, followed by passing through a short silica pad. Solvents were removed by distillation to obtain a white solid compound.

The white solid thus obtained was moved into a 20 ml, branched flask, and 0.25 g (2.7 mmol) of malononitrile, 13 mg (0.027 mmol) of [RhCl (cod)] 2, and 1.76 g (5.4 mmol) of $Cs_2CO_3$ were added thereto, followed by stirring under an argon atmosphere in 5.4 ml of a dioxane solvent at about 100° C. for about 6 hours. After finishing the reaction, the reaction mixture was washed with water, the organic phase thus obtained was concentrated, and the crude product thus obtained was separated by silica gel column chromatography to obtain 0.26 g (yield 13%) of white solid Compound I. The molecular weight of Compound I as measured by FAB-MS was 729.

<Synthesis of Compound 76>

[Reaction 4-4]

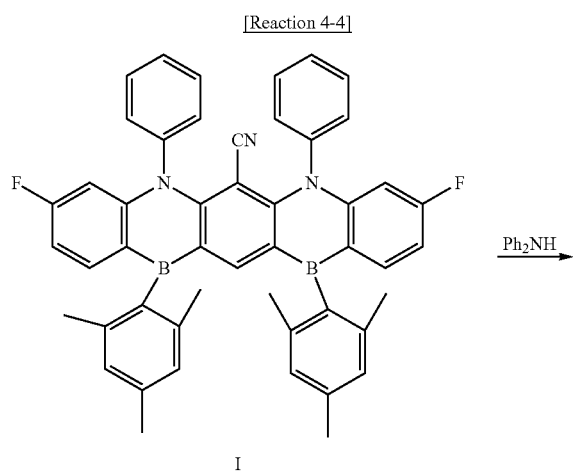

I

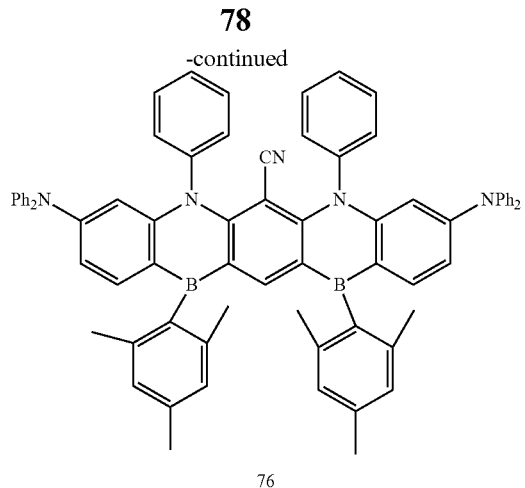

76

Under an argon atmosphere, to a 200 ml, three-neck flask, 0.26 g (0.36 mmol) of Compound I, 0.19 g (1.1 mmol) of diphenylamine, 0.59 g (1.8 mmol) of $Cs_2CO_3$, and 1.5 ml of DMSO were added and stirred at about 160° C. for about 8 hours. After cooling in the air, water was added, and white precipitate was obtained by filtering. The crude product thus obtained was separated by silica gel column chromatography to obtain 0.25 g (yield 68%) of white solid Compound 76. The molecular weight of Compound 76 as measured by FAB-MS was 1,027. The chemical shift values δ of Compound 76 measured by 1H-NMR (CDCl$_3$) were [7.67 (2H), 7.53 (1H), 7.26-7.22 (12H), 7.10-6.95 (22H), 6.86-6.81 (4H), 2.33 (12H), 2.18 (6H)].

(5) Synthetic of Compound 77

Compound 77 which is a polycyclic compound according to an example embodiment, may be synthesized, for example, by the following Reaction 5-1 to Reaction 5-6:

<Synthesis of Compound J>

[Reaction 5-1]

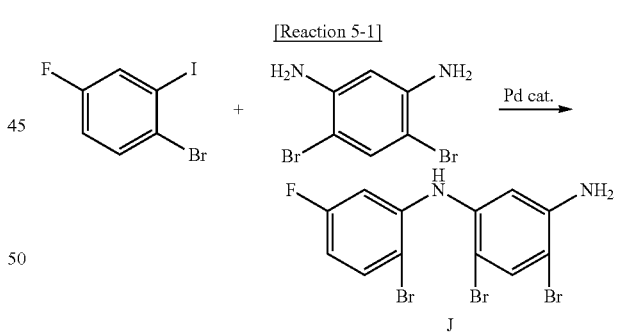

J

Under an argon atmosphere, to a 500 ml, three-neck flask, 18.1 g (60 mmol) of 1-bromo-4-fluoro-2-iodobenzene, 17.2 g (50 mmol) of 6-dibromobenzene-1,3-diamine, 2.29 g (2.5 mmol) of Pd$_2$(dba)$_3$, 2.77 g (5.0 mmol) of dppf and 5.77 g (60 mmol) of NaOtBu were added and stirred in 100 ml of a toluene solvent at about 110° C. for about 16 hours. After cooling in the air, toluene was added and the resultant product was filtered. Solvents were removed by distillation. The crude product thus obtained was separated by silica gel column chromatography to obtain 8.83 g (yield 41%) of white solid Compound J. The molecular weight of Compound J as measured by FAB-MS was 435.

<Synthesis of Compound K>

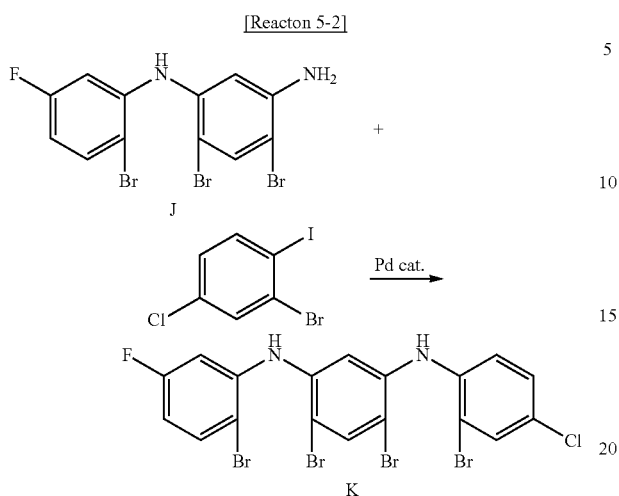

Under an argon atmosphere, to a 200 ml, three-neck flask, 7.61 g (24 mmol) of 2-bromo-4-chloro-1-iodobenzene, 8.78 g (20 mmol) of Compound J, 0.92 g (1.0 mmol) of $Pd_2(dba)_3$, 1.11 g (2.0 mmol) of dppf and 2.31 g (24 mmol) of NaOtBu were added and stirred in 40 ml of a toluene solvent at about 100° C. for about 16 hours. After cooling in the air, toluene was added and the resultant product was filtered. Solvents were removed by distillation. The crude product thus obtained was separated by silica gel column chromatography to obtain 6.30 g (yield 50%) of white solid Compound K. The molecular weight of Compound K as measured by FAB-MS was 623.

<Synthesis of Compound L>

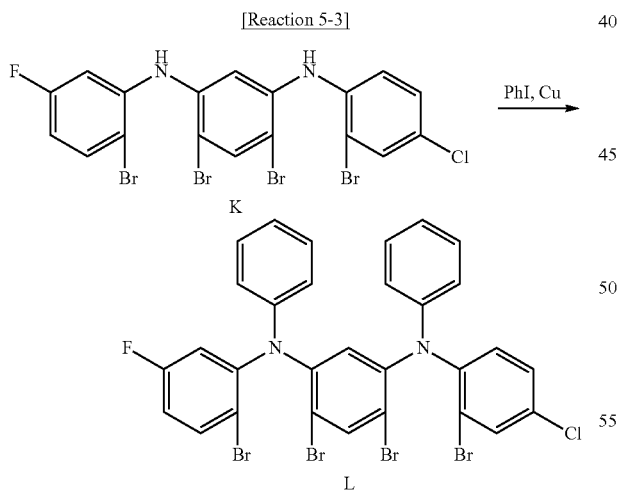

Under an argon atmosphere, to a 200 ml, three-neck flask, 6.28 g (10.0 mmol) of Compound K, 11.2 ml of iodobenzene, 0.64 g (10.0 mmol) of Cu powder and 6.91 g (50 mmol) of $K_2CO_3$ were added and stirred at about 180° C. for about 48 hours. After cooling in the air, toluene was added and the resultant product was filtered. Solvents were removed by distillation. The crude product thus obtained was separated by silica gel column chromatography to obtain 1.49 g (yield 19%) of white solid Compound L. The molecular weight of Compound L as measured by FAB-MS was 775.

<Synthesis of Compound M>

Under an argon atmosphere, to a 300 ml, three-neck flask, 1.49 g (1.9 mmol) of Compound L, and 76 ml of a dehydrated THF solution were added and stirred at about −80° C. 8.0 ml (15.2 mmol) of 1.9 M t-BuLi pentane solution was dropwise added thereto and stirred for about 2 hours. Then, stirring was performed for about 3 hours while elevating the temperature to about −10° C. The temperature was decreased to about-80° C. again and 7 ml of a dehydrated THF solution of 0.73 g (3.8 mmol) of 2,4,6-trimethylphenylboronic acid methyl ester was added thereto dropwise, followed by stirring for about 2 hours at about −80° C. and then for about 3 hours at room temperature. After finishing the reaction, the reaction mixture was washed with water. The organic phase thus obtained was concentrated to obtain a viscous material. The crude product thus obtained was separated by silica gel column chromatography to obtain 0.52 g (yield 38%) of white solid Compound M. The molecular weight of Compound M as measured by FAB-MS was 720.

<Synthesis of Compound N>

[Reaction 5-5]

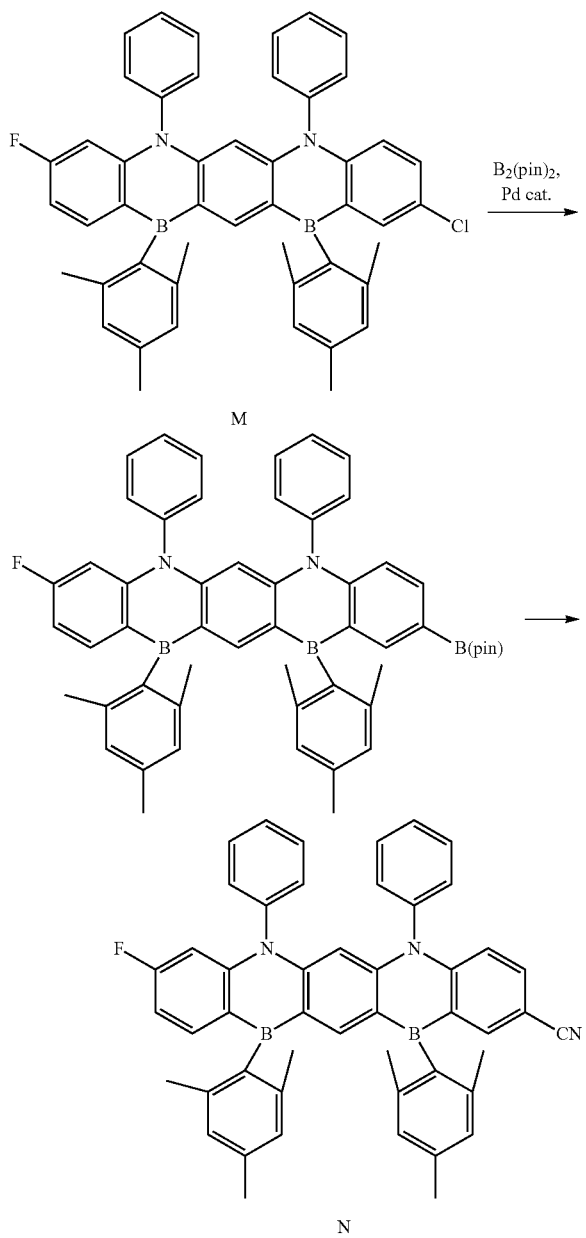

M

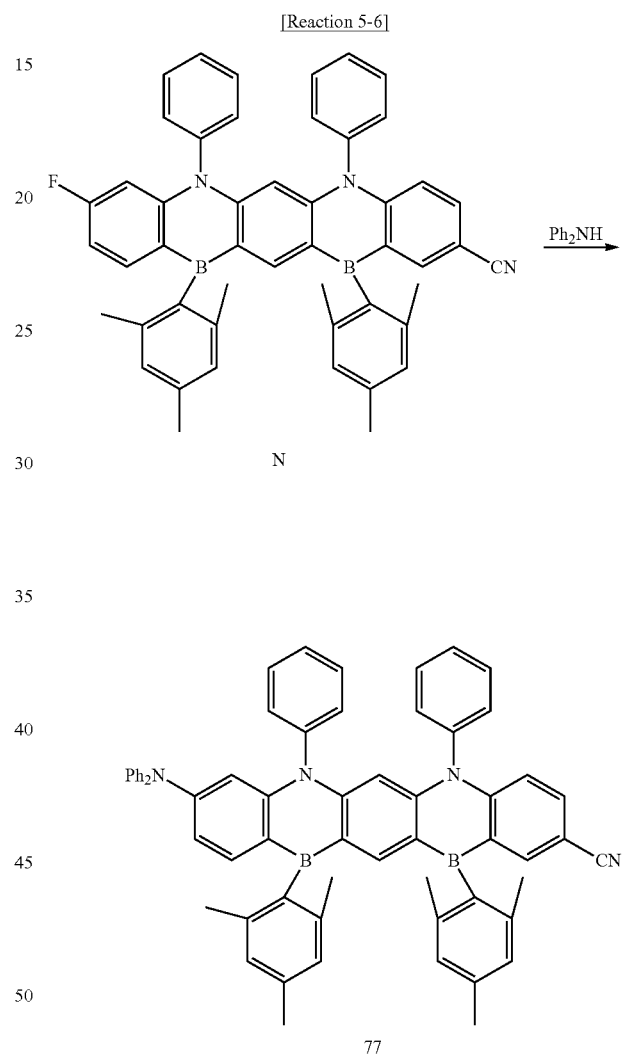

N

Under an argon atmosphere, to a 20 ml, branched flask, 0.52 g (0.72 mmol) of Compound M, 0.18 g (0.72 mmol) of bis (pinacolato)diboron, 8 mg (0.036 mmol) of Pd (OAc) 2, 34 mg (0.072 mmol) of Xphos, and 0.14 g (1.44 mmol) of KOAc were added followed by stirring in 3.6 ml of a dioxane solvent at about 100° C. for about 6 hours. After finishing the reaction, the reaction mixture was washed with water. The organic phase thus obtained was concentrated. The crude product thus obtained was dissolved in THF, followed by passing through a short silica pad. Solvents were removed by distillation to obtain a white solid compound The white solid thus obtained was moved into a 20 ml, branched flask, and 94 mg (0.72 mmol) of malononitrile, 5 mg (0.007 mmol) of [RhCl (cod)] 2, and 0.66 g (1.44 mmol) of $Cs_2CO_3$ were added thereto, followed by stirring under an argon atmosphere in 1.5 ml of a dioxane solvent at about 100° C. for about 6 hours. After finishing the reaction, the reaction mixture was washed with water, an organic phase thus obtained was concentrated, and the crude product thus obtained was separated by silica gel column chromatography to obtain 0.16 g (yield 32%) of white solid Compound N. The molecular weight of Compound N as measured by FAB-MS was 711.

<Synthesis of Compound 77>

[Reaction 5-6]

Under an argon atmosphere, to a 20 ml, branched flask, 0.16 g (0.23 mmol) of Compound N, 39 mg (0.23 mmol) of diphenylamine, 0.15 g (0.46 mmol) of $Cs_2CO_3$, and 0.5 ml of DMSO were added and stirred at about 160° C. for about 8 hours. After cooling in the air, water was added, and white precipitate was obtained by filtering. The crude product thus obtained was separated by silica gel column chromatography to obtain 0.12 g (yield 63%) of white solid Compound 77. The molecular weight of Compound 77 as measured by FAB-MS was 860. The chemical shift values δ of Compound 77 measured by 1H-NMR ($CDCl_3$) were [7.67 (1H), 7.54 (1H), 7.48 (1H), 7.36 (1H), 7.27-7.22 (9H), 7.10-6.95 (16H), 6.86-6.81 (3H), 2.35-2.31 (12H), 2.20-2.16 (6H)].

Compound 31 which is a polycyclic compound according to an example embodiment, may be synthesized, for example, by the following Reaction 6-1 to Reaction 6-3:

(6) Synthetic of Compound 31

<Synthesis of Compound O>

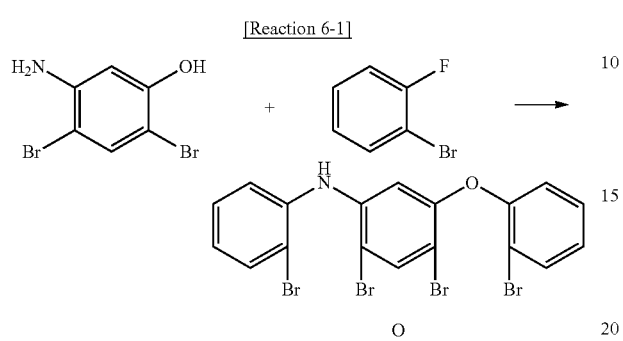

Under an argon atmosphere, to a 200 ml, three-neck flask, 13.4 g (50 mmol) of 5-amino-2,4-dibromophenol, 17.5 g (100 mmol) of 2-bromofluorobenzene, 65.2 g (200 mmol) of $Cs_2CO_3$, and 100 ml of DMSO were added and stirred at about 160° C. for about 10 hours. After cooling in the air, water was added, and white precipitate was obtained by filtering. The crude product thus obtained was separated by silica gel column chromatography to obtain 13.84 g (yield 48%) of white solid Compound O. The molecular weight of Compound O as measured by FAB-MS was 572.

<Synthesis of Compound P>

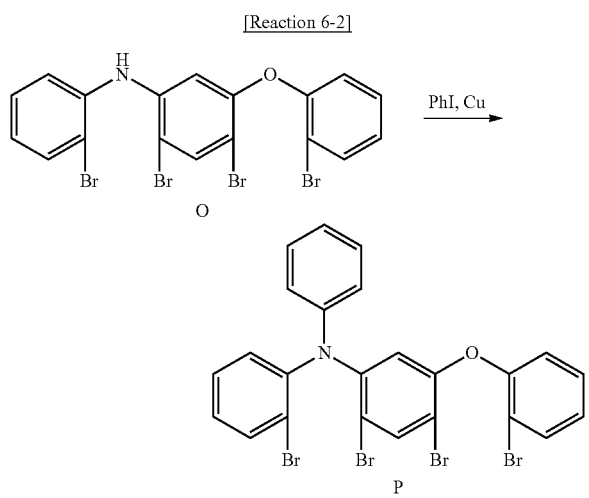

Under an argon atmosphere, to a 200 ml, three-neck flask, 13.8 g (24.0 mmol) of Compound O, 27.0 ml of iodobenzene, 0.31 g (4.9 mmol) of Cu powder and 9.95 g (72.0 mmol) of $K_2CO_3$ were added and stirred at about 180° C. for about 48 hours. After cooling in the air, toluene was added and the resultant product was filtered. Solvents were removed by distillation. The crude product thus obtained was separated by silica gel column chromatography to obtain 6.11 g (yield 39%) of white solid Compound P. The molecular weight of Compound P as measured by FAB-MS was 648.

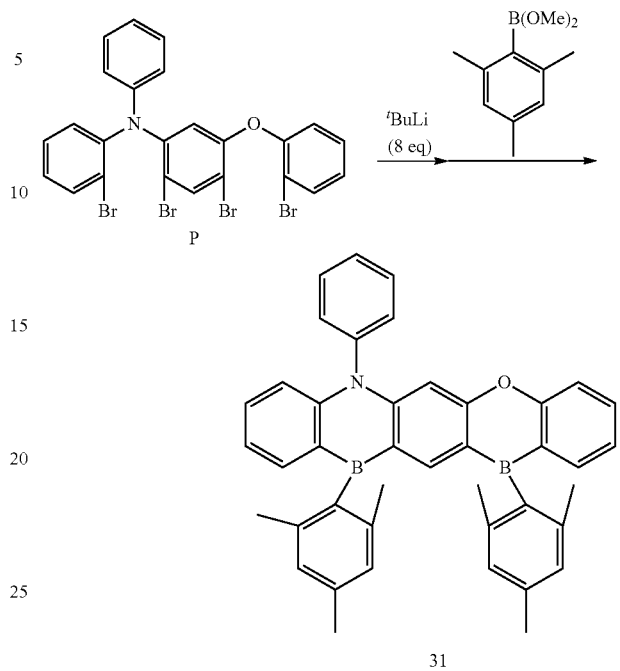

Under an argon atmosphere, to a 1,000 ml, three-neck flask, 6.08 g (9.3 mmol) of Compound P, and 372 ml of a dehydrated THF solution were added and stirred at about −80° C. 39.2 ml (74.5 mmol) of 1.9 M t-BuLi pentane solution was dropwise added thereto and stirred for about 2 hours. Then, stirring was performed for about 3 hours while elevating the temperature to about −10° C. The temperature was decreased to about−80° C. again and 37 ml of a dehydrated THF solution of 3.57 g (18.6 mmol) of 2,4,6-trimethylphenylboronic acid methyl ester was added thereto dropwise, followed by stirring for about 2 hours at about −80° C. and then for about 3 hours at room temperature. After finishing the reaction, the reaction mixture was washed with water. The organic phase thus obtained was concentrated to obtain a viscous material. The crude product thus obtained was separated by silica gel column chromatography to obtain 2.32 g (yield 42%) of white solid Compound 31. The molecular weight of Compound 31 as measured by FAB-MS was 593. The chemical shift values δ of Compound 31 measured by 1H-NMR ($CDCl_3$) were [7.71 (2H), 7.37-7.16 (6H), 7.10-6.95 (10H), 6.86 (1H), 2.35-2.31 (12H), 2.20-2.16 (6H)].

(7) Synthetic of Compound 19

Compound 19 which is a polycyclic compound according to an example embodiment, may be synthesized, for example, by the following Reaction 7-1 and Reaction 7-2:

<Synthesis of Compound Q>

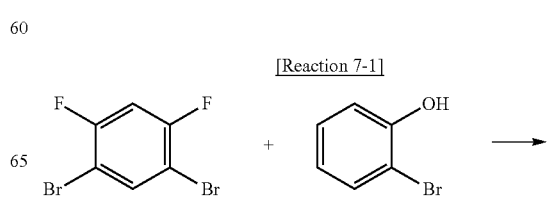

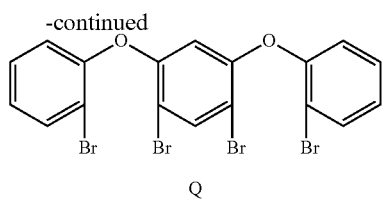

Q

Under an argon atmosphere, to a 200 ml, three-neck flask, 13.6 g (50 mmol) of 1,5-dibromo-2,4-difluorobenzene, 17.3 g (100 mmol) of 2-bromophenol, 65.2 g (200 mmol) of $Cs_2CO_3$, and 100 ml of DMSO were added and stirred at about 160° C. for about 10 hours. After cooling in the air, water was added, and white precipitate was obtained by filtering. The crude product thus obtained was separated by silica gel column chromatography to obtain 23.11 g (yield 80%) of white solid Compound Q. The molecular weight of Compound Q as measured by FAB-MS was 573.

<Synthesis of Compound 19>

[Reaction 7-2]

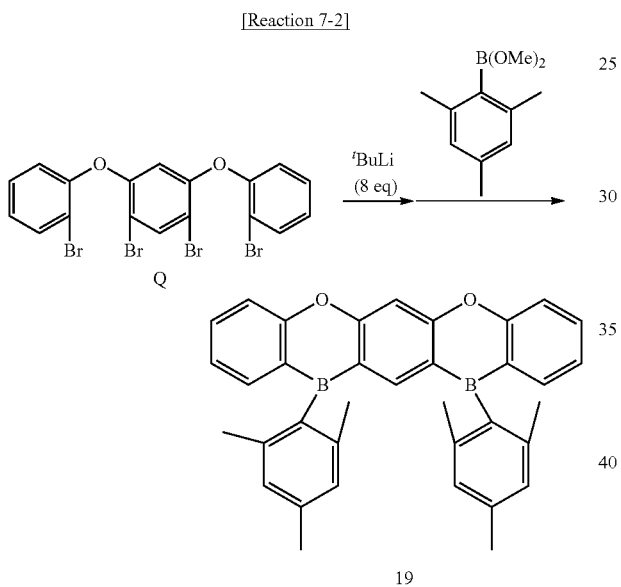

19

Under an argon atmosphere, to a 2,000 ml, three-neck flask, 800 ml of a dehydrated THE solution of 11.55 g (20.0 mmol) of Compound Q was added and stirred at about −80° C. 84 ml (160 mmol) of 1.9 M t-BuLi pentane solution was dropwise added thereto and stirred for about 2 hours. Then, stirring was performed for about 3 hours while elevating the temperature to about −10° C. The temperature was decreased to about −80° C. again and 80 ml of a dehydrated THF solution of 7.68 g (40 mmol) of 2,4,6-trimethylboronic acid methyl ester was added thereto dropwise, followed by stirring for about 2 hours at about −80° C. and then for about 3 hours at room temperature. After finishing the reaction, the reaction mixture was washed with water. The organic phase thus obtained was concentrated to obtain a viscous material. The crude product thus obtained was separated by silica gel column chromatography to obtain 5.49 g (yield 53%) of white solid Compound 19. The molecular weight of Compound 19 as measured by FAB-MS was 518. The chemical shift values δ of Compound 19 measured by 1H-NMR ($CDCl_3$) were [7.71 (2H), 7.35 (2H), 7.25 (1H), 7.09-6.95 (8H), 6.65 (1H), 2.33 (12H), 2.18 (6H)].

(8) Synthetic of Compound 13

Compound 13 which is a polycyclic compound according to an example embodiment, may be synthesized, for example, by the following Reaction 8:

[Reaction 8]

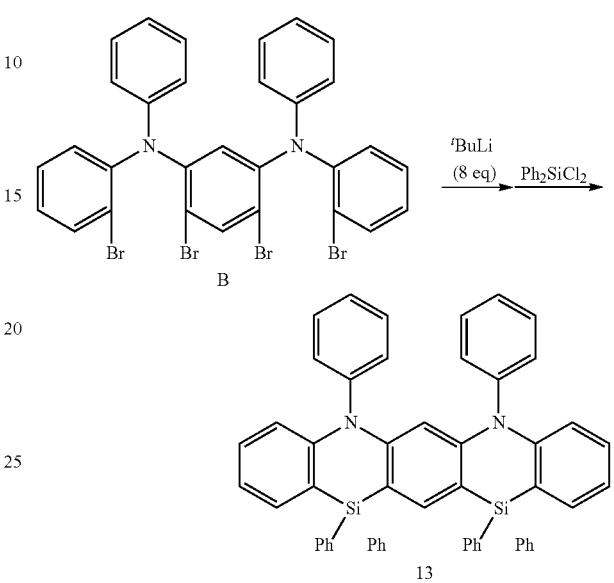

13

Under an argon atmosphere, to a 300 ml, three-neck flask, 128 ml of a dehydrated THE solution of 2.35 g (3.2 mmol) of Compound B was added and stirred at about −80° C. 13.5 ml (25.7 mmol) of 1.9 M t-BuLi pentane solution was dropwise added thereto and stirred for about 2 hours. Then, stirring was performed for about 3 hours while elevating the temperature to about −10° C. The temperature was decreased to about −80° C. again and 13 ml of a dehydrated THF solution of 1.65 g (6.5 mmol) of diphenyldichlorosilane was added thereto dropwise, followed by stirring for about 2 hours at about −80° C. and then for about 3 hours at room temperature. After finishing the reaction, the reaction mixture was washed with water. The organic phase thus obtained was concentrated to obtain a viscous material. The crude product thus obtained was separated by silica gel column chromatography to obtain 1.14 g (yield 46%) of white solid Compound 13. The molecular weight of Compound 13 as measured by FAB-MS was 772. The chemical shift values δ of Compound 13 measured by 1H-NMR ($CDCl_3$) were [7.74 (2H), 7.48-7.36 (24H), 7.30-7.22 (6H), 7.10-7.01 (9H)].

(9) Synthetic of Compound 21

Compound 21 which is a polycyclic compound according to an example embodiment, may be synthesized, for example, by the following Reaction 9:

[Reaction 9]

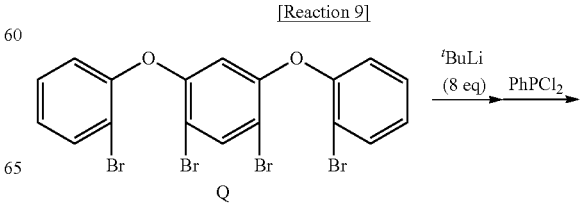

-continued

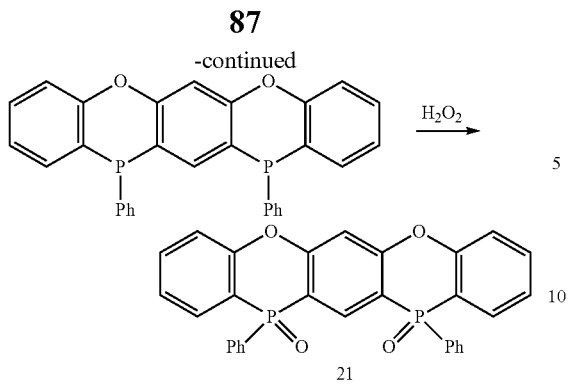

21

Under an argon atmosphere, to a 2,000 ml, three-neck flask, 11.55 g (20.0 mmol) of Compound Q, and 800 ml of a dehydrated THF solution were added and stirred at about −80° C. 84 ml (160 mmol) of 1.9 M t-BuLi pentane solution was dropwise added thereto and stirred for about 2 hours. Then, stirring was performed for about 3 hours while elevating the temperature to about −10° C. The temperature was decreased to about −80° C. again and 80 ml of a dehydrated THF solution of 7.16 g (40 mmol) of phenyldichlorophosphine was added thereto dropwise, followed by stirring for about 2 hours at about −80° C. and then for about 3 hours at room temperature. After finishing the reaction, the reaction mixture was washed with water. The organic phase thus obtained was concentrated to obtain a viscous material. The crude product thus obtained was separated by silica gel column chromatography to obtain a white solid compound.

Then, to a 300 ml, round-bottom flask, the white solid, 200 ml of dichloromethane and 40 ml of 35% aqueous hydrogen peroxide solution were added and stirred for about 1 hour for reaction. After finishing the reaction, water was added, an organic layer was separated and taken, and solvents were removed by distillation. The crude product thus obtained was separated by silica gel column chromatography to obtain 4.46 g (yield 44%) of white solid Compound 21. The molecular weight of Compound 21 as measured by FAB-MS was 506. The chemical shift values δ of Compound 21 measured by 1H-NMR (CDCl₃) were [8.24 (1H), 7.79-7.71 (6H), 7.62-7.49 (8H), 7.25-7.18 (4H), 7.05 (1H)].

(10) Synthetic of Compound 9

Compound 9 which is a polycyclic compound according to an example embodiment, may be synthesized, for example, by the following Reaction 10:

[Reaction 10]

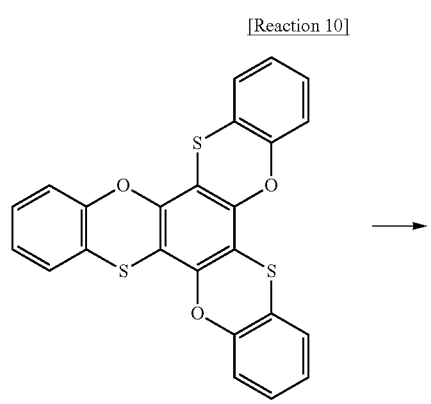

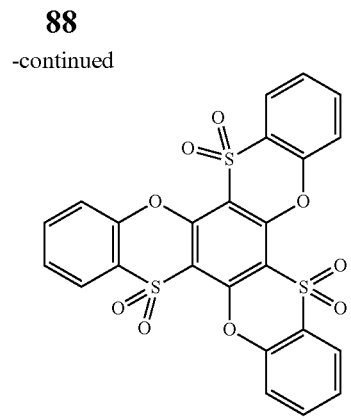

9

To a 200 ml, round-bottom flask, 3.0 g (6.7 mmol) of bis [1,4] benzoxathiino [2,3-a: 2',3'-c] phenoxathiin, 20 ml of acetic acid and 20 ml of 35% aqueous hydrogen peroxide solution were added, followed by stirring while heating and refluxing for about 16 hours for the reaction. After finishing the reaction, chloroform was added, an organic layer was separately taken, and solvents were removed by distillation. The crude product thus obtained was separated by silica gel column chromatography to obtain 3.08 g (yield 85%) of white solid Compound 9. The molecular weight of Compound 9 as measured by FAB-MS was 540. The chemical shift values δ of Compound 9 measured by 1H-NMR (CDCl₃) were [7.72 (3H), 7.35 (3H), 7.24-7.15 (6H)].

2. Manufacture and Evaluation of Organic Electroluminescence Device Including a Polycyclic Compound 2-1. Example a of Organic Electroluminescence Device Including Polycyclic Compound (Manufacture of Organic Electroluminescence Devices)

Organic electroluminescence devices of example embodiments including the polycyclic compounds of example embodiments in an emission layer that emits delayed fluorescence were manufactured by a method described below. For example, an organic electroluminescence device according to an example embodiment in which an emission layer includes the polycyclic compound according to an example embodiment as a dopant emitting delayed fluorescence and further includes a host for delayed fluorescence, will be explained. Organic electroluminescence devices of Example 1 to Example 6 were manufactured using each of the polycyclic compounds, Compounds 2, 8, 50, 76, 77 and 31 was used as the dopant material of an emission layer. Comparative Example 1 to Comparative Example 3 corresponded to organic electroluminescence devices manufactured by using Comparative Compound C1 to Comparative Compound C3 as the dopant material of an emission layer. The compounds used in Example 1 to Example 6 and Comparative Example 1 to Comparative Example 3 are listed in Table 1 below.

TABLE 1
Compound 2
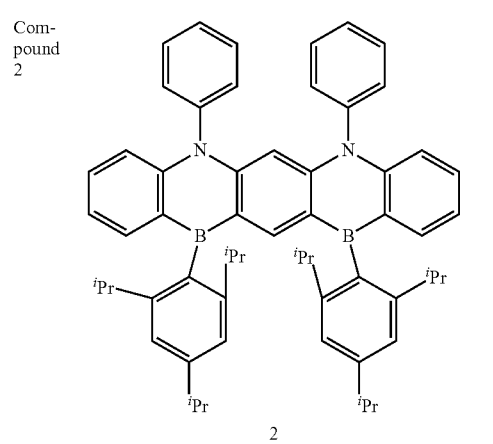
2
Compound 8
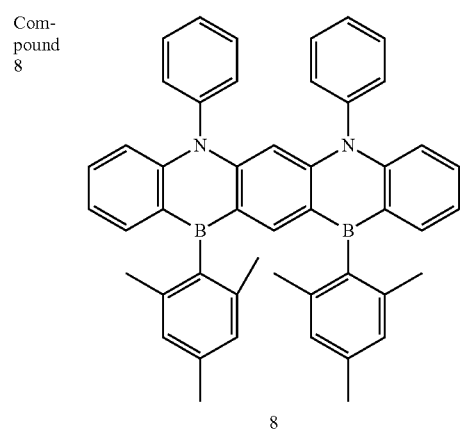
8
Compound 50
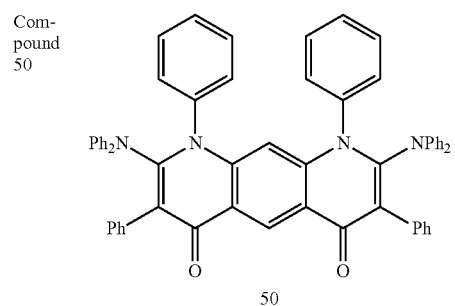
50
Compound 76
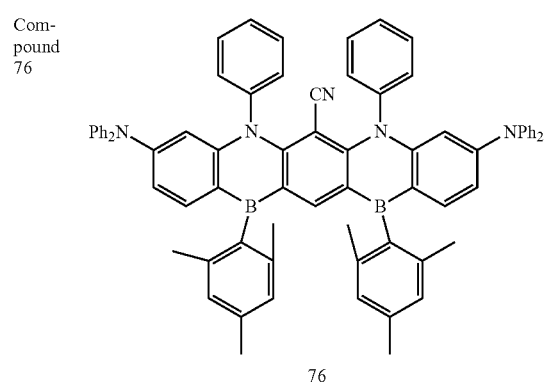
76
TABLE 1-continued
Compound 77
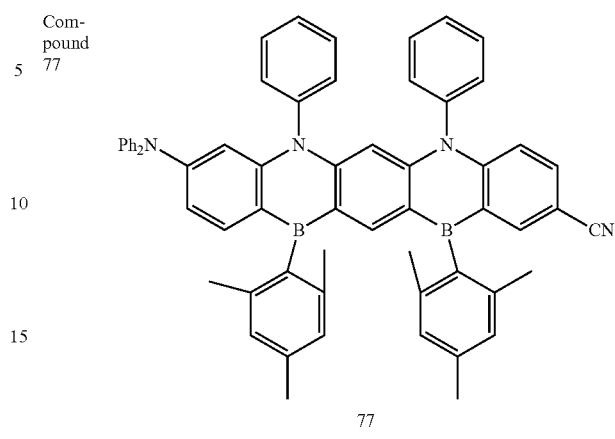
77
Compound 31
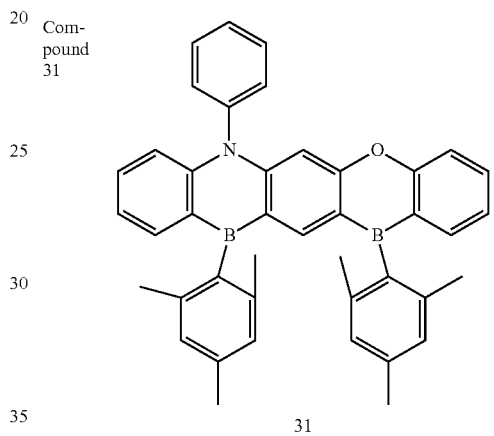
31
Comparative Compound C1
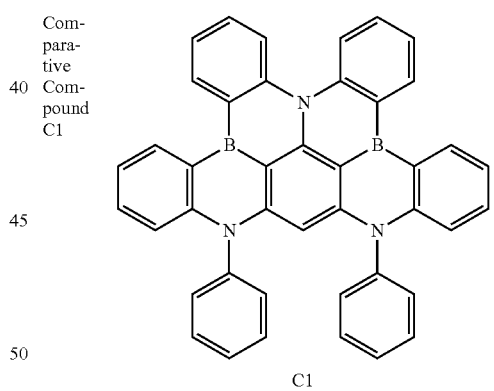
C1
Comparative Compound C2
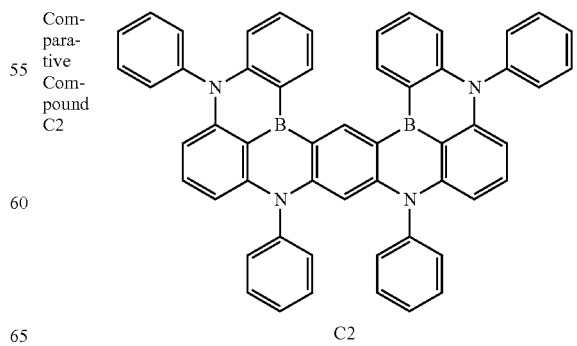
C2

TABLE 1-continued

| Comparative Compound C3 | 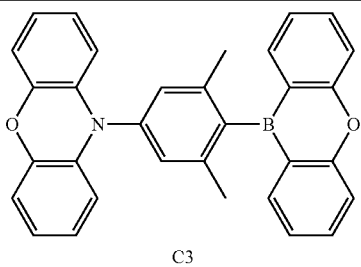 |
|---|---|
| | C3 |

On a glass substrate, ITO was patterned to a thickness of about 1,500 Å and washed with ultra-pure water, and a UV ozone treatment was conducted for about 10 minutes. Then, HAT-CN was deposited to a thickness of about 100 Å, a-NPD was deposited to a thickness of about 400 Å, and mCP was deposited to a thickness of about 50 Å to form a hole transport region. Then, the polycyclic compound according to an example embodiment and the Comparative Compound each, and DPEPO were co-deposited in a ratio of 20:80 to form an emission layer to a thickness of about 200 Å. Then, a layer with a thickness of about 100 Å was formed using DPEPO. That is, in order to form the emission layer by the co-deposition, each of Compounds 2, 8, 50, 76, 77 and 31 was mixed with DPEPO and deposited in Example 1 to Example 6, and each of Comparative Compound C1 to Comparative Compound C3 was mixed with DPEPO and deposited in Comparative Example 1 to Example 3.

Then, on the emission layer, a layer was formed using DPEPO to a thickness of about 100 Å on the emission layer, a layer was formed using TPBi to a thickness of about 300 Å, and a layer was formed using LiF to a thickness of about 20 Å to form an electron transport region. Then, a second electrode was formed using aluminum ($A^1$) to a thickness of about 1,000 Å.

In the examples, the hole transport region, the emission layer, the electron transport region and the second electrode were formed by using a vacuum deposition apparatus.
(Evaluation of properties of organic electroluminescence device)

The evaluation results of the organic electroluminescence devices of Example 1 to Example 6 and Comparative Example 1 to Comparative Example 3 are shown in Table 2. In Table 2, the emission efficiency, the device life and the half-width of emitted light of the organic electroluminescence devices thus manufactured were compared and shown.

In the properties evaluation results on the Examples and the Comparative Examples as shown in Table 2, device efficiency represents current efficiency values on a current density of 10 $mA/cm^2$, and device life represents half life representing time required for decreasing the luminance from an initial luminance of 1,000 $cd/m^2$ to half. The half-width represents full width at half maximum (FWHM) in an emission region.

TABLE 2

| Device manufacturing example | Emission layer dopant material | Efficiency (cd/A) | Device life LT50 (h) | Half-width (nm) |
|---|---|---|---|---|
| Example 1 | Compound 2 | 114 | 514 | 27 |
| Example 2 | Compound 8 | 111 | 369 | 28 |
| Example 3 | Compound 50 | 117 | 226 | 32 |

TABLE 2-continued

| Device manufacturing example | Emission layer dopant material | Efficiency (cd/A) | Device life LT50 (h) | Half-width (nm) |
|---|---|---|---|---|
| Example 4 | Compound 76 | 108 | 334 | 32 |
| Example 5 | Compound 77 | 119 | 364 | 29 |
| Example 6 | Compound 31 | 105 | 450 | 26 |
| Comparative Example 1 | Comparative Compound C1 | 98 | 19 | 36 |
| Comparative Example 2 | Comparative Compound C2 | 96 | 16 | 34 |
| Comparative Example 3 | Comparative Compound C3 | 100 | 100 | 77 |

Referring to the results of Table 2, it was found that the organic electroluminescence devices of the Examples, which used the polycyclic compounds according to example embodiments as a material for an emission layer, showed better device life characteristic and higher device efficiency when compared with the Comparative Examples, which used the comparative compounds in an emission layer. The Examples showed narrower half-width characteristic when compared with the Comparative Examples.

2-2. Example B of Organic Electroluminescence Device Including Polycyclic Compound Organic electroluminescence devices of example embodiments including the polycyclic compounds of example embodiments in an emission layer that emits delayed fluorescence were manufactured by a method described below. For example, an organic electroluminescence device according to an example embodiment in which an emission layer includes the polycyclic compound according to an example embodiment as a host emitting delayed fluorescence and further includes a dopant for delayed fluorescence, will be explained. Organic electroluminescence devices of Example 7 to Example 10 were manufactured using each of the polycyclic compounds, Compounds 19, 13, 21 and 9 as the host material of a delayed fluorescence emission layer. Comparative Example 4 and Comparative Example 5 corresponded to organic electroluminescence devices manufactured by using Comparative Compound C4 and Comparative Compound C5 as the host material of an emission layer.

The compounds used in Example 7 to Example 10 and Comparative Example 4 and Comparative Example 5 are listed in Table 3 below.

TABLE 3

Compound 19

19

TABLE 3-continued

Compound 13

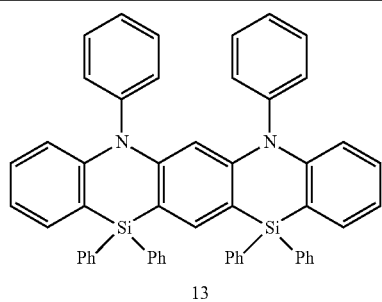

13

Compound 21

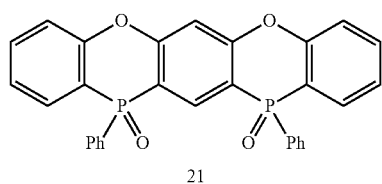 [SMILES: O=P1(c2ccccc2)c2ccccc2Oc2cc3c(cc21)P(=O)(c1ccccc1)c1ccccc1O3]

21

Compound 9

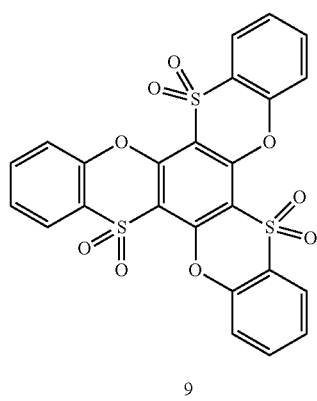 [SMILES: O=S1(=O)c2ccccc2Oc2c1c1c(c3c2S(=O)(=O)c2ccccc2O3)S(=O)(=O)c2ccccc2O1]

9

Comparative Compound C4

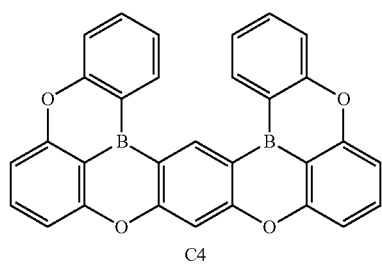

C4

Comparative Compound C5

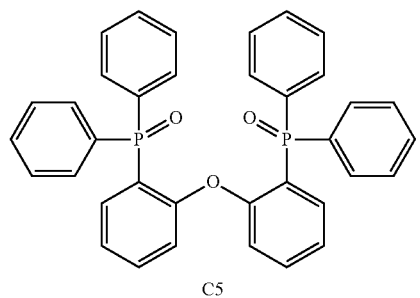

C5

(Manufacture of Organic Electroluminescence Device)

On a glass substrate, ITO was patterned to a thickness of about 1,500 Å and washed with ultra-pure water, and a UV ozone treatment was conducted for about 10 minutes. Then, HAT-CN was deposited to a thickness of about 100 Å, 4,4'-bis [N-(1-naphthyl)-N-phenylamino]biphenyl (NPB) was deposited to a thickness of about 400 Å, and mCP was deposited to a thickness of about 50 Å to form a hole transport region.

Then, an emission layer including the polycyclic compound according to an example embodiment or the comparative compound was formed on the hole transport region. The emission layer was formed by co-depositing the polycyclic compound according to an example embodiment or the Comparative Compound each, and 10-phenyl-10H,10'H-spiro [acridine-9,9'-anthracen]-10'-one (ACRSA) as a dopant material in a weight ratio of 82:18 to a thickness of about 200 Å. That is, the emission layer formed by the co-deposition was formed by mixing Compound 19, 13, 21 and 9 in Example 7 to Example 10, respectively, with ACRSA and depositing, and by mixing Comparative Compound C4 and Comparative Compound C5 in Comparative Example 4 and Comparative Example 5, respectively, with ACRSA and depositing.

Then, on the emission layer, a layer was formed using DPEPO to a thickness of about 100 Å, a layer was formed using TPBi to a thickness of about 300 Å, and a layer was formed using Liq to a thickness of about 20 Å to form an electron transport region. Then, a second electrode was formed using aluminum ($A^1$) to a thickness of about 1,000 Å.

In the Examples, the hole transport region, the emission layer, the electron transport region and the second electrode were formed by using a vacuum deposition apparatus.

(Evaluation of Properties of Organic Electroluminescence Device)

The evaluation results of the organic electroluminescence devices of Example 7 to Example 10 and Comparative Example 4 and Comparative Example 5 are shown in Table 4. In Table 4, the driving voltage, the emission efficiency and the device life of the organic electroluminescence devices thus manufactured are compared and shown.

In the properties evaluation results on the examples and the comparative examples as shown in Table 4, relative values are listed with the driving voltage, device efficiency and device life of Comparative Example 5 as reference. The device efficiency represents current efficiency values on a current density of 10 mA/cm², and device life represents half life representing time required for decreasing the luminance from an initial luminance of 1,000 cd/m² to half.

TABLE 4

| Device manufacturing example | Emission layer host material | Driving voltage (%) | Efficiency (%) | Device life (%) |
|---|---|---|---|---|
| Example 7 | Compound 19 | 86 | 108 | 371 |
| Example 8 | Compound 13 | 45 | 115 | 810 |
| Example 9 | Compound 21 | 64 | 120 | 433 |
| Example 10 | Compound 9 | 85 | 130 | 198 |
| Comparative Example 4 | Comparative Compound C4 | 92 | 93 | 89 |
| Comparative Example 5 | Comparative Compound C5 | 100 | 100 | 100 |

Referring to Table 4, it was found that the organic electroluminescence device according to an example embodiment using the polycyclic compound according to an example embodiment as a host material of a delayed fluorescence emission layer showed higher emission efficiency and longer life when compared with Comparative Example 4 and Comparative Example 5. The Examples showed lower driving voltage than the Comparative Examples.

2-3. Example C of Organic Electroluminescence Device Including Polycyclic Compound Organic electroluminescence devices of example embodiments including the polycyclic compounds of example embodiments in an emission layer that emits phosphorescence were manufactured by a method described below. For example, an organic electroluminescence device according to an example embodiment in which an emission layer includes the polycyclic compound according to an example embodiment as a host emitting phosphorescence and further includes a dopant for phosphorescence, will be explained. Organic electroluminescence devices of Example 11 to Example 14 were manufactured using each of the polycyclic compounds, Compounds 19, 13, 21 and 9 as the host material of a phosphorescence emission layer. Comparative Example 6 and Comparative Example 7 corresponded to organic electroluminescence devices manufactured by using Comparative Compound C4 and Comparative Compound C5, respectively, as the host material of an emission layer that emits phosphorescence.

The compounds used in Example 11 to Example 14 and Comparative Example 6 and Comparative Example 7 are listed in Table 3.

(Manufacture of Organic Electroluminescence Device)

On a glass substrate, ITO was patterned to a thickness of about 1,500 Å and washed with ultra-pure water, and a UV ozone treatment was conducted for about 10 minutes. Then, HAT-CN was deposited to a thickness of about 100 Å, 4,4'-bis [N-(1-naphthyl)-N-phenylamino]biphenyl (NPB) was deposited to a thickness of about 400 Å, and mCP was deposited to a thickness of about 50 Å to form a hole transport region.

Then, an emission layer including the polycyclic compound according to an example embodiment or the Comparative Compound was formed on the hole transport region. The emission layer was formed by co-depositing the polycyclic compound according to an example embodiment or the comparative compound with FIrpic dopant material in a weight ratio of 92:8 to a thickness of about 200 Å. That is, the emission layer formed by the co-deposition was formed by mixing Compound 19, 13, 21 and 9 in Example 11 to Example 14, respectively, with FIrpic and depositing, and by mixing Comparative Compound C4 and Comparative Compound C5 in Comparative Example 6 and Comparative Example 7, respectively, with FIrpic and depositing.

Then, on the emission layer, a layer was formed using DPEPO to a thickness of about 100 Å, a layer was formed using TPBi to a thickness of about 300 Å, and a layer was formed using Liq to a thickness of about 20 Å to form an electron transport region. Then, a second electrode was formed using aluminum ($A^1$) to a thickness of about 1,000 Å.

In the Examples, the hole transport region, the emission layer, the electron transport region and the second electrode were formed by using a vacuum deposition apparatus.

(Evaluation of Properties of Organic Electroluminescence Device)

The evaluation results of the organic electroluminescence devices of Example 11 to Example 14 and Comparative Example 6 and Comparative Example 7 are shown in Table 5. In Table 5, the driving voltage, the emission efficiency and the device life of the organic electroluminescence devices thus manufactured are compared and shown.

In the properties evaluation results on the examples and the comparative examples as shown in Table 5, relative values are listed with the driving voltage, device efficiency and device life of Comparative Example 7 as references. The device efficiency represents current efficiency values on a current density of 10 $mA/cm^2$, and device life represents half life representing time required for decreasing the luminance from an initial luminance of 1,000 $cd/m^2$ to half.

TABLE 5

| Device manufacturing example | Emission layer host material | Driving voltage (%) | Efficiency (%) | Device life (%) |
|---|---|---|---|---|
| Example 11 | Compound 19 | 82 | 111 | 194 |
| Example 12 | Compound 13 | 72 | 110 | 931 |
| Example 13 | Compound 21 | 69 | 123 | 634 |
| Example 14 | Compound 9 | 59 | 129 | 252 |
| Comparative Example 6 | Comparative Compound C4 | 89 | 89 | 28 |
| Comparative Example 7 | Comparative Compound C5 | 100 | 100 | 100 |

Referring to Table 5, it was found that the organic electroluminescence device according to an example embodiment using the polycyclic compound according to an example embodiment as a host material of a phosphorescence emission layer showed higher emission efficiency and longer life when compared with Comparative Example 6 and Comparative Example 7. The Examples showed lower driving voltage than the Comparative Examples.

As demonstrated by the Examples, a polycyclic compound according to an example embodiment may be used as the host or dopant material of a delayed fluorescence emission layer or the host material of a phosphorescence emission layer. A polycyclic compound according to an example embodiment may include a carbonyl group, a sulfonyl group, a phosphoryl group, or a silyl group, which is highly chemically stable, or a substituted boron group, which has steric hindrance as an electron acceptor moiety, and may show improved device life when compared with the Comparative Examples.

By way of summation and review, to provide an organic electroluminescence device with high efficiency, techniques on phosphorescence emission, which uses energy in a triplet state, or delayed fluorescence emission, which uses the generating phenomenon of singlet excitons by the collision of triplet excitons (triplet-triplet annihilation, TTA), are being considered. A material for thermally activated delayed fluorescence (TADF) using delayed fluorescence phenomenon is being considered.

As described above, a polycyclic compound according to an example embodiment may exhibit high mobility and a high triplet (T1) energy level, and may show improved emission efficiency.

An organic electroluminescence device according to an example embodiment may show improved device properties including a low driving voltage, long life, and high emission efficiency.

A polycyclic compound according to an example embodiment may be applied in the emission layer of an organic electroluminescence device to improve the life and efficiency of the organic electroluminescence device.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic electroluminescence device, comprising:
a first electrode;
a hole transport region on the first electrode;
an emission layer on the hole transport region, the emission layer including a condensed polycyclic compound of three or more six-membered rings, at least two six-membered rings among the six-membered rings including an electron donor moiety and an electron acceptor moiety at facing positions, respectively, the at least two six-membered rings not being immediately adjacent to each other;
an electron transport region on the emission layer; and
a second electrode on the electron transport region,
wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and oxides thereof,
wherein the polycyclic compound is represented by any one among Formula 1 to Formula 3:

[Formula 1]

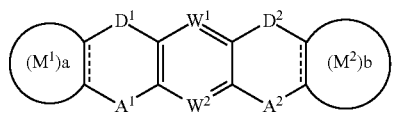

[Formula 2]

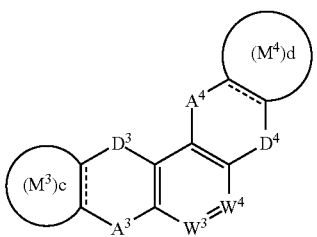

[Formula 3]

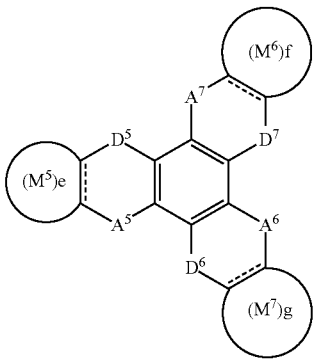

in Formula 1 to Formula 3,
$A^1$ to $A^7$ are each independently CO, $BR_1$, $SiR_2R_3$, $GeR_4R_5$, $POR_6$, $PSR_7$, SO, or $SO_2$,
$D^1$ to $D^7$ are each independently $NR_8$, O, S, or Se,
$W^1$ to $W^4$ are each independently N or $CR_9$,
a to g are each independently 0 or 1, rings $M^1$ to $M^7$ are each independently a substituted or unsubstituted aryl group having 6 to 30 ring carbon atoms, or a substituted or unsubstituted heteroaryl group having 2 to 30 ring carbon atoms,
$R^1$ to $R^8$ are each independently a hydrogen atom, a deuterium atom, a halogen atom, a cyano group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms,
$R^9$ is a hydrogen atom, a deuterium atom, a halogen atom, a cyano group, a phosphine oxide group, a phosphine sulfide group, a carbonyl group, a boron group, a substituted or unsubstituted oxy group, a substituted or unsubstituted thiol group, a substituted or unsubstituted amino group, a substituted or unsubstituted silyl group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms,
when $D_3$ is $NR_8$ and $A^3$ and $A^4$ are CO, $D^4$ is $NR_8$, O, or Se,
when $D^5$ to $D^7$ are $NR_8$, at least one Ra is a halogen atom, a cyano group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms,
when, in Formula 1, $W^1$ and We are each $CR_9$, $A^1$ and $A^2$ are each $BR_1$, $D^1$ and $D^2$ are each $NR_8$, and rings $M^1$ and $M^2$ are each a substituted or unsubstituted phenyl group, at least one selected from $R^1$, $R^9$, and rings $M^1$ and $M^2$ is substituted with a halogen atom, and
when $M^1$ and $M^2$ in Formula 1 are each a six-membered ring, i) $D^1$ and $D^2$ are each not $NR_8$, or ii) at least one selected from $A^1$ and $A^2$ is $BR_1$, $SiR_2R_3$, $GeR_4R_5$, $POR_6$, or $PSR_7$, and when $M^3$ and $M^4$ in Formula 2 are each a six-membered ring, iii) $D^3$ and $D^4$ are each not $NR_8$, or iv) at least one selected from $A^3$ and $A^4$ is $BR_1$, $SiR_2R_3$, $GeR_4R_5$, $POR_6$, or $PSR_7$.

2. The organic electroluminescence device as claimed in claim 1, wherein:
the emission layer is a delayed fluorescence emission layer including a host and a dopant, and
the host or the dopant includes the polycyclic compound.

3. The organic electroluminescence device as claimed in claim 1, wherein:
the emission layer is a phosphorescence emission layer including a host and a dopant, and
the host includes the polycyclic compound.

4. The organic electroluminescence device as claimed in claim 1, wherein the electron donor moiety includes an amine group, an oxygen atom, a sulfur atom, or a selenium atom.

5. The organic electroluminescence device as claimed in claim 1, wherein the electron acceptor moiety includes a carbonyl group, a boron group, a silyl group, a germyl group, a phosphine oxide group, a phosphine sulfide group, a sulfoxide group, or a sulfur dioxide group.

6. The organic electroluminescence device as claimed in claim 1, wherein the emission layer emits blue light.

7. The organic electroluminescence device as claimed in claim 1, wherein $A^1$ to $A^7$ are represented by the following Formula 4:

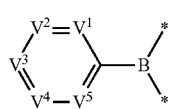

[Formula 4]

in Formula 4, $V^1$ to $V^5$ are each independently N, $CR_{10}$, or $CR_{11}$, provided that at least one among $V^1$ to $V^5$ is $CR_{11}$, $R_{10}$ is a hydrogen atom, a deuterium atom, a halogen atom, a cyano group, a phosphine oxide group, a phosphine sulfide group, a carbonyl group, a boron group, a substituted or unsubstituted oxy group, a substituted or unsubstituted thiol group, a substituted or unsubstituted amino group, a substituted or unsubstituted silyl group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and $R_{11}$ is a cyano group, a substituted or unsubstituted oxy group, a substituted or unsubstituted thiol group, a substituted or unsubstituted amino group, a substituted or unsubstituted silyl group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

8. The organic electroluminescence device as claimed in claim 1, wherein Formula 1 to Formula 3 are represented by the following Formula 1-1 to Formula 1-3, respectively:

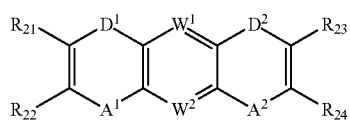

[Formula 1-1]

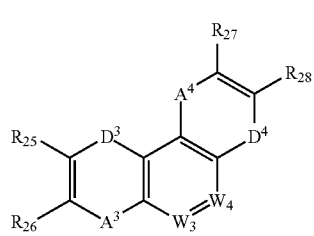

[Formula 1-2]

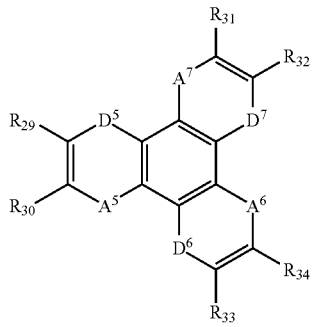

[Formula 1-3]

in Formulae 1-1 to 1-3, $R_{21}$ to $R_{34}$ are each independently a hydrogen atom, a deuterium atom, a halogen atom, a cyano group, a phosphine oxide group, a phosphine sulfide group, a silyl group, a carbonyl group, a boron group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and $A^1$ to $A^7$, $D^1$ to $D^7$, and $W^1$ to $W^4$ are the same as defined in Formula 1 to Formula 3.

9. The organic electroluminescence device as claimed in claim 1, wherein Formula 1 to Formula 3 are represented by the following Formula 2-1 to Formula 2-3, respectively:

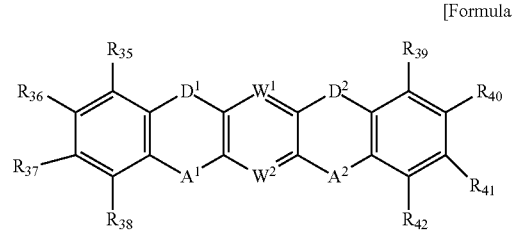

[Formula 2-1]

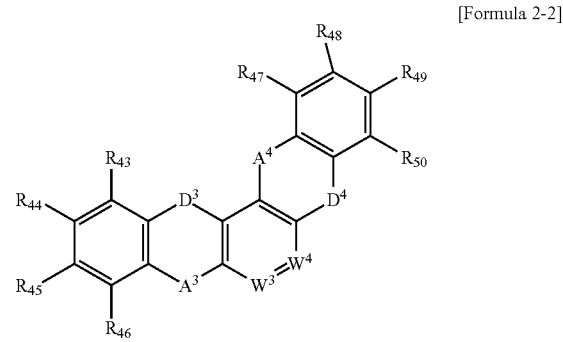

[Formula 2-2]

[Formula 2-3]

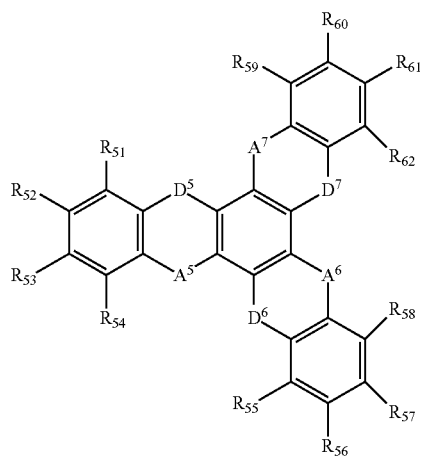

in Formula 2-1 to Formula 2-3, $R_{35}$ to $R_{62}$ are each independently a hydrogen atom, a deuterium atom, a halogen atom, a cyano group, a phosphine oxide group, a phosphine sulfide group, a silyl group, a carbonyl group, a boron group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and $A^1$ to $A^7$, $D^1$ to $D^7$, and $W^1$ to $W^4$ are the same as defined in Formula 1 to Formula 3.

10. The organic electroluminescence device as claimed in claim 1, wherein the condensed polycyclic compound in the emission layer includes at least one compound among compounds represented in the following Compound Group 1:

[Compound Group 1]

3

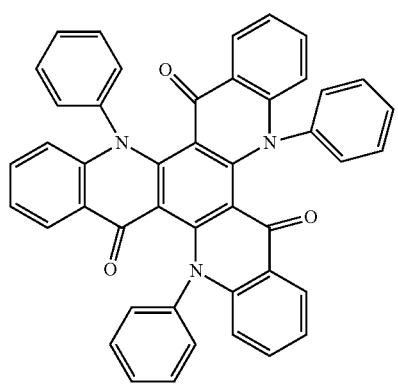

6

7

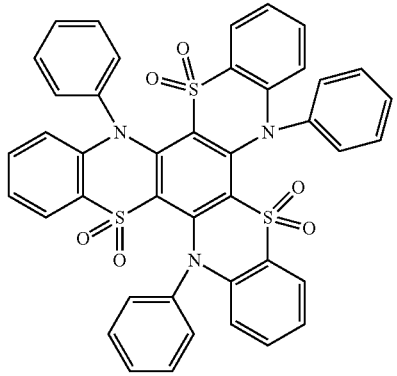

9

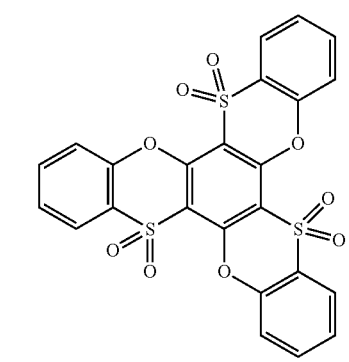

11

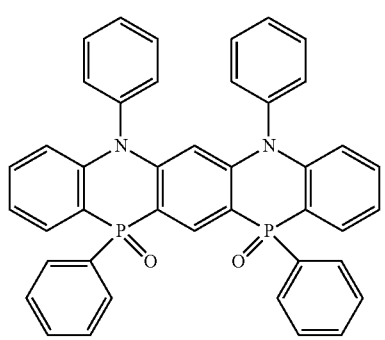

12

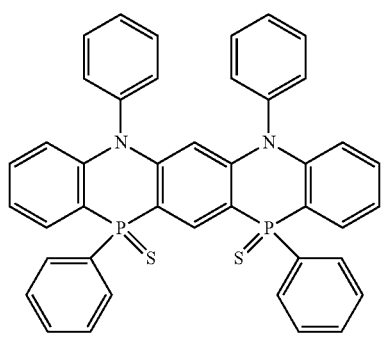

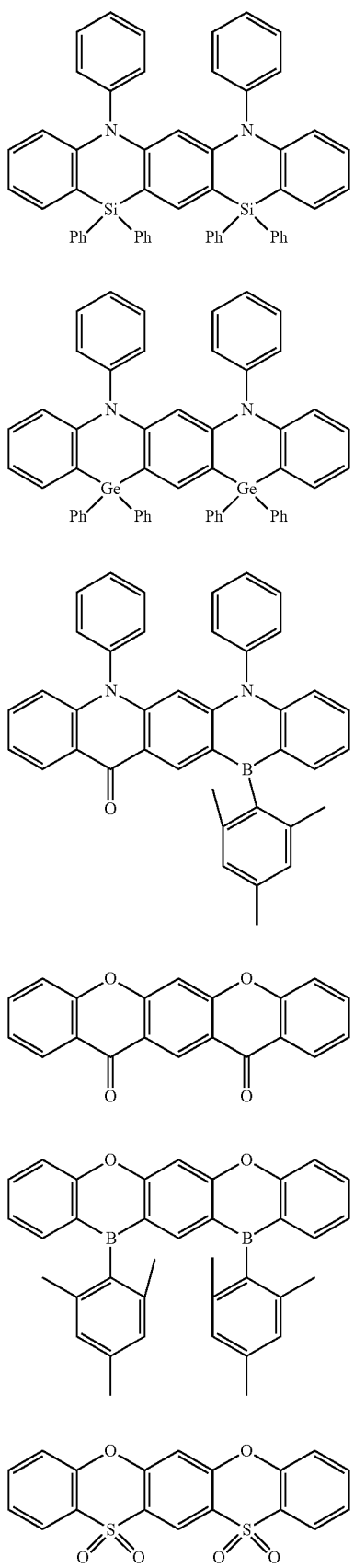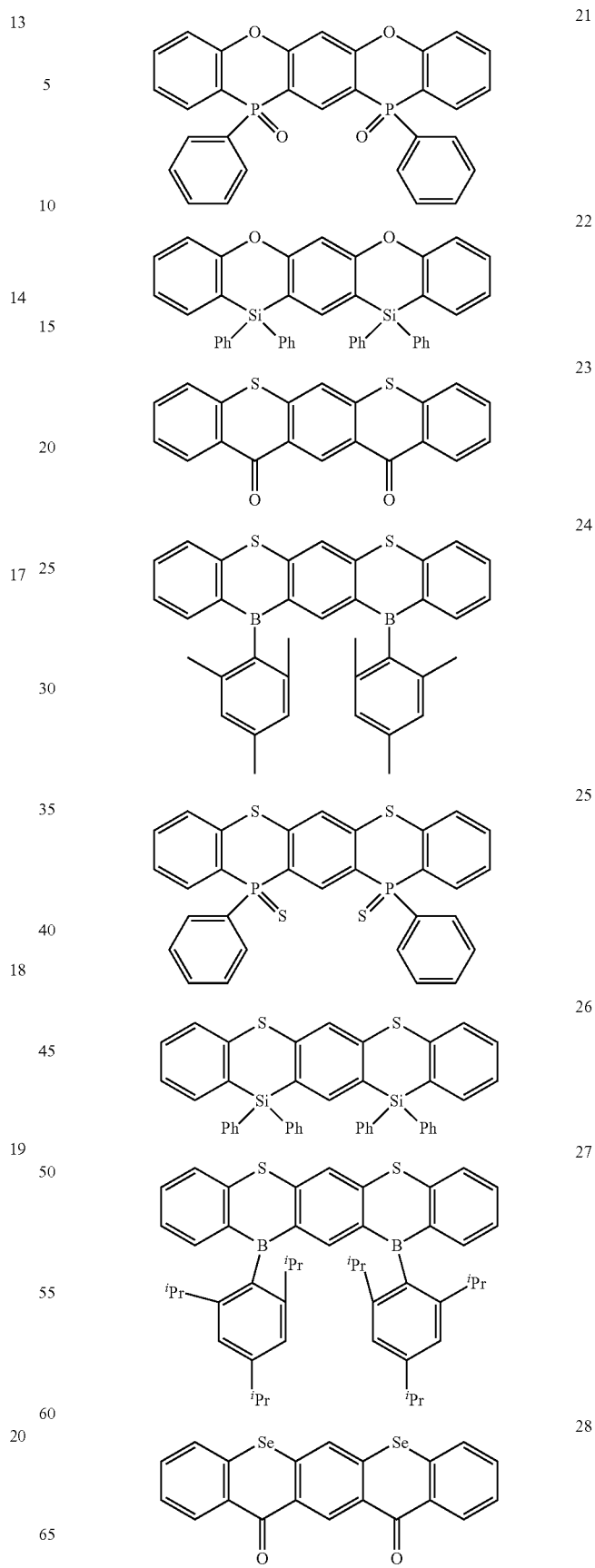

29
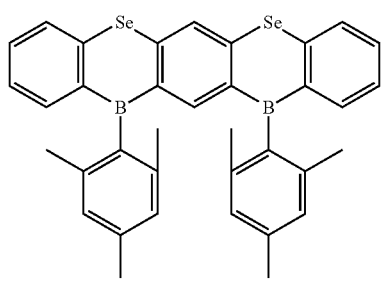
31
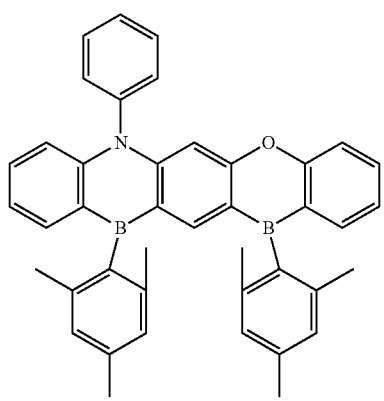
32
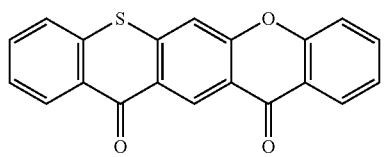
33
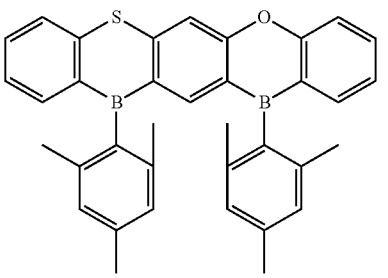
34
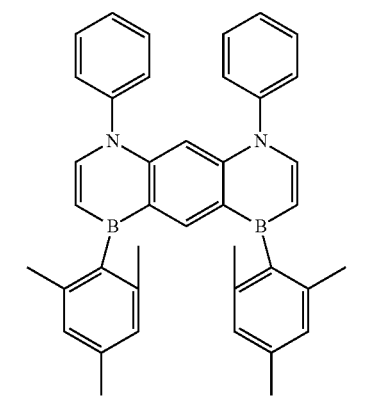
35
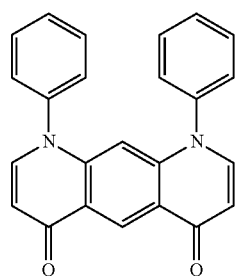
36
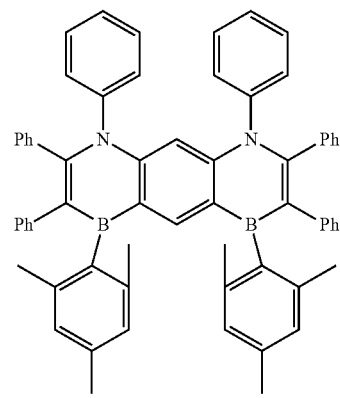
37
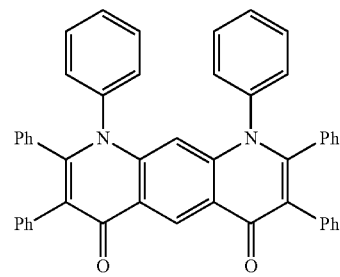
38
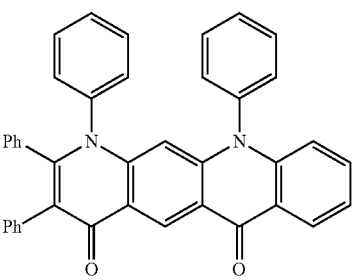
39
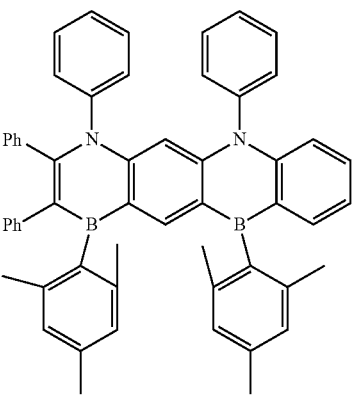

41
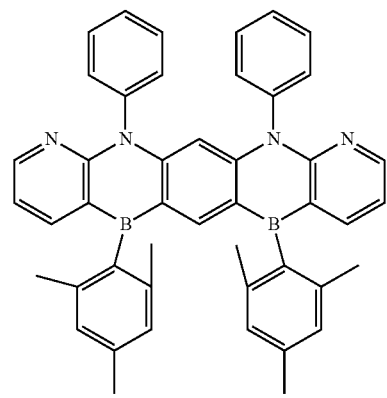
42
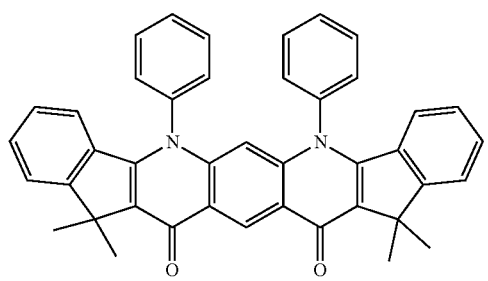
43
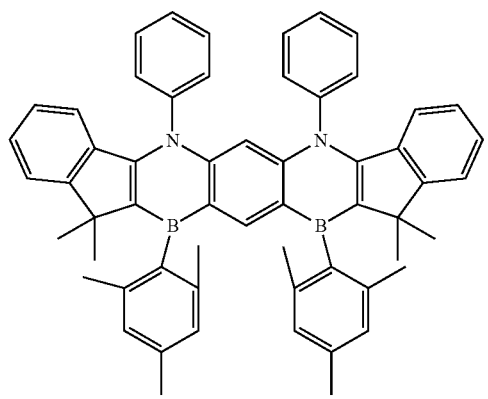
47
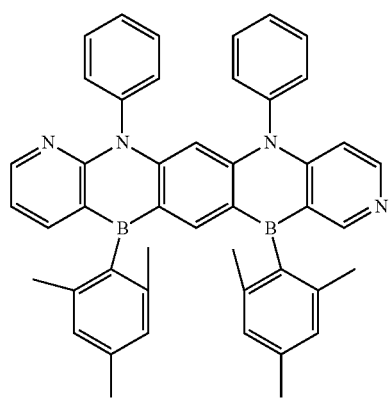
48
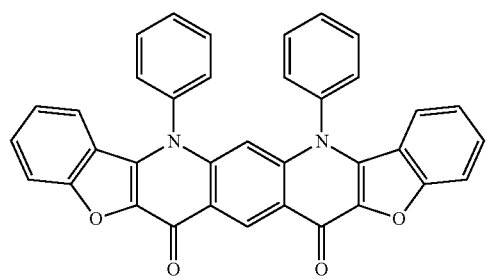
49
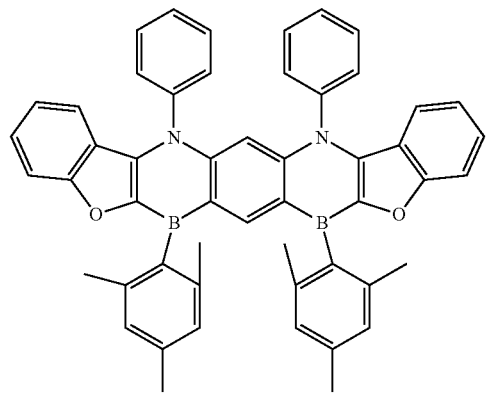
50
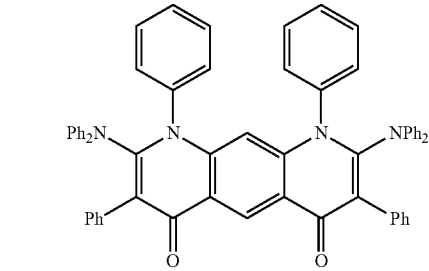
51
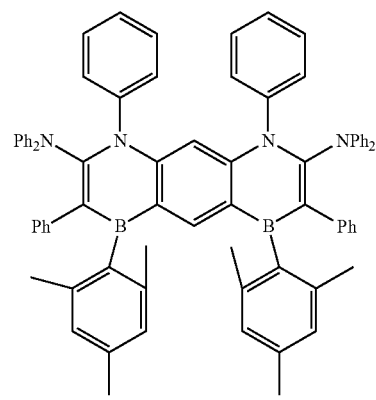
52
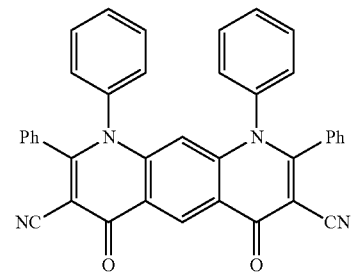

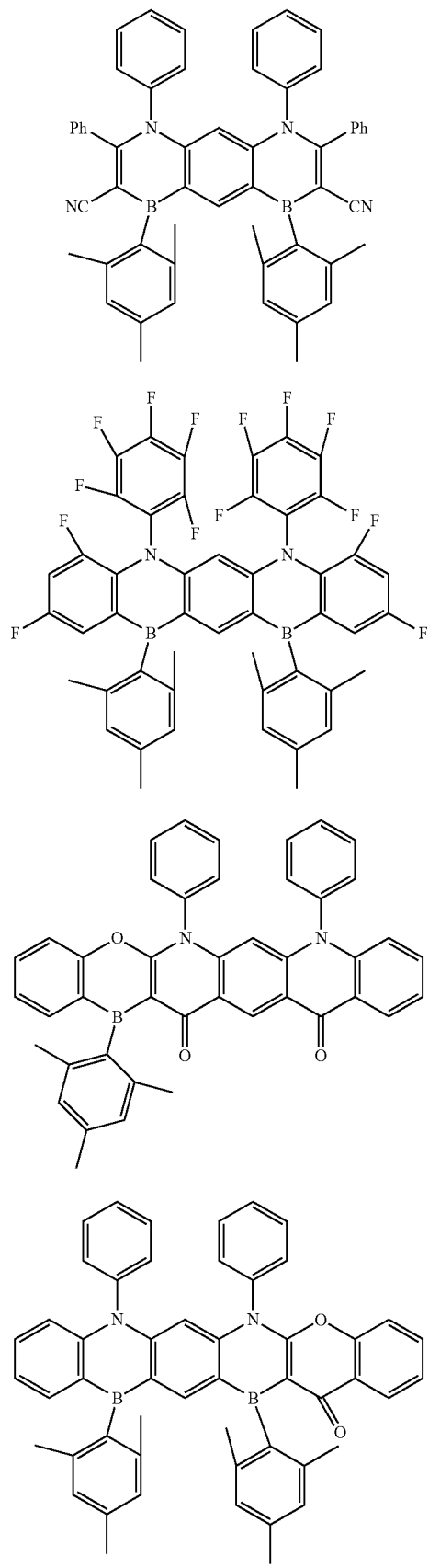
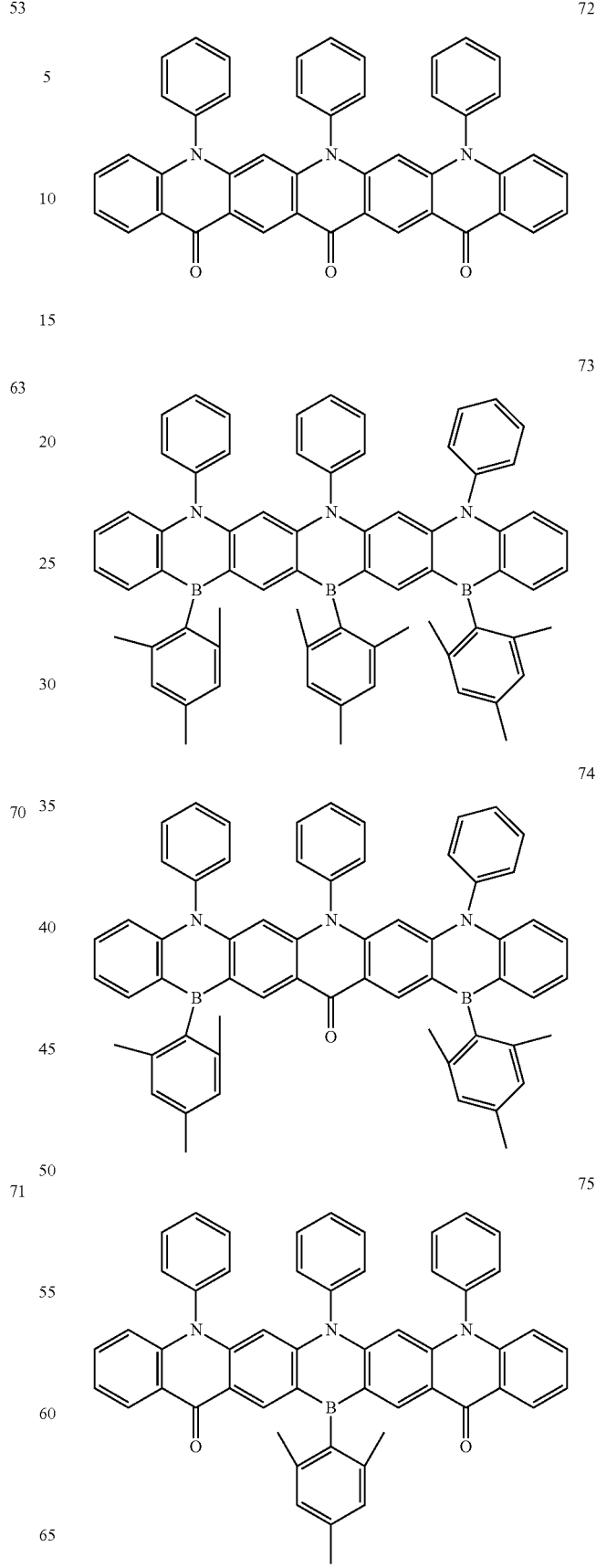

82 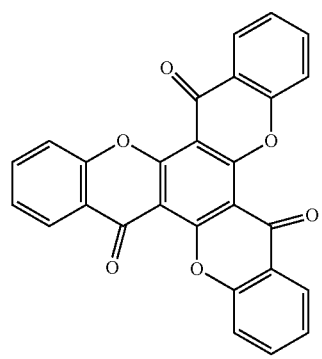
83 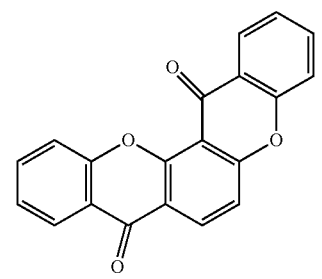
84 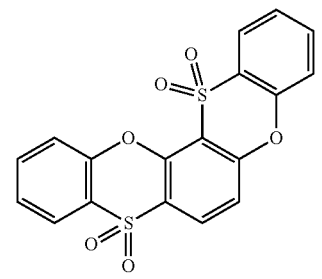
85 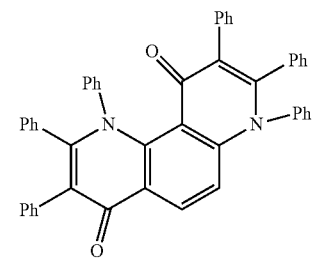
86 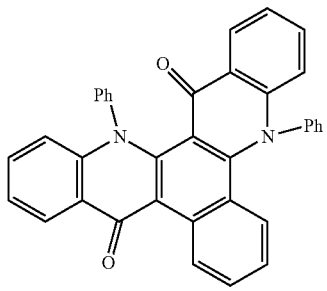
87 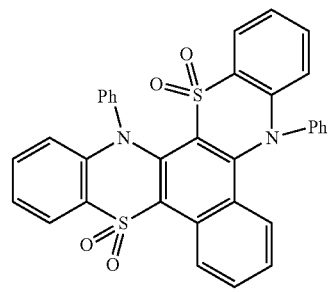
88 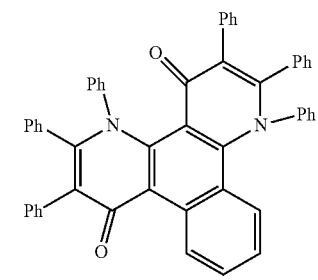
91 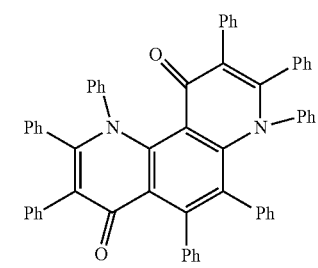
92 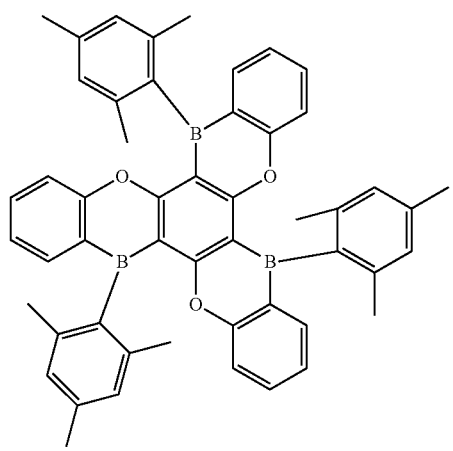
93 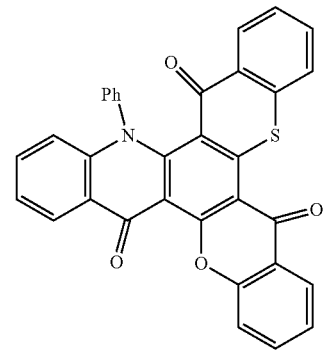

-continued

94
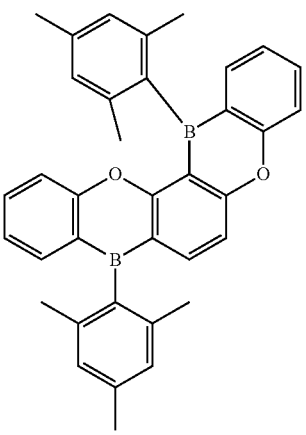

95
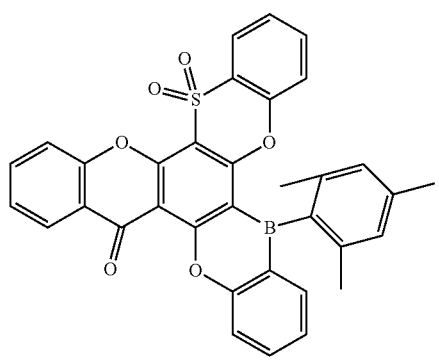

101
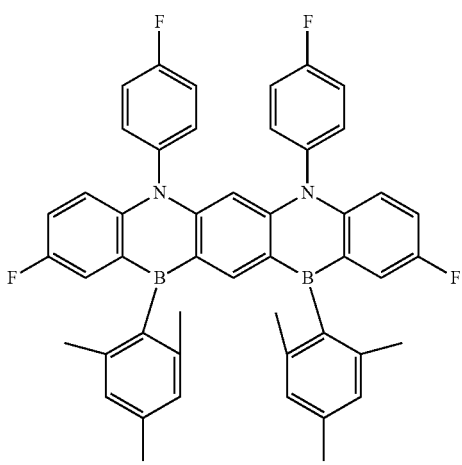

103
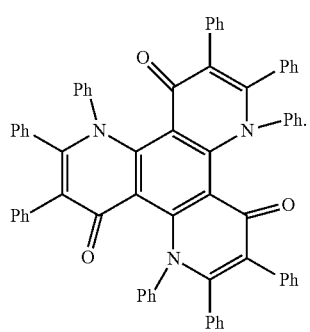

11. An organic electroluminescence device, comprising:
a first electrode;
a hole transport region on the first electrode;
an emission layer on the hole transport region;
an electron transport region on the emission layer; and
a second electrode on the electron transport region,
wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, and a compound of two or more thereof, a mixture of two or more thereof, and oxides thereof, and
wherein the emission layer includes a polycyclic compound represented by any one among the following Formula 1 to Formula 3:

[Formula 1]
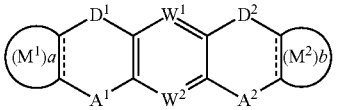

[Formula 2]
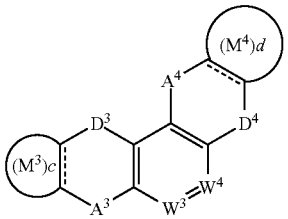

[Formula 3]
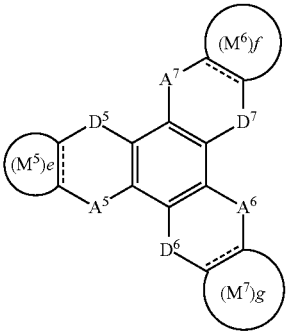

in Formula 1 to Formula 3,
$A^1$ to $A^7$ are each independently CO, $BR_1$, $SiR_2R_3$, $GeR_4R_5$, $POR_6$, $PSR_7$, SO, or $SO_2$,
$D^1$ to $D^7$ are each independently $NR_8$, O, S, or Se,
$W^1$ to $W^4$ are each independently N or $CR_9$,
a to g are each independently 0 or 1,
rings $M^1$ to $M^7$ are each independently a substituted or unsubstituted aryl group having 6 to 30 ring carbon atoms, or a substituted or unsubstituted heteroaryl group having 2 to 30 ring carbon atoms,
$R_1$ to $R_8$ are each independently a hydrogen atom, a deuterium atom, a halogen atom, a cyano group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms,
$R_9$ is a hydrogen atom, a deuterium atom, a halogen atom, a cyano group, a phosphine oxide group, a phosphine sulfide group, a carbonyl group, a boron group, a substituted or unsubstituted oxy group, a substituted or unsubstituted thiol group, a substituted or unsubstituted amino group, a substituted or unsubstituted silyl group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, when $D^3$ is $NR_8$ and $A^3$ and $A^4$ are CO, $D^4$ is $NR_8$, O, or Se, when $D^5$ to $D^7$ are $NR_8$, at least one $R^8$ is a halogen atom, a cyano group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, when, in Formula 1, $W^1$ and We are each $CR_9$, $A^1$ and $A^2$ are each $BR_1$, $D^1$ and $D^2$ are each $NR_8$, and rings $M^1$ and $M^2$ are each a substituted or unsubstituted phenyl group, at least one selected from $R^1$, $R^9$, and rings $M^1$ and $M^2$ is substituted with a halogen atom, and when $M^1$ and $M^2$ in Formula 1 are each a six-membered ring, i) $D^1$ and $D^2$ are each not $NR_8$, or ii) at least one selected from $A^1$ and $A^2$ is $BR_1$, $SiR_2R_3$, $GeR_4R_5$, $POR_6$, or $PSR_7$, and when $M^3$ and $M^4$ in Formula 2 are each a six-membered ring, iii) $D^3$ and $D^4$ are each not $NR_8$, or iv) at least one selected from $A^3$ and $A^4$ is $BR_1$, $SiR_2R_3$, $GeR_4R_5$, $POR_6$, or $PSR_7$.

12. The organic electroluminescence device as claimed in claim 11, wherein:
    the emission layer is a delayed fluorescence emission layer including a host and a dopant, and
    the host includes the polycyclic compound represented by any one among Formula 1 to Formula 3.

13. The organic electroluminescence device as claimed in claim 11, wherein:
    the emission layer is a phosphorescence emission layer including a host and a dopant, and
    the host includes the polycyclic compound represented by any one among Formula 1 to Formula 3.

14. The organic electroluminescence device as claimed in claim 12, wherein the polycyclic compound is at least one among compounds represented in the following Compound Group 1:

[Compound Group 1]

6

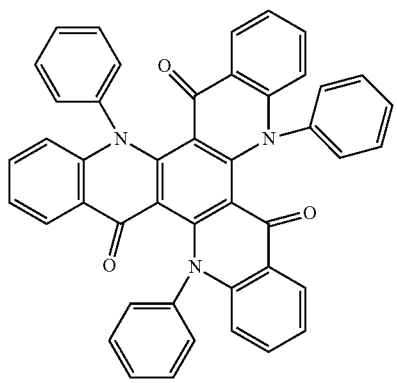

7

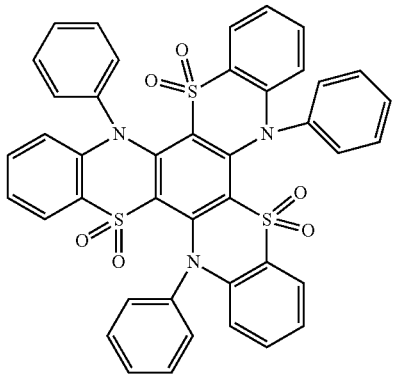

9

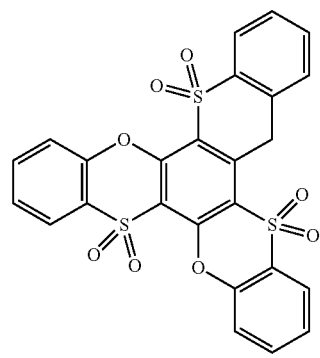

11

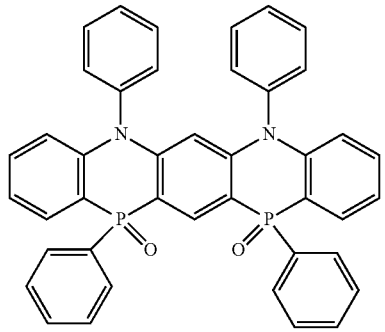

12

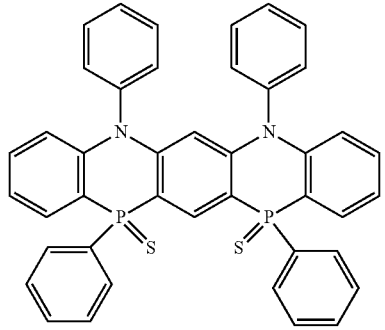

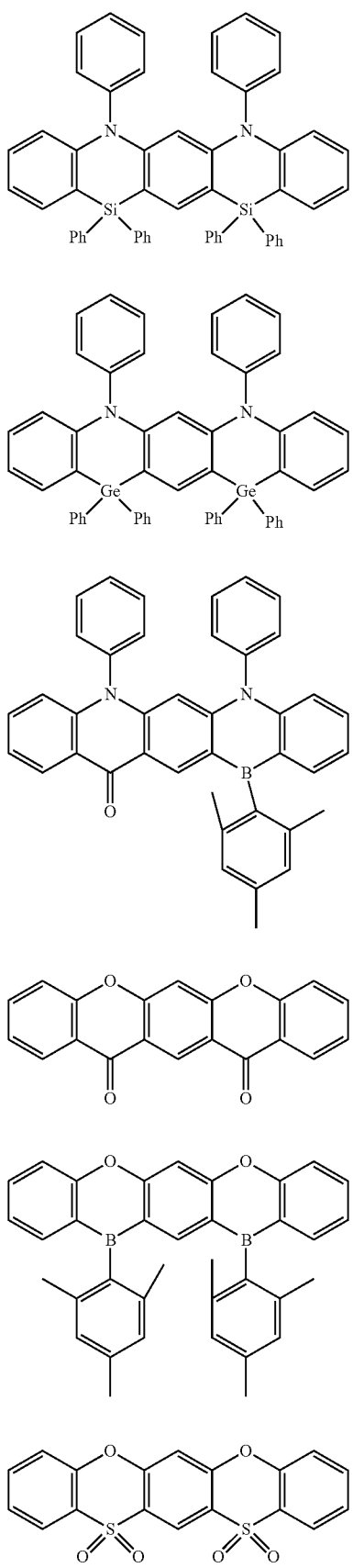
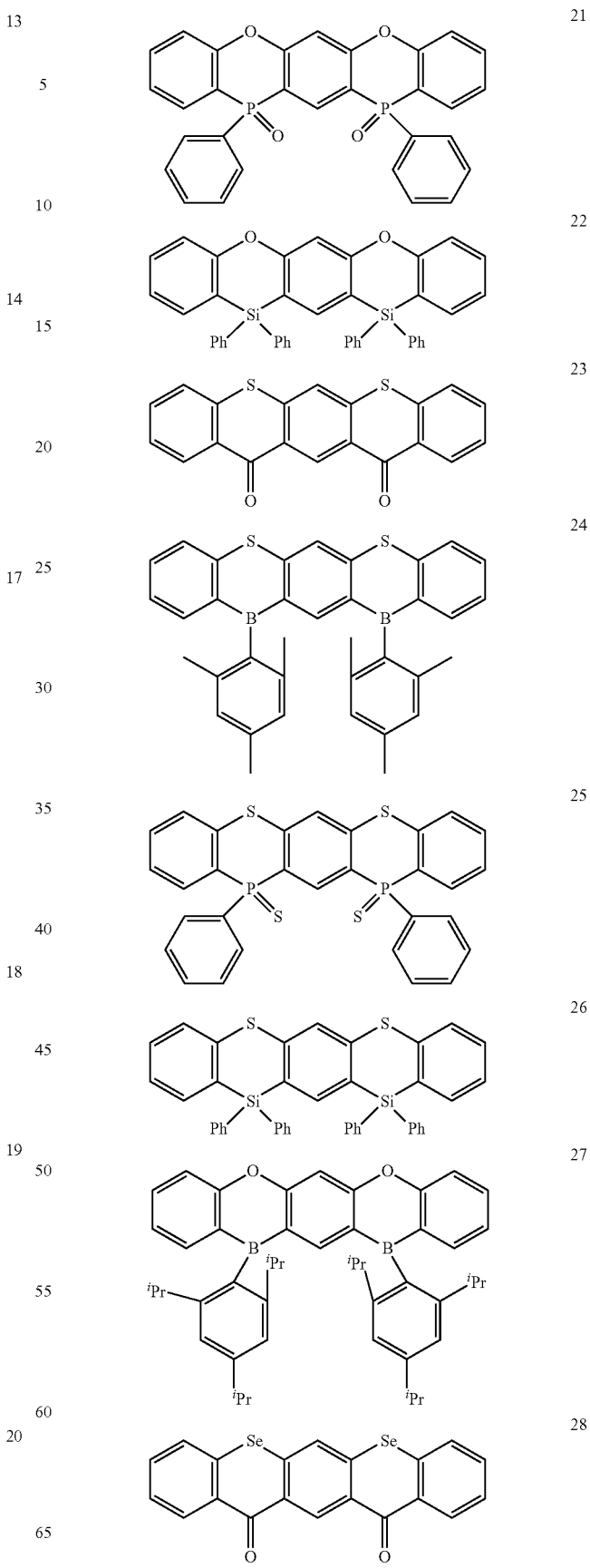

29
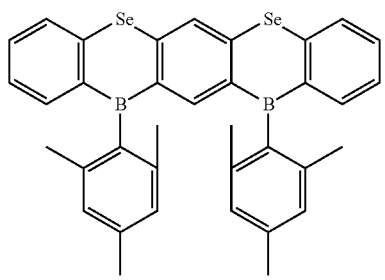
31
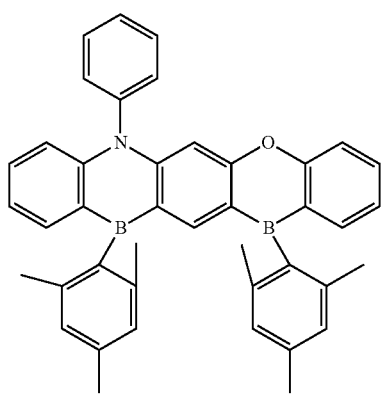
32
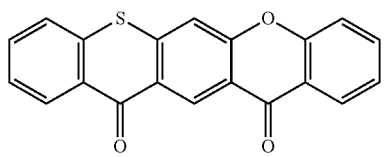
33
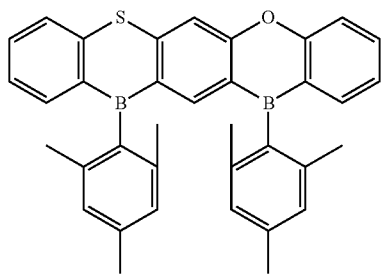
34
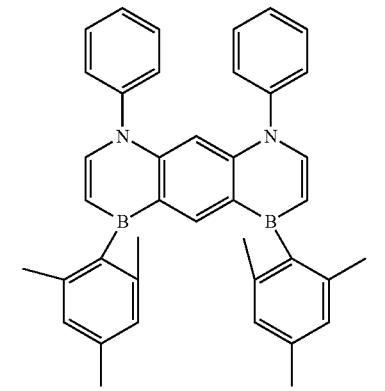
35
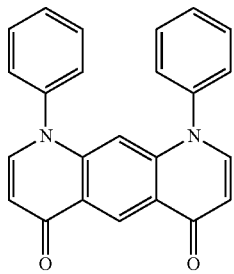
36
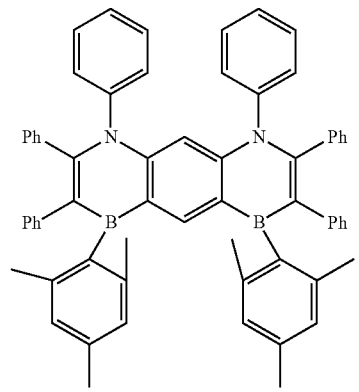
37
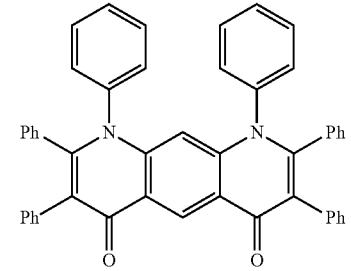
38
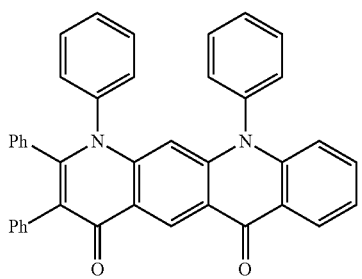
39
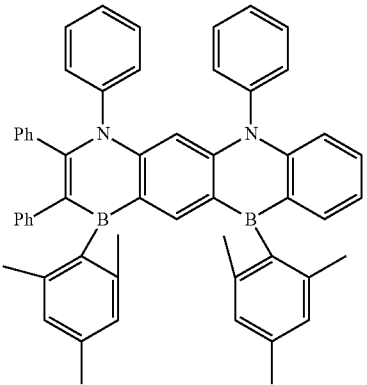

-continued
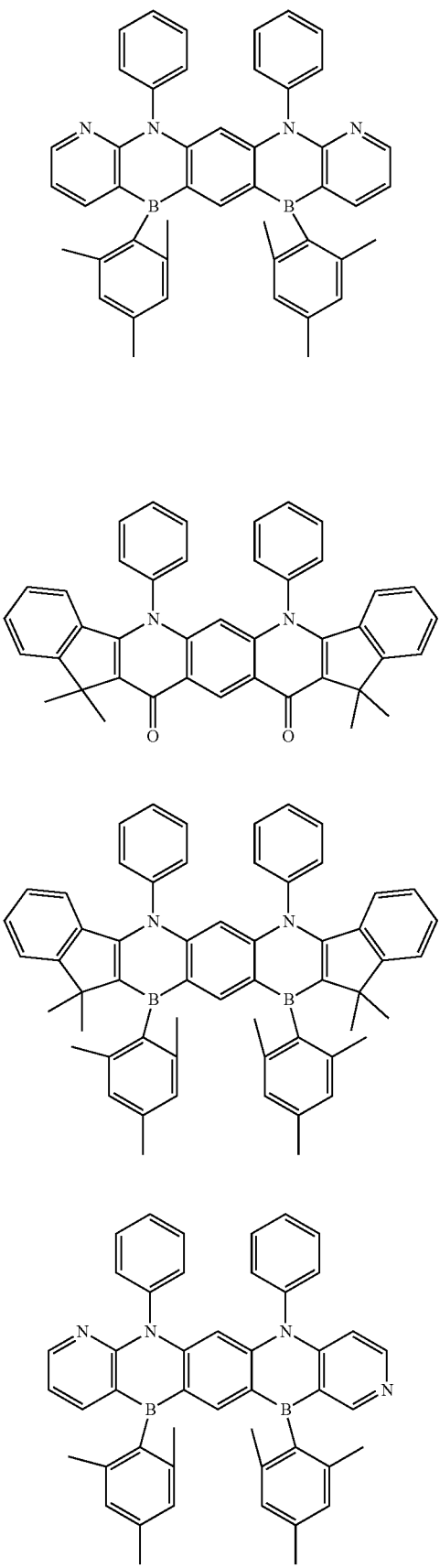
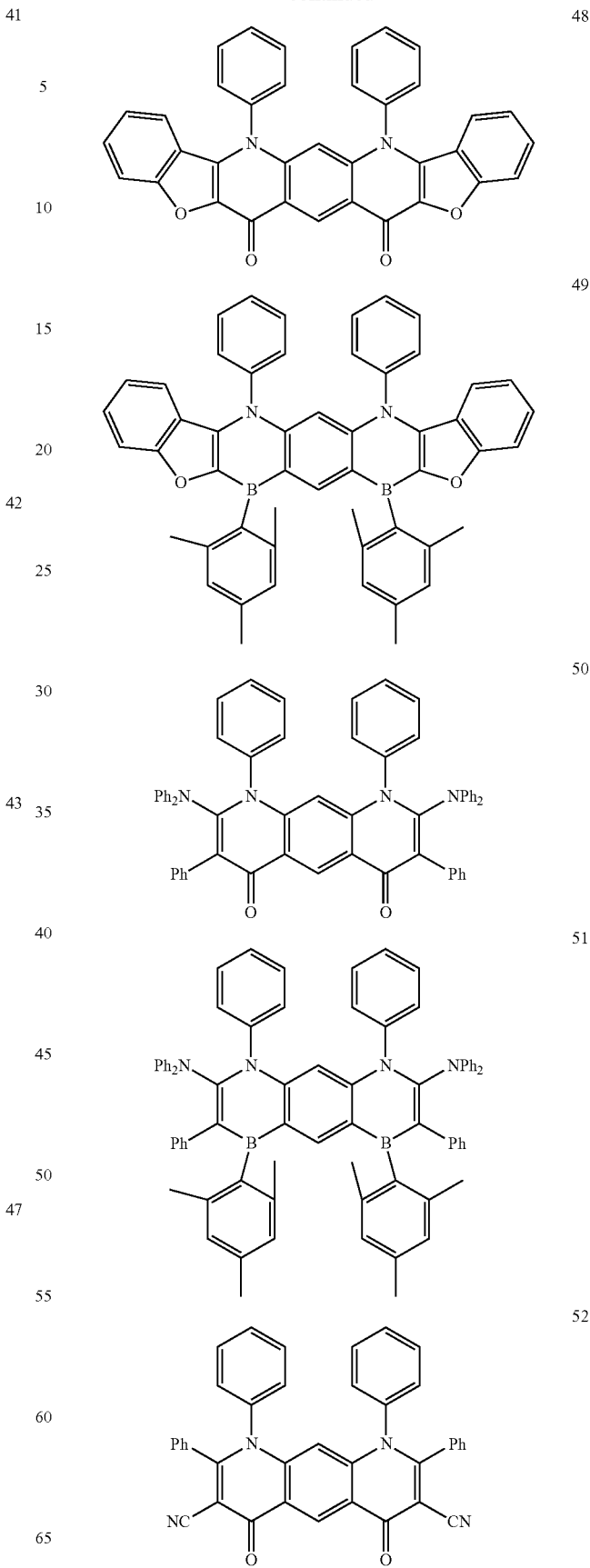

123
-continued
124
-continued
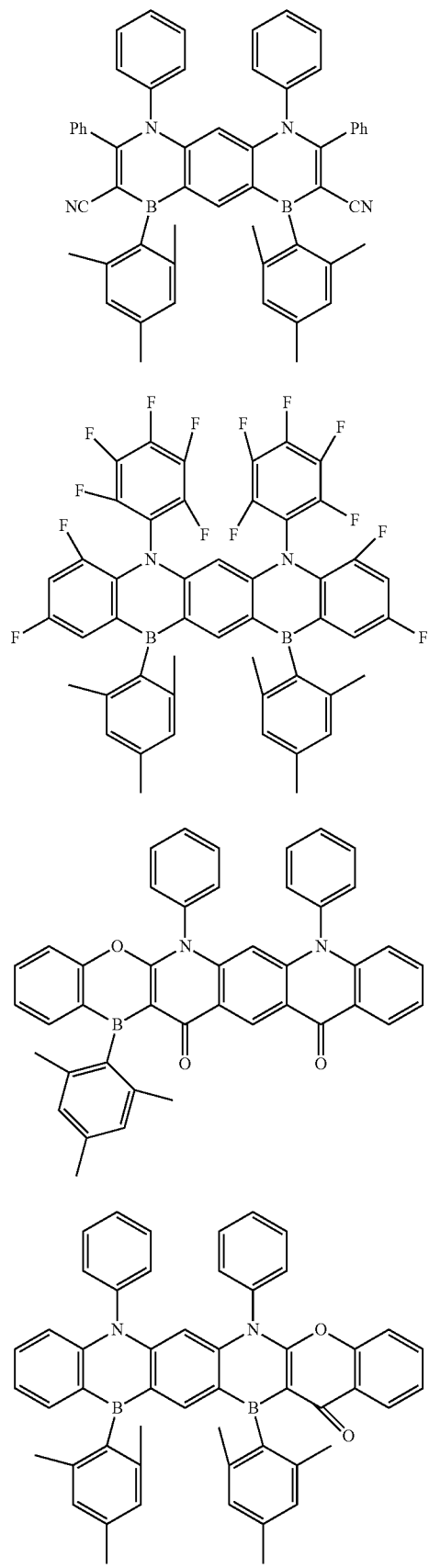
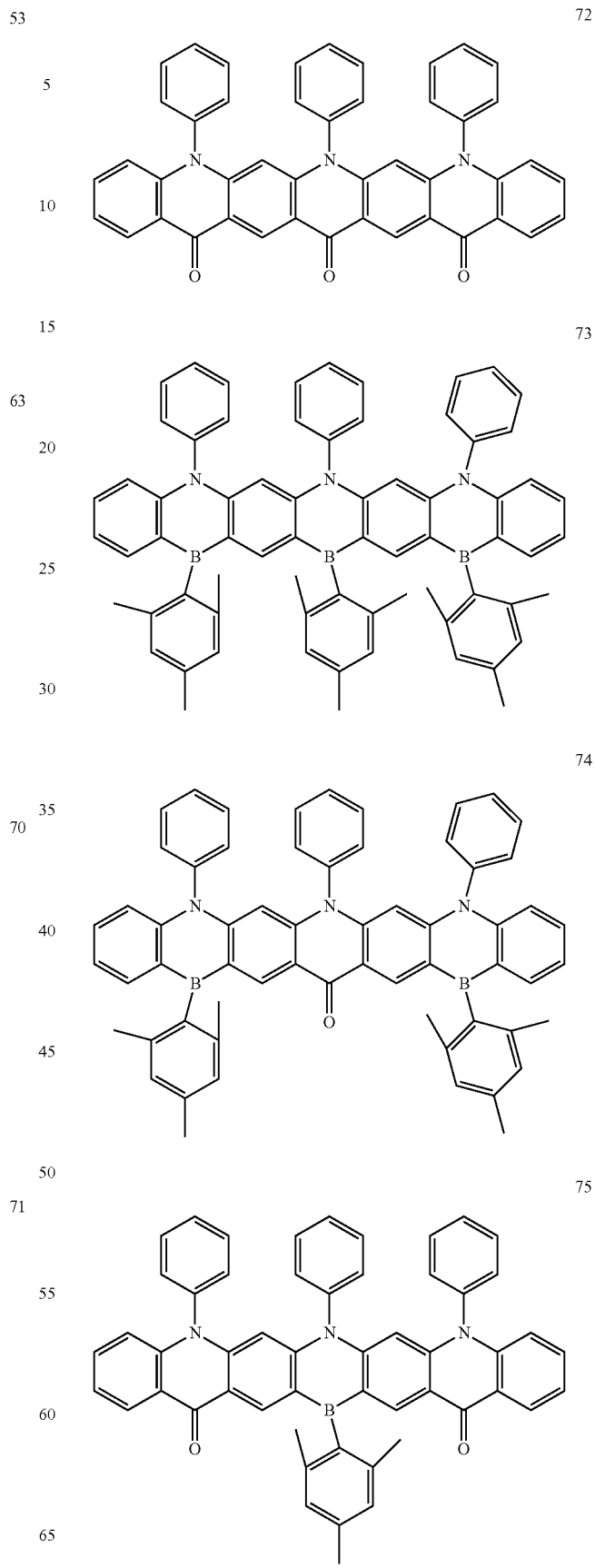

-continued
82
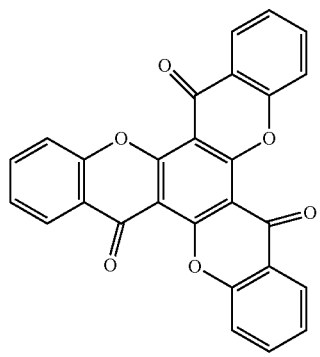
83
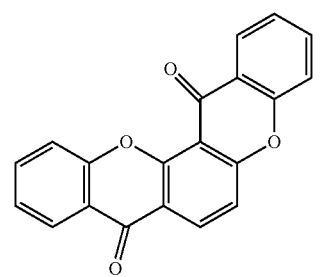
84
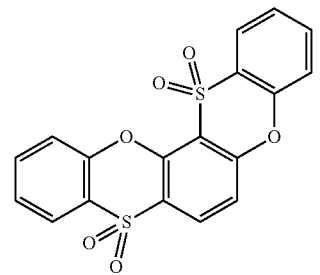
85
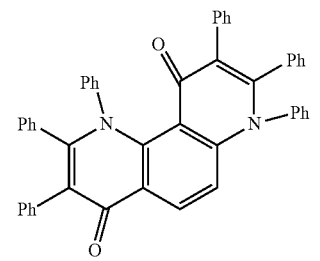
86
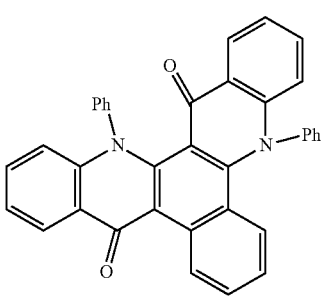
-continued
87
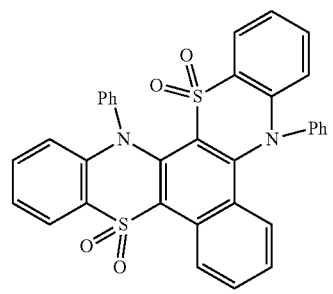
88
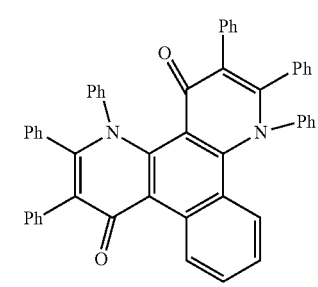
91
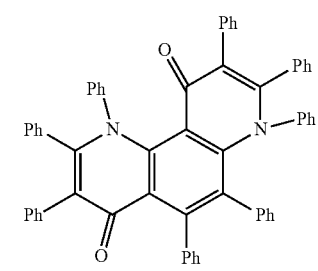
92
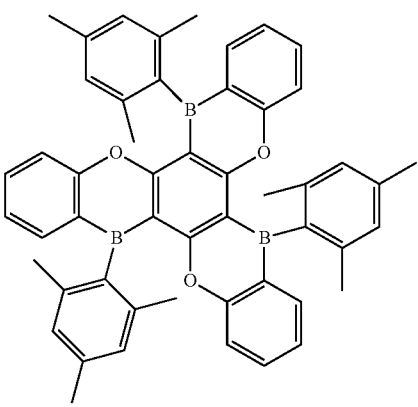
93
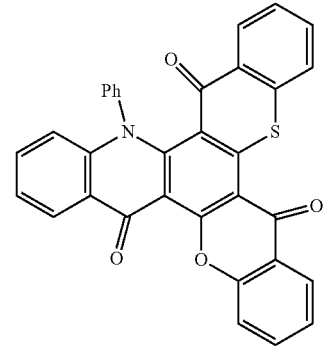

127

-continued

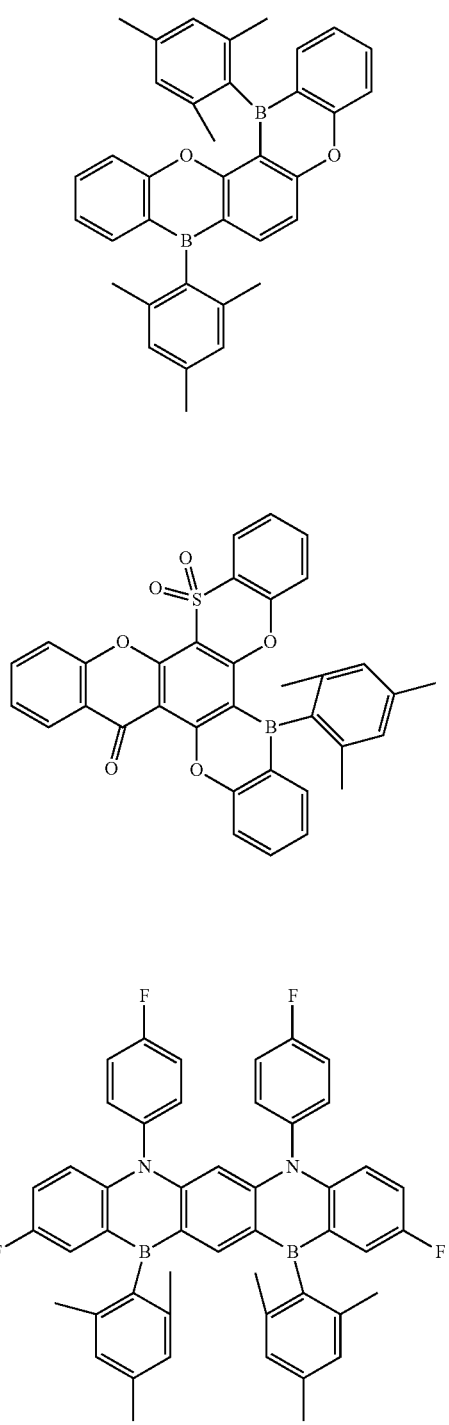

94

95

101

15. A polycyclic compound represented by any one among Formula 1 to Formula 3:

[Formula 1]

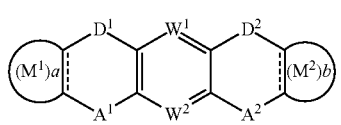

128

-continued

[Formula 2]

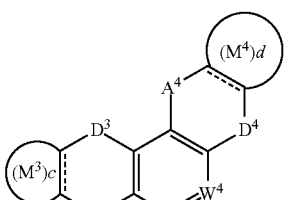

[Formula 3]

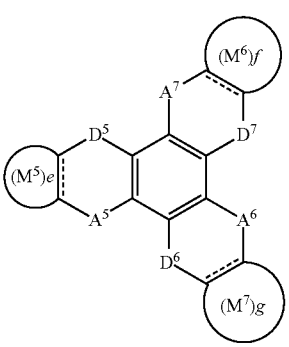

in Formula 1 to Formula 3,
$A^1$ to $A^7$ are each independently CO, $BR_1$, $SiR_2R_3$, $GeR_4R_5$, $POR_6$, $PSR_7$, SO, or $SO_2$,
$D^1$ to $D^7$ are each independently $NR_8$, O, S, or Se,
$W^1$ to $W^4$ are each independently N or $CR_9$,
a to g are each independently 0 or 1,
rings $M^1$ to $M^7$ are each independently a substituted or unsubstituted aryl group having 6 to 30 ring carbon atoms, or a substituted or unsubstituted heteroaryl group having 2 to 30 ring carbon atoms,
$R_1$ to $R_8$ are each independently a hydrogen atom, a deuterium atom, a halogen atom, a cyano group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms,
$R_9$ is a hydrogen atom, a deuterium atom, a halogen atom, a cyano group, a phosphine oxide group, a phosphine sulfide group, a carbonyl group, a boron group, a substituted or unsubstituted oxy group, a substituted or unsubstituted thiol group, a substituted or unsubstituted amino group, a substituted or unsubstituted silyl group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms,
when $D^3$ is $NR_8$ and $A^3$ and $A^4$ are CO, $D^4$ is $NR_8$, O, or Se,
when $D^5$ to $D^7$ are $NR_8$, at least one $R^8$ is a halogen atom, a cyano group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, when, in Formula 1, $W^1$ and $W^2$ are each $CR_9$, $A^1$ and $A^2$ are each $BR_1$, $D^1$ and $D^2$ are each $NR_8$, and rings $M^1$ and $M^2$ are each a substituted or unsubstituted phenyl group, at least one selected from $R^1$, $R^9$, and rings $M^1$ and $M^2$ is substituted with a halogen atom, and when $M^1$ and $M^2$ in Formula 1 are each a six-membered ring, i) $D^1$ and $D^2$ are each not $NR_8$, or ii) at least one selected from $A^1$ and $A^2$ is $BR_1$, $SiR_2R_3$, $GeR_4R_5$, $POR_6$, or $PSR_7$, and when $M^3$ and $M^4$ in Formula 2 are each a six-membered ring, iii) $D^3$ and $D^4$ are each not $NR_8$ and $A^3$ and $A^4$ are not both CO, or iv) at least one selected from $A^3$ and $A^4$ is $BR_1$, $SiR_2R_3$, $GeR_4R_5$, $POR_6$, or $PSR_7$, and wherein the polycyclic compound represented by any one among Formula 1 to Formula 3 has a lowest triplet excitation energy of about 3.0 eV or less.

16. The polycyclic compound as claimed in claim 15, wherein Formula 1 to Formula 3 are represented by the following Formula 1-1 to Formula 1-3, respectively:

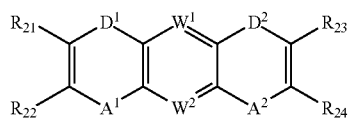

[Formula 1-1]

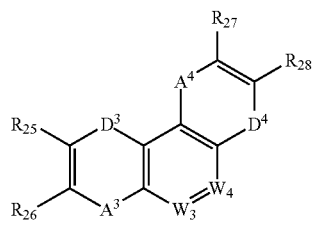

[Formula 1-2]

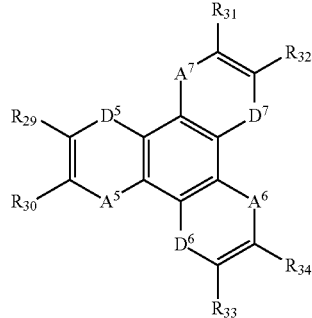

[Formula 1-3]

in Formulae 1-1 to 1-3, $R_{21}$ to $R_{34}$ are each independently a hydrogen atom, a deuterium atom, a halogen atom, a cyano group, a phosphine oxide group, a phosphine sulfide group, a silyl group, a carbonyl group, a boron group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and $A^1$ to $A^7$, $D^1$ to $D^7$, and $W^1$ to $W^4$ are the same as defined in Formula 1 to Formula 3.

17. The polycyclic compound as claimed in claim 15, wherein Formula 1 to Formula 3 are represented by the following Formula 2-1 to Formula 2-3, respectively:

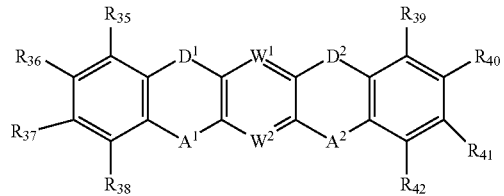

[Formula 2-1]

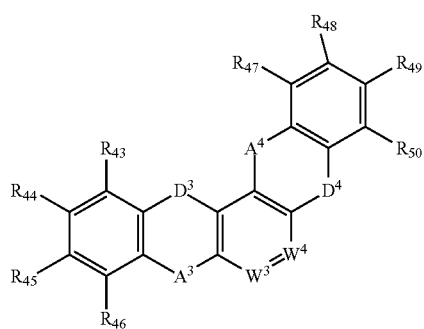

[Formula 2-2]

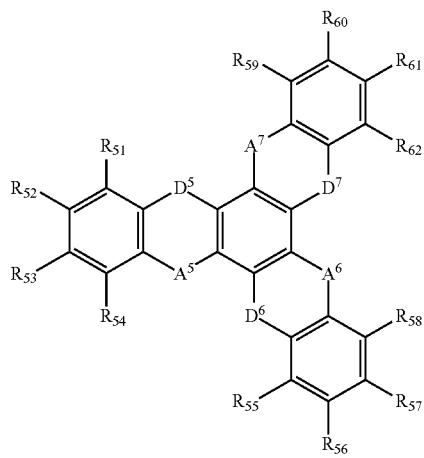

[Formula 2-3]

in Formula 2-1 to Formula 2-3, $R_{35}$ to $R_{62}$ are each independently a hydrogen atom, a deuterium atom, a halogen atom, a cyano group, a phosphine oxide group, a phosphine sulfide group, a silyl group, a carbonyl group, a boron group, a substituted or unsubstituted oxy group, a substituted or unsubstituted thiol group, a substituted or unsubstituted amino group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and $A^1$ to $A^7$, $D^1$ to $D^7$, and $W^1$ to $W^4$ are the same as defined in Formula 1 to Formula 3.

18. The polycyclic compound as claimed in claim 15, wherein:

in Formula 1, $D^1$ and $D^2$ are the same, and $A^1$ and $A^2$ are the same, and in Formula 3, $D^5$ to $D^7$ are the same, and $A^5$ to $A^7$ are the same.

19. The polycyclic compound as claimed in claim 15, wherein the polycyclic compound represented by any one among Formula 1 to Formula 3 is a material for emitting thermally activated delayed fluorescence.

20. The polycyclic compound as claimed in claim 15, wherein the polycyclic compound represented by any one among Formula 1 to Formula 3 is a phosphorescence host material.

21. The polycyclic compound as claimed in claim 15, wherein the polycyclic compound represented by any one among Formula 1 to Formula 3 is at least one among compounds represented in the following Compound Group 1:

[Compound Group 1]

6

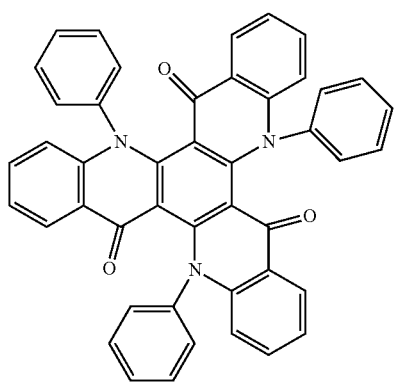

7

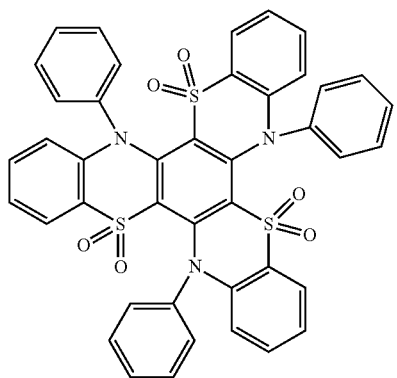

9

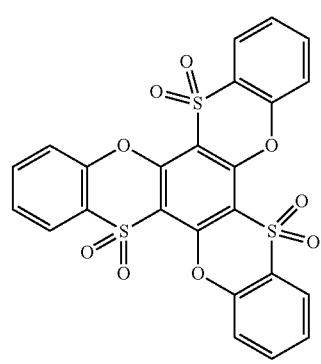

-continued

11

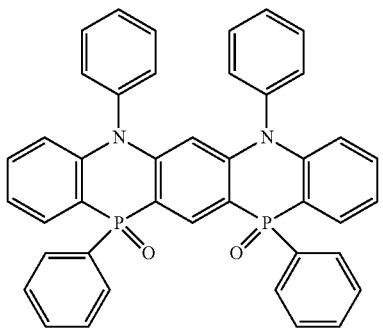

12

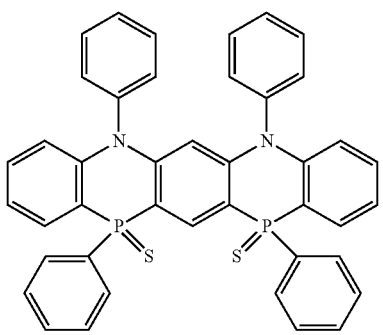

13

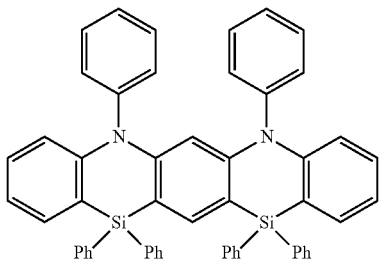

14

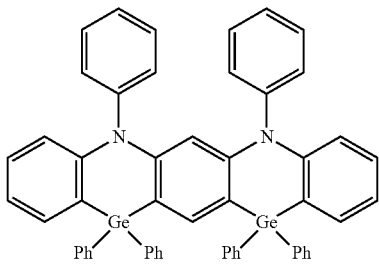

17

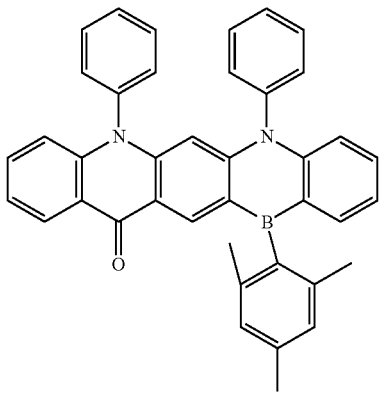

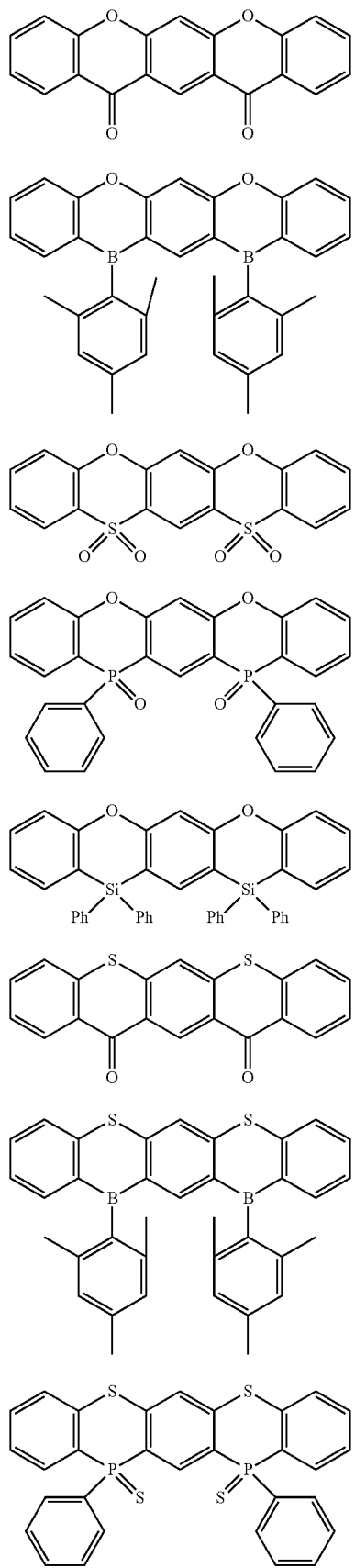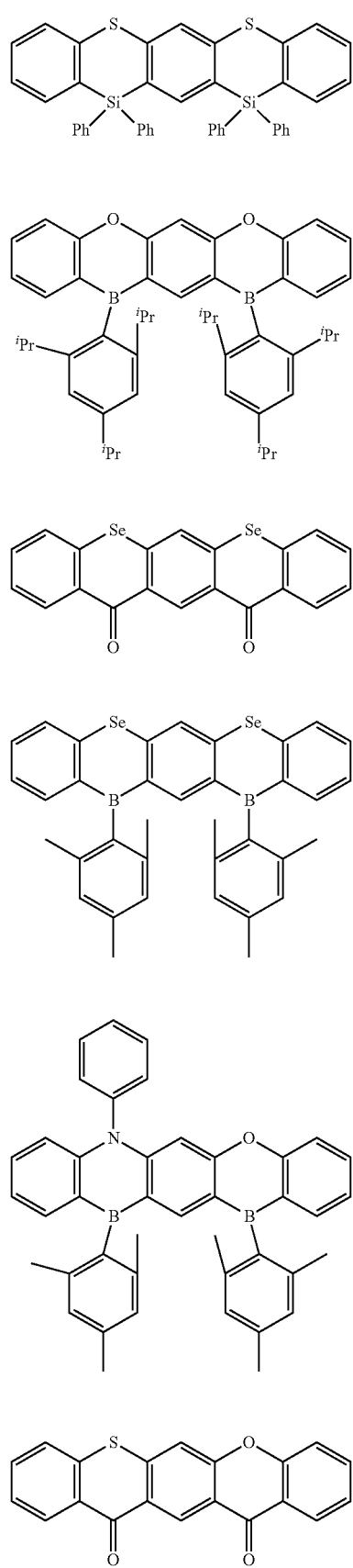

-continued
| 135 | 136 |
|---|---|
| 33 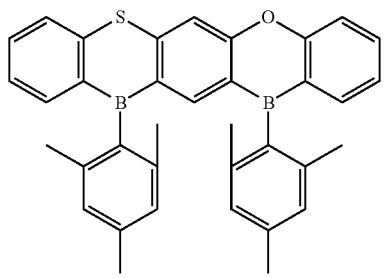 | 38 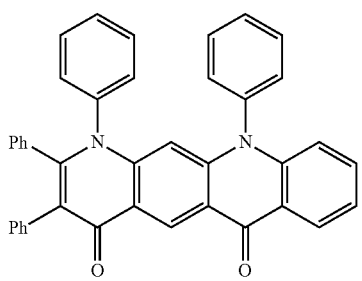 |
| 34 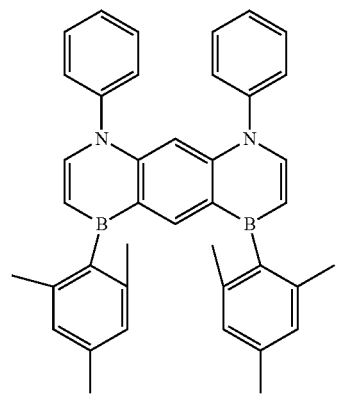 | 39 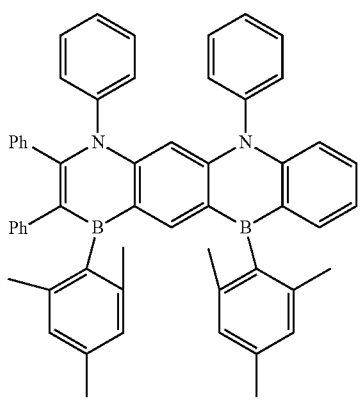 |
| 35 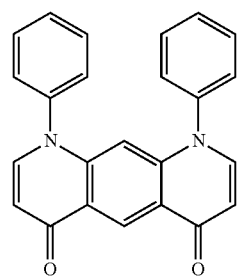 | 41 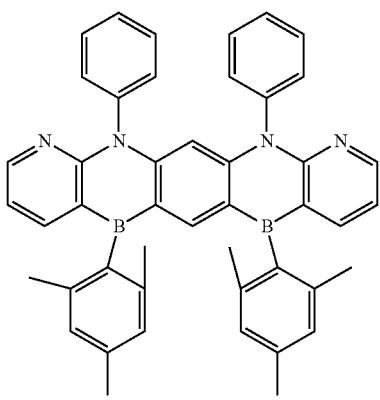 |
| 36 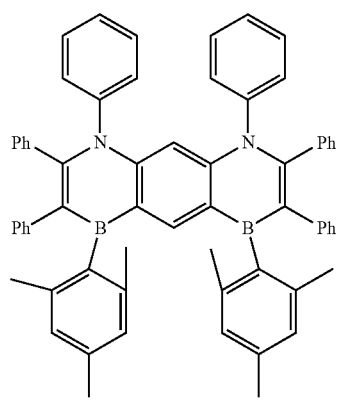 | 42 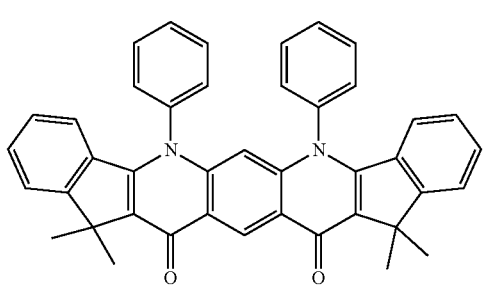 |
| 37 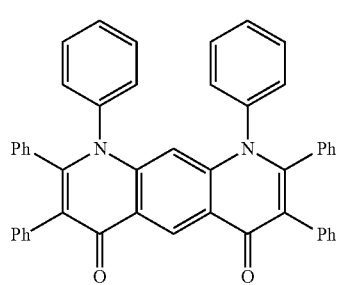 | |

43
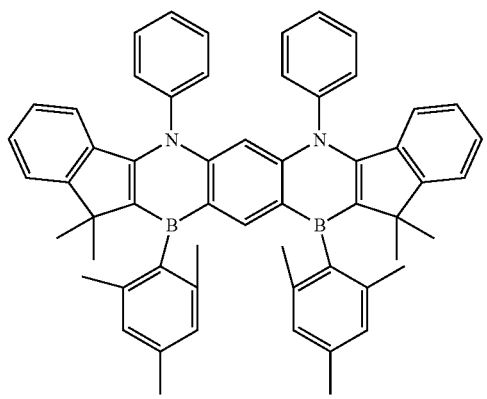
47
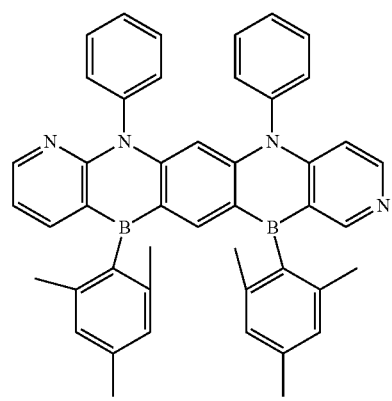
48
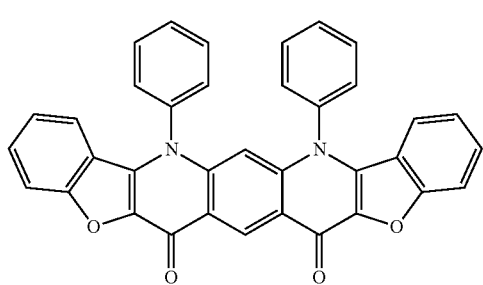
49
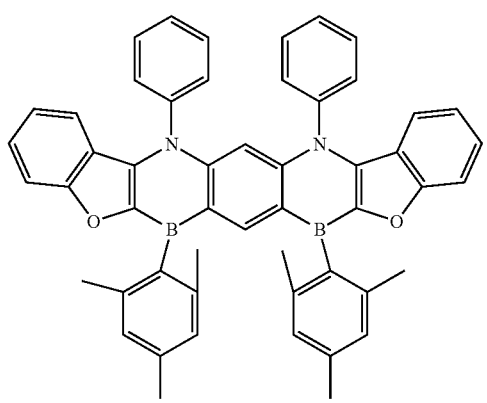
50
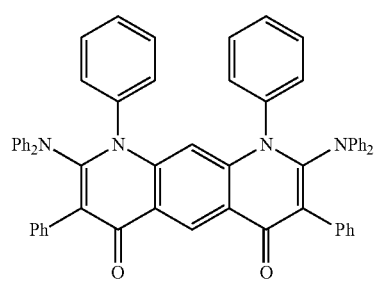
51
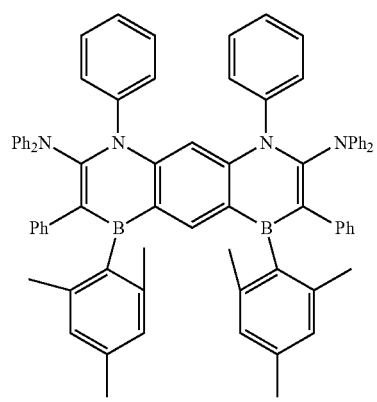
52
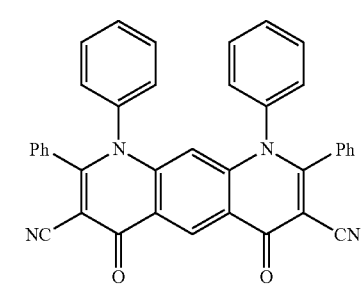
53
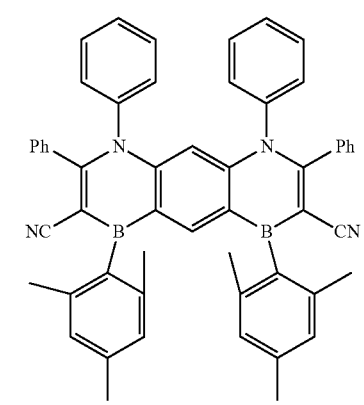

63
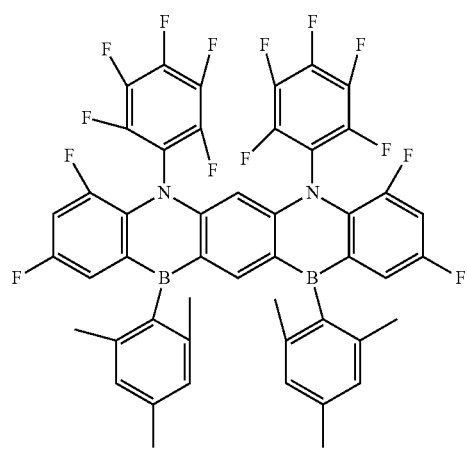
70
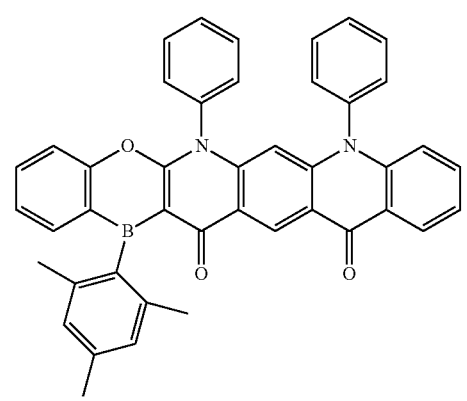
71
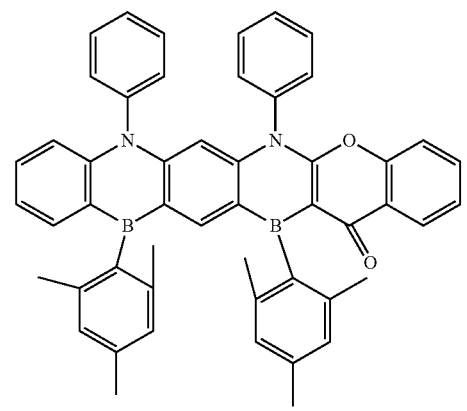
72
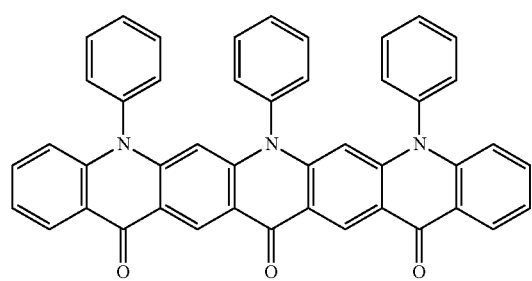
73
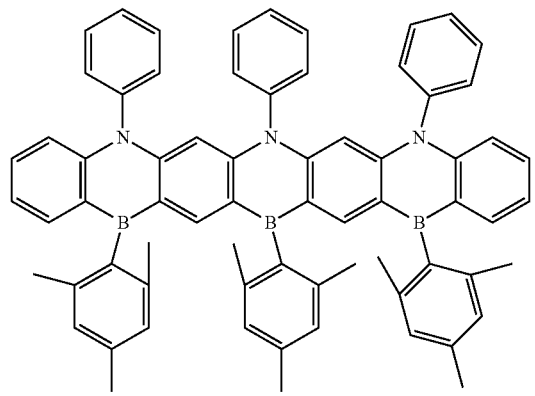
74
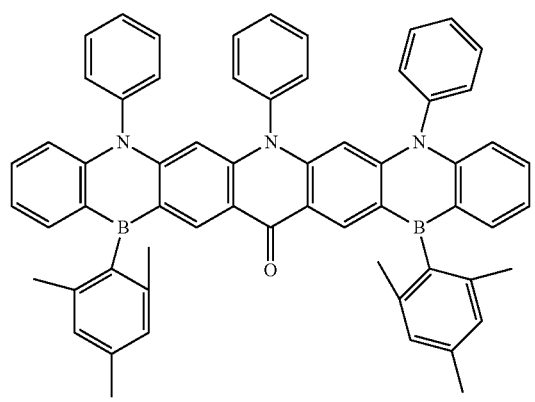
75
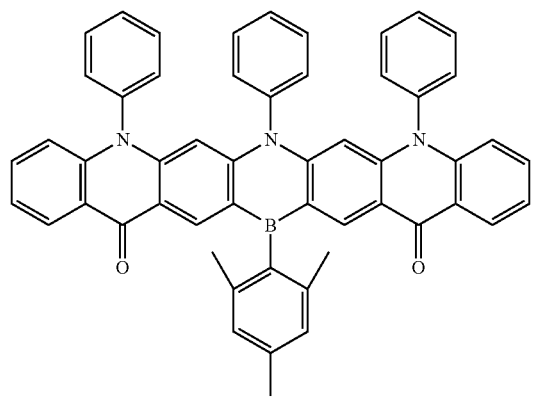
78
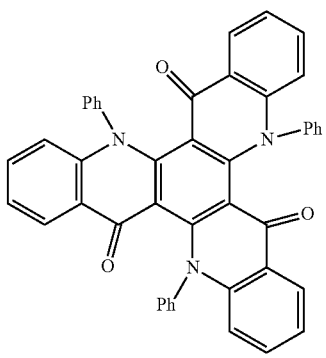

79
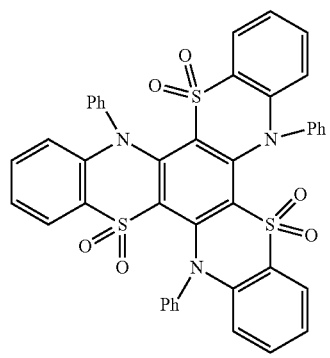
82
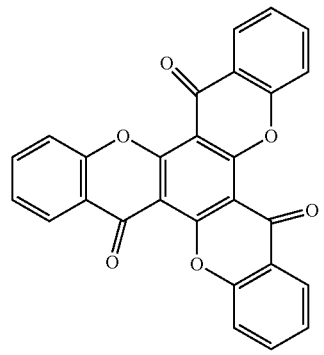
84
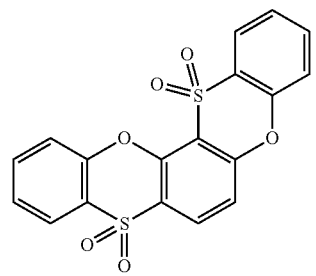
85
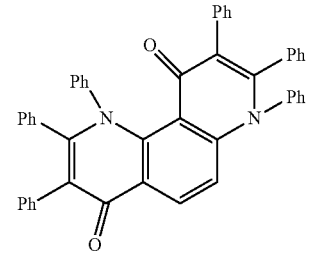
86
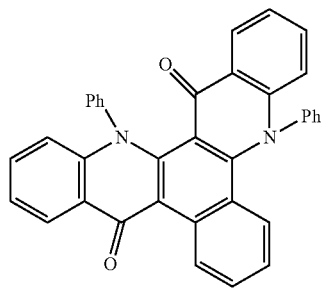
87
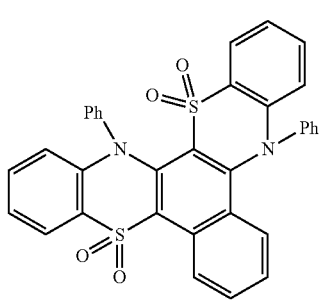
88
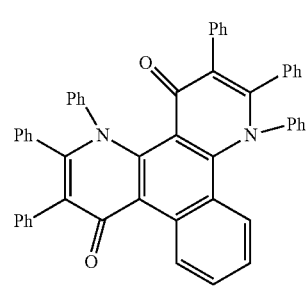
91
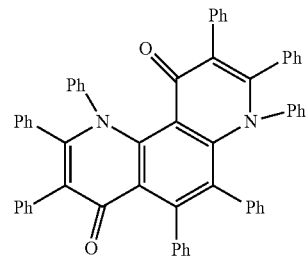
92
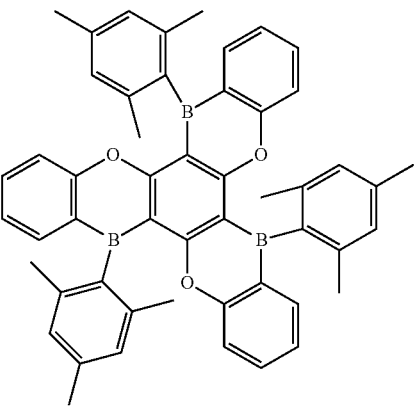
93
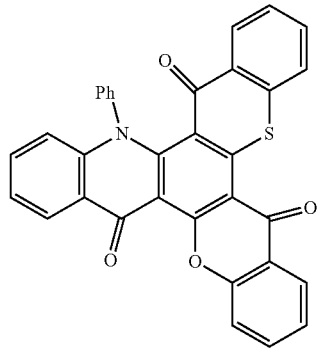

94
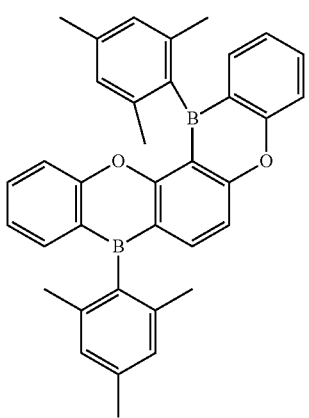
96
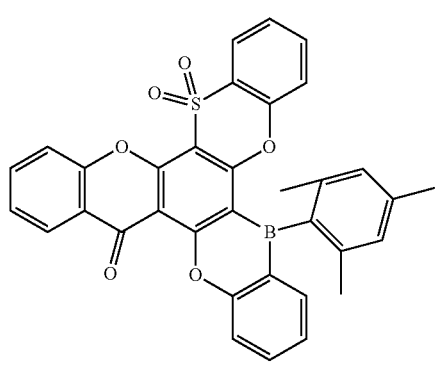
101
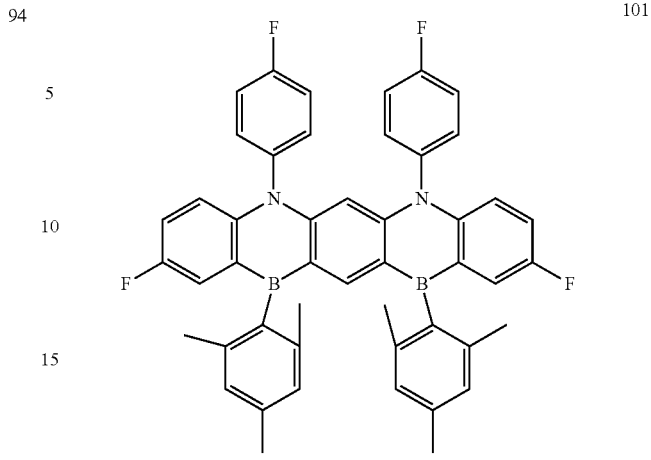
103
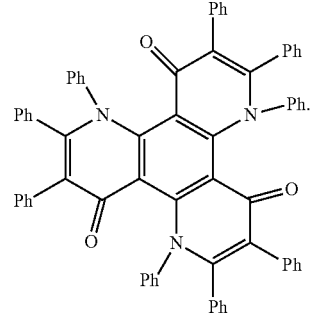
* * * * *